US011065328B2

(12) United States Patent
Rottier et al.

(10) Patent No.: US 11,065,328 B2
(45) Date of Patent: Jul. 20, 2021

(54) VACCINE AGAINST INFECTIOUS BRONCHITIS VIRUS

(71) Applicant: Boehringer Ingelheim Vetmedica GmbH, Ingelheim am Rhein (DE)

(72) Inventors: Petrus Rottier, Groenekan (NL); Stefanus Van Beurden, Dordrecht (NL); Monique Verheije, De Bilt (NL); Egbert Mundt, Isernhagen (DE)

( * ) Notice: Subject to any disclaimer, the term of this patent is extended or adjusted under 35 U.S.C. 154(b) by 470 days.

(21) Appl. No.: 15/622,672

(22) Filed: Jun. 14, 2017

(65) Prior Publication Data

US 2017/0360921 A1    Dec. 21, 2017

(30) Foreign Application Priority Data

Jun. 16, 2016 (EP) .................................. 16174857

(51) Int. Cl.
| | |
|---|---|
| A61K 39/215 | (2006.01) |
| A61K 39/12 | (2006.01) |
| C12N 7/00 | (2006.01) |
| A61K 39/00 | (2006.01) |

(52) U.S. Cl.
CPC ............ *A61K 39/215* (2013.01); *A61K 39/12* (2013.01); *C12N 7/00* (2013.01); *A61K 2039/525* (2013.01); *A61K 2039/5252* (2013.01); *A61K 2039/54* (2013.01); *A61K 2039/552* (2013.01); *C12N 2770/20034* (2013.01); *C12N 2770/20062* (2013.01)

(58) Field of Classification Search
None
See application file for complete search history.

(56) References Cited

U.S. PATENT DOCUMENTS

2017/0360921 A1    12/2017    Rottier et al.

FOREIGN PATENT DOCUMENTS

WO    2017216180 A1    12/2017

OTHER PUBLICATIONS

Yang et al. Arch Virol, vol. 161, pp. 1209-1216 (Year: 2016).*
Cavanagh et al. (Vaccine vol. 25, pp. 5558-5562 (Year: 2007).*
Cavanagh et al., "Manipulation of the infectious bronchitis coronavirus genome for vaccine development and analysis of the accessory proteins." Vaccine, vol. 25, 2007, pp. 5558-5562.
International Search Report and Written Opinion for PCT/EP2017/064442 dated Oct. 4, 2017.
Yang et al., "Recombinant infectious bronchitis virus (IBV) H120 vaccine strain expressing the hemagglutinin-neuraminidase (HN) protein of Newcastle disease virus (NDV) protects chickens against IBV and NDV challenge." Archives of Virology, vol. 161, 2016, pp. 1209-1216.
Bentley et al., "Infectious Bronchitis Virus as a Vector for the Expression of Heterologous Genes". PLOS ONE, vol. 8, No. 6, e67875, Jun. 2013, pp. 1-16.
Britton et al., "Genes 3 and 5 of Infectious Bronchitis Virus are Accessory Protein Genes". Advances in Experimental Medicine and Biology, vol. 581, Jan. 2006, pp. 363-368.
Liu et al., "Accessory proteins of SARS-CoV and other coronaviruses". Antiviral Research, vol. 109, Jul. 2014, pp. 97-109.
Mardani et al., "Infectious Bronchitis Viruses with a Novel Genomic Organization". Journal of Virology, vol. 82, No. 4, Feb. 2008, pp. 2013-2024.
Schaecher et al., "The ORF7b Protein of Severe Acute Respiratory Syndrome Coronavirus (SARS-CoV) is Expressed in Virus-Infected Cells and Incorporated into SARS-CoV Particles". Journal of Virology, vol. 81, No. 2, Jan. 2007, pp. 718-731.
Shen et al., "Towards construction of viral vectors based on avian coronavirus infecctious bronchitis virus for gene delivery and vaccine development". Journal of Virological Methods, vol. 160, 2009, pp. 48-56.
Yount et al., "Severe Acute Respiratory Syndrome Coronavirus Group-Specific Open Reading Frames Encode Nonessential Functions for Replication in Cell Cultures and Mice." Journal of Virology, vol. 79, No. 23, Dec. 2005, pp. 14909-14922.
Yang, Xin, et al. "Recombinant infectious bronchitis virus (IBV) H120 vaccine strain expressing the hemagglutinin-neuraminidase (HN) protein of Newcastle disease virus (NDV) protects chickens against IBV and NDV challenge." Archives of virology 161, No. 5 (2016): 1209-1216.
Geilhausen HE, Ligon FB, Lukert PD. "The pathogenesis of virulent and avirulent avian infectious bronchitis virus." Archiv für die gesamte Virusforschung 40, No. 3-4 (1973): 285-290.
Phillips JE, et al. "Changes in nonstructural protein 3 are associated with attenuation in avian coronavirus infectious bronchitis virus." Virus genes 44, No. 1 (2012): 63-74.
Zhao, Fangfang, et al. "Analysis of a QX-like avian infectious bronchitis virus genome identified recombination in the region containing the ORF 5a, ORF 5b, and nucleocapsid protein gene sequences." Virus genes 46, No. 3 (2013): 454-464.

* cited by examiner

*Primary Examiner* — Shanon A. Foley
*Assistant Examiner* — Myron G Hill
(74) *Attorney, Agent, or Firm* — Jamie Graham; John Ezcurra; Suzanne Shope

(57) ABSTRACT

Embodiments of the present invention relate to an infectious bronchitis virus (IBV) and an immunogenic composition comprising an IBV, respectively, wherein the ORF 3a and/or the ORF 3b and/or the ORF 5a and/or the ORF 5b is inactivated. Furthermore, aspects of the present invention relate to methods for immunizing a subject comprising administering to such subject the immunogenic composition of the present invention. Moreover, embodiments of the present invention relate to methods of treating or preventing clinical signs caused by IBV in a subject of need, the method comprising administering to the subject a therapeutically effective amount of an immunogenic composition according to the embodiments of the present invention.

15 Claims, No Drawings

Specification includes a Sequence Listing.

SEQUENCE LISTING

<160> NUMBER OF SEQ ID NOS: 38

<210> SEQ ID NO 1
<211> LENGTH: 348
<212> TYPE: RNA
<213> ORGANISM: Infectious Bronchitis Virus

<400> SEQUENCE: 1

| augauccaaa gucccacguc cuucuuaaua guauuaauuu ugcuuuggug uaaacuugua | 60 |
| cuaaguuguu uuagagaguu uauuauagcg cuucaacaac uaacacaagu uuuacuccaa | 120 |
| auuaucgaua guaauuuaca gucuagacug acccuuuggc acagucuaga cuauguuaa | 180 |
| acuuagaagc aauuauugaa acuggugauc aagugauuca aaaaaucagu uucaauuuac | 240 |
| agcauauuuc aaguguauua aacacagaag uauuugaccc cuuugacuau uguuauuaca | 300 |
| gaggagguaa uuuuugggaa auagagucag cugaagauug uucagguc | 348 |

<210> SEQ ID NO 2
<211> LENGTH: 385
<212> TYPE: RNA
<213> ORGANISM: Infectious Bronchitis Virus

<400> SEQUENCE: 2

| augaaauggc ugacuaguuu uggaagagca guuauuucuu guuauaaagc ccuacuauua | 60 |
| acucaguuaa gaguauuaga uagguuaauu uuagaucacg gaccaaaacg cgucuuaacg | 120 |
| ugugguaggc gagugcuuuu aucucaauua gauuuaguuu auagguuggc auauacgccc | 180 |
| acccaaucgc ugguaugaau aauaguaaag auaauccuuu ucgcggagca auagcaagaa | 240 |
| aagcgcgaau uuaucugaga gaaggauuag agugguuua cuuucuuaac aaagcaggac | 300 |
| aagcagagcc uugucccgcg uguaccuccc uaguauucca agggaaaacu gugaggaac | 360 |
| acacagauaa uaauaaucuu uuguc | 385 |

<210> SEQ ID NO 3
<211> LENGTH: 34
<212> TYPE: DNA
<213> ORGANISM: Infectious Bronchitis Virus

<400> SEQUENCE: 3

| ctcgagttat attggtgatt ttagatgtat ccag | 34 |

<210> SEQ ID NO 4
<211> LENGTH: 30
<212> TYPE: DNA
<213> ORGANISM: Infectious Bronchitis Virus

<400> SEQUENCE: 4

| ctcgagccaa ggccatttca catacatttc | 30 |

<210> SEQ ID NO 5
<211> LENGTH: 21
<212> TYPE: DNA
<213> ORGANISM: Infectious Bronchitis Virus

<400> SEQUENCE: 5

| agcttgtgaa ctcaaacggt g | 21 |

<210> SEQ ID NO 6
<211> LENGTH: 27
<212> TYPE: DNA
<213> ORGANISM: Infectious Bronchitis Virus

```
<400> SEQUENCE: 6
ggatacatct aaaatcacca atataac                                          27

<210> SEQ ID NO 7
<211> LENGTH: 22
<212> TYPE: DNA
<213> ORGANISM: Infectious Bronchitis Virus

<400> SEQUENCE: 7
ttactataag ttcgagactg cc                                               22

<210> SEQ ID NO 8
<211> LENGTH: 18
<212> TYPE: DNA
<213> ORGANISM: Infectious Bronchitis Virus

<400> SEQUENCE: 8
caccctgcat taatgcac                                                    18

<210> SEQ ID NO 9
<211> LENGTH: 19
<212> TYPE: DNA
<213> ORGANISM: Infectious Bronchitis Virus

<400> SEQUENCE: 9
accatggcga gcggtaaga                                                   19

<210> SEQ ID NO 10
<211> LENGTH: 37
<212> TYPE: DNA
<213> ORGANISM: Infectious Bronchitis Virus

<400> SEQUENCE: 10
tttttttttt tttttttttg ctctaactct atactag                               37

<210> SEQ ID NO 11
<211> LENGTH: 22
<212> TYPE: DNA
<213> ORGANISM: Infectious Bronchitis Virus

<400> SEQUENCE: 11
ggtgtaacac cagagataaa tg                                               22

<210> SEQ ID NO 12
<211> LENGTH: 21
<212> TYPE: DNA
<213> ORGANISM: Infectious Bronchitis Virus

<400> SEQUENCE: 12
atttacgacg tcaagagcgt c                                                21

<210> SEQ ID NO 13
<211> LENGTH: 22
<212> TYPE: DNA
<213> ORGANISM: Infectious Bronchitis Virus

<400> SEQUENCE: 13
gacttagtcc tctccttgat tg                                               22

<210> SEQ ID NO 14
<211> LENGTH: 19
<212> TYPE: DNA
```

```
<213> ORGANISM: Infectious Bronchitis Virus

<400> SEQUENCE: 14
ccagtaagca ataatgtgg                                              19

<210> SEQ ID NO 15
<211> LENGTH: 20
<212> TYPE: DNA
<213> ORGANISM: Infectious Bronchitis Virus

<400> SEQUENCE: 15
tcagcatgga cgtgtggtta                                             20

<210> SEQ ID NO 16
<211> LENGTH: 20
<212> TYPE: DNA
<213> ORGANISM: Infectious Bronchitis Virus

<400> SEQUENCE: 16
ccccatgtaa atgccaacca                                             20

<210> SEQ ID NO 17
<211> LENGTH: 18
<212> TYPE: DNA
<213> ORGANISM: Infectious Bronchitis Virus

<400> SEQUENCE: 17
taaatggtga tcttgttt                                               18

<210> SEQ ID NO 18
<211> LENGTH: 19
<212> TYPE: DNA
<213> ORGANISM: Infectious Bronchitis Virus

<400> SEQUENCE: 18
cgctcttagt aacataaac                                              19

<210> SEQ ID NO 19
<211> LENGTH: 19
<212> TYPE: DNA
<213> ORGANISM: Infectious Bronchitis Virus

<400> SEQUENCE: 19
tgctgcttcc tttaataag                                              19

<210> SEQ ID NO 20
<211> LENGTH: 18
<212> TYPE: DNA
<213> ORGANISM: Infectious Bronchitis Virus

<400> SEQUENCE: 20
ctgcgacaag acctcctg                                               18

<210> SEQ ID NO 21
<211> LENGTH: 20
<212> TYPE: DNA
<213> ORGANISM: Infectious Bronchitis Virus

<400> SEQUENCE: 21
tcagcatgga cgtgtggtta                                             20

<210> SEQ ID NO 22
<211> LENGTH: 20
```

```
<212> TYPE: DNA
<213> ORGANISM: Infectious Bronchitis Virus

<400> SEQUENCE: 22
cccaggcctt gtgaaacttc                                              20

<210> SEQ ID NO 23
<211> LENGTH: 20
<212> TYPE: DNA
<213> ORGANISM: Infectious Bronchitis Virus

<400> SEQUENCE: 23
accctccgct actacgtttt                                              20

<210> SEQ ID NO 24
<211> LENGTH: 20
<212> TYPE: DNA
<213> ORGANISM: Infectious Bronchitis Virus

<400> SEQUENCE: 24
aggcaggtat catgtgacca                                              20

<210> SEQ ID NO 25
<211> LENGTH: 20
<212> TYPE: DNA
<213> ORGANISM: Infectious Bronchitis Virus

<400> SEQUENCE: 25
ggatgggttt gatgcaacca                                              20

<210> SEQ ID NO 26
<211> LENGTH: 20
<212> TYPE: DNA
<213> ORGANISM: Infectious Bronchitis Virus

<400> SEQUENCE: 26
gagaaagcac cattggcaca                                              20

<210> SEQ ID NO 27
<211> LENGTH: 20
<212> TYPE: DNA
<213> ORGANISM: Infectious Bronchitis Virus

<400> SEQUENCE: 27
tgttgtaggt tgtggtccca                                              20

<210> SEQ ID NO 28
<211> LENGTH: 19
<212> TYPE: DNA
<213> ORGANISM: Infectious Bronchitis Virus

<400> SEQUENCE: 28
ctgaggtcaa tgccttatc                                               19

<210> SEQ ID NO 29
<211> LENGTH: 174
<212> TYPE: RNA
<213> ORGANISM: Infectious Bronchitis Virus

<400> SEQUENCE: 29
augauccaaa gucccacguc cuucuuaaua guauuaauuu ugcuuggug uaaacuugua    60 cuaaguuguu uuagagaguu uauuauagcg cuucaacaac uaacacaagu uuuacuccaa  120
```

| | |
|---|---|
| auuaucgaua guaauuuaca gucuagacug acccuuuggc acagucuaga cuaa | 174 |

<210> SEQ ID NO 30
<211> LENGTH: 195
<212> TYPE: RNA
<213> ORGANISM: Infectious Bronchitis
<210> SEQ ID NO 35
<211> LENGTH: 194
<212> TYPE: RNA
<213> ORGANISM: Infectious Bronchitis Virus

<400> SEQUENCE: 35
augaaauggc ugacuaguuu uggaagagca guuauuucuu guuauaaagc ccuacuauua      60
acucaguuaa gaguauuaga uagguuaauu uuagaucacg gaccaaagcg agucuuaacg     120
ugugguaggc gagugcuuuu aucucaauua gauuuaguuu auagguuggc auauacgccc     180
acccaaucgc uggu                                                      194

<210> SEQ ID NO 36
<211> LENGTH: 90
<212> TYPE: RNA
<213> ORGANISM: Infectious Bronchitis Virus

<400> SEQUENCE: 36
augaauaaua guaaagauaa uccuuuucgc ggagcaauag caagaaaagc gcgaauuuau      60
cugagagaag gauuagagug uguuuacuuu                                      90

<210> SEQ ID NO 37
<211> LENGTH: 15
<212> TYPE: RNA
<213> ORGANISM: Artificial Sequence
<220> FEATURE:
<223> OTHER INFORMATION: Infectious Bronchitis Virus

<400> SEQUENCE: 37
uuaaauaaau aguaa                                                      15

<210> SEQ ID NO 38
<211> LENGTH: 109
<212> TYPE: PRT
<213> ORGANISM: Infectious Bronchitis Virus

<400> SEQUENCE: 38

Met Met Asn Leu Leu Asn Lys Ser Leu Glu Glu Asn Gly Ser Phe Leu
1               5                   10                  15

Thr Ala Leu Tyr Ile Phe Val Gly Phe Leu Ala Phe Tyr Leu Leu Gly
            20                  25                  30

Arg Ala Leu Gln Ala Phe Val Gln Ala Ala Asp Ala Cys Cys Leu Phe
        35                  40                  45

Trp Tyr Thr Trp Leu Val Ile Pro Gly Val Lys Gly Thr Ala Phe Val
    50                  55                  60

Tyr Lys Tyr Thr Tyr Gly Arg Lys Leu Asn Asn Ser Glu Leu Glu Ala
65                  70                  75                  80

Val Val Val Asn Glu Phe Pro Lys Asn Gly Trp Asn Lys Asn Pro
                85                  90                  95

Ala Asn Phe Gln Asp Val Gln Arg Asn Lys Leu Tyr Ser
            100                 105

VACCINE AGAINST INFECTIOUS BRONCHITIS VIRUS

SEQUENCE LISTING

This application contains a sequence listing in accordance with 37 C.F.R. 1.821-1.825. The sequence listing accompanying this application is hereby incorporated by reference in its entirety.

BACKGROUND OF THE INVENTION

Avian coronavirus infectious bronchitis virus (IBV) is the prototype gammacoronavirus of the family Coronaviridae, order Nidovirales. Infectious bronchitis virus principally infects the upper respiratory epithelium of chickens, causing a respiratory disease, commonly complicated by secondary bacterial pathogens (Cook et al 2012. Avian Pathol. 41:239-250). Some IBV strains additionally affect the renal tubuli, oviduct and parts of the gastrointestinal tract, leading to pathological lesions and clinical symptoms in these organ systems. The virus has a worldwide presence in both commercial and backyard chicken. Due to its high genomic variability IBV is discriminated in a wide variety of geno-, sero- and protectotypes. IBV is currently regarded as one of the economically most relevant viral pathogens in the poultry industry.

Infectious bronchitis virus is an enveloped virus with a positive sense single-stranded RNA genome of 27.6 kb (Cavanagh 2007. Vet. Res. 38:281-297). The first two-third of the viral genome comprises large coding region (also designated as gene 1), divided into two open reading frames 1a and 1b, which encode for 15 nonstructural proteins involved in RNA replication, editing, and transcription. The last one-third of the viral genome codes for structural proteins: the spike protein (S, encoded by gene 2), the envelope protein (E, encoded by gene 3c), the membrane protein (M, encoded by gene 4), and the nucleocapsid protein (N, encoded by gene 6). Proteins S, E and M are part of the viral envelope while protein N forms along with the viral RNA the ribonucleoprotein core. The spike protein is a dimeric or trimeric transmembrane protein, which is proteolytic ally cleaved into two subunits, S1 and S2. The heavily glycosylated S1 domain forms the 'head' of the spike protein and contains the receptor binding domain that interacts with 2,3-linked sialic acids on the host cell surface (Promkuntod et al 2014. Virology. 448:26-32). The S2 domain contains the remaining part of the ectodomain (the 'stalk'), the transmembrane domain and the cytoplasmatic located endodomain. The coronavirus spike protein principally determines host species tropism (Kuo et al 2000. J. Virol. 74:1393-1406).

Interspersed between the coronavirus structural genes is a variable number of group specific accessory genes located (Liu et al 2014. Antiviral Res. 109:97-109). Most of these genes are nonstructural, and their expression is not essential for virus replication in either embryonated chicken eggs or in cell culture. The IBV genome contains the accessory genes 3 and 5, encoding the proteins 3a and 3b, and 5a and 5b, respectively (Britton et al 2006; Adv Exp Med Biol.; 581:363-8). In addition, there is an open reading frame located in the intergenic region (IR) between genes 4 and 5 (Bentley et al 2013; J. Virol. 87:2128-2136).

Gene 3 is functionally tricistronic, encoding three proteins, 3a, 3b, and 3c. The latter being the structural E protein of IBV. Gene 5 is functionally bicistronic and encodes two proteins, 5a and 5b (Britton et al 2006; Adv Exp Med Biol.; 581:363-8). The accessory IBV proteins 3a and 3b were recently found to induce a delayed activation of the type I interferon response in vitro, with protein 3a additionally being involved in resistance of IBV to the cellular antiviral state induced by IFN (Kint et al 2015: J. Virol. 89:1156-1167; Kint et al 2015: J. Virol. doi: JVI.01057-15.). Accessory protein 5b contributes to host shut off, hereby amongst others inhibiting the translation of type I IFN (Kint, PhD thesis 2015).

Britton et al 2006 (Adv Exp Med Biol.; 581:363-8) have deleted the expression of IBV 3a, 3b, 5a, and 5b proteins and have shown that none of the gene products is essential for replication per se and that they can be considered to be accessory proteins. Further, Bentley et al. 2013 (PLOS One. 8(6):e67875) disclose the replacement of ORFs 3a and 3b with hRluc and the replacement of Gene 5 with an IBV codon-optimized version of the hRluc. However, it has not been shown or suggested that the replacement of gene 3a and 3b or gene 5 would lead to any different phenotype (such as attenuation) than the wildtype IBV. Rather, Bentley et al focus on whether or not marker genes can be introduced into the IBV genome. In this respect Bentley et al disclose that recombinant IBV stability varied depending on the genome region being replaced.

To date the most widely used live-attenuated IBV vaccine strains was developed back in the 1960s in The Netherlands, by serial passaging of a Massachusetts-like IBV strain (Bijlenga et al 2004; Avian Pathol. 33:550-557). During the passaging, the virus became adapted to embryonated eggs, with embryonic dwarfing observed until the 30th passage, and embryo mortality at higher passages. After 51 passages, the virus caused embryonic death within 48 hpi, but the 52nd passage (called H52) was still too virulent for chicks. After another 68 passages, the virus (known as H120) was sufficiently attenuated to be safely used in young chicks, while still inducing a protective immune response. However, the emergence of new IBV serotypes in the 1970s, for which the traditional Massachusetts-like vaccines did not protect sufficiently, prompted the development of new live-attenuated vaccines and research into other vaccine-types potentially inducing protective immunity against multiple serotypes (Cook et al 2012. Avian Pathol. 41:239-250). Today, the most widely used IBV vaccines are still attenuated by serial passaging in embryonated eggs, which is laborious and time-consuming. In addition, this type of attenuation is random and the outcome is rather unpredictable.

Therefore, other methods than serial passaging are needed for developing IBV vaccines. Several research groups already independently developed systems to manipulate the IBV genome by recombinant techniques (Youn, et al 2005. Virology. 332:206-215; Zhou et al 2013. Vet. Microbiol. 162:53-61). However, all these reverse genetics systems are based on the non-pathogenic cell-culture adapted IBV strain Beaudette, or the highly attenuated IBV vaccine strain H120. Since these IBV strains are non-virulent (Bijlenga et al 2004. Avian Pathol. 33:550-557), protective immunity can likely only be induced by introducing virulence factors from pathogenic IBV strains. This approach may cause safety concerns, and has not yet led to registration of a recombinant IBV vaccine.

Therefore, there is a need for new and highly efficacious IBV vaccines and alternative strategies for attenuating IBV, respectively.

DETAILED DESCRIPTION OF THE INVENTION

Before the aspects of the present invention are described, it must be noted that as used herein and in the appended claims, the singular forms "a", "an", and "the" include plural reference unless the context clearly dictates otherwise. Thus, for example, reference to "an antigen" includes a plurality of antigens, reference to the "virus" is a reference to one or more viruses and equivalents thereof known to those skilled in the art, and so forth. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies as reported in the publications which might be used in connection with the invention. Nothing herein is to be construed as an admission that the invention is not entitled to antedate such disclosure by virtue of prior invention.

Composition of Matter

Embodiments of the present invention solve the problems inherent in the prior art and provides a distinct advance in the state of the art.

In one aspect, the present invention provides an IBV (infectious bronchitis virus), wherein:
the ORF 3a; and/or
the ORF 3b; and/or
the ORF 5a; and/or
the ORF 5b is inactivated.

In another aspect, the present invention also provides an IBV (infectious bronchitis virus), wherein:
the ORF 3a and ORF 3b are inactivated; or
the ORF 5a and ORF 5b are inactivated; or
the ORF 3a and ORF 3b and the ORF 5a and ORF 5b are inactivated.

In yet another aspect, the present invention provides an IBV (infectious bronchitis virus), wherein the ORF 3a and ORF 3b are inactivated.

In yet another aspect, the present invention provides an IBV (infectious bronchitis virus), wherein the ORF 5a and ORF 5b are inactivated.

In yet another aspect, the present invention provides an IBV (infectious bronchitis virus), wherein the ORF 3a and ORF 3b and the ORF 5a and ORF 5b are inactivated.

Further, aspects of the present invention provide an immunogenic composition comprising an IBV (infectious bronchitis virus), wherein:
the ORF 3a; and/or
the ORF 3b; and/or
the ORF 5a; and/or
the ORF 5b is inactivated.

In another aspect of the present invention also provides an immunogenic composition comprising an IBV (infectious bronchitis virus), wherein:
the ORF 3a and ORF 3b are inactivated; or
the ORF 5a and ORF 5b are inactivated; or
the ORF 3a and ORF 3b and the ORF 5a and ORF 5b are inactivated.

In yet another aspect, the present invention provides an immunogenic composition comprising an IBV (infectious bronchitis virus), wherein the ORF 3a is inactivated. As shown in the Examples the immunogenic composition comprising an IBV (infectious bronchitis virus) wherein the ORF 3a is inactivated has been proven to be safe and efficacious.

In yet another aspect, the present invention provides an immunogenic composition comprising an IBV (infectious bronchitis virus), wherein the ORF 3b is inactivated. As shown in the Examples the immunogenic composition comprising an IBV (infectious bronchitis virus) wherein the ORF 3b is inactivated has been proven to be safe and efficacious.

In yet another aspect, the present invention provides an immunogenic composition comprising an IBV (infectious bronchitis virus), wherein the ORF 5a is inactivated. As shown in the Examples the immunogenic composition comprising an IBV (infectious bronchitis virus) wherein the ORF 5a is inactivated has been proven to be safe and efficacious.

In another aspect, the present invention provides an immunogenic composition comprising an IBV (infectious bronchitis virus), wherein the ORF 5b is inactivated. As shown in the Examples the immunogenic composition comprising an IBV (infectious bronchitis virus) wherein the ORF 5b is inactivated has been proven to be safe and efficacious.

In yet another aspect, the present invention provides an immunogenic composition comprising an IBV (infectious bronchitis virus), wherein the ORF 3a and ORF 3b are inactivated. As shown in the Examples the immunogenic composition comprising an IBV (infectious bronchitis virus) wherein the ORF 3a and ORF 3b are inactivated has been proven to be safe and efficacious.

In another aspect, the present invention provides an immunogenic composition comprising an IBV (infectious bronchitis virus), wherein the ORF 5a and ORF 5b are inactivated. As shown in the Examples the immunogenic composition comprising an IBV (infectious bronchitis virus) wherein the ORF 5a and ORF 5b are inactivated has been proven to be safe and efficacious.

In another aspect, the present invention provides an immunogenic composition comprising an IBV (infectious bronchitis virus), wherein the ORF 3a and ORF 5a are inactivated. As shown in the Examples the immunogenic composition comprising an IBV (infectious bronchitis virus) wherein the ORF 3a or ORF 5a is inactivated has been proven to be safe and efficacious.

In another aspect, the present invention provides an immunogenic composition comprising an IBV (infectious bronchitis virus), wherein the ORF 3a and ORF 5b are inactivated. As shown in the Examples the immunogenic composition comprising an IBV (infectious bronchitis virus) wherein the ORF 3a or ORF 5b is inactivated has been proven to be safe and efficacious.

In another aspect, the present invention provides an immunogenic composition comprising an IBV (infectious bronchitis virus), wherein the ORF 3b and ORF 5a are inactivated. As shown in the Examples the immunogenic composition comprising an IBV (infectious bronchitis virus) wherein the ORF 3b or ORF 5a is inactivated has been proven to be safe and efficacious.

In another aspect, the present invention provides an immunogenic composition comprising an IBV (infectious bronchitis virus), wherein the ORF 3b and ORF 5b are inactivated. As shown in the Examples the immunogenic composition comprising an IBV (infectious bronchitis virus) wherein the ORF 3b or ORF 5b is inactivated has been proven to be safe and efficacious.

In another aspect, the present invention provides an immunogenic composition comprising an IBV (infectious bronchitis virus), wherein the ORF 3a and ORF 3b and ORF 5a are inactivated. As shown in the Examples the immunogenic composition comprising an IBV (infectious bronchitis virus) wherein the ORF 3a or ORF 3b or ORF 5a is inactivated has been proven to be safe and efficacious.

In another aspect, the present invention provides an immunogenic composition comprising an IBV (infectious bronchitis virus), wherein the ORF 3a and ORF 3b and ORF 5b are inactivated. As shown in the Examples the immunogenic composition comprising an IBV (infectious bronchitis virus) wherein the ORF 3a or ORF 3b or ORF 5b is inactivated has been proven to be safe and efficacious.

In another aspect, the present invention provides an immunogenic composition comprising an IBV (infectious bronchitis virus), wherein the ORF 5a and ORF 5b and ORF 3a are inactivated. As shown in the Examples the immunogenic composition comprising an IBV (infectious bronchitis virus) wherein the ORF 5a or ORF 5b or ORF 3a is inactivated has been proven to be safe and efficacious.

In another aspect, the present invention provides an immunogenic composition comprising an IBV (infectious bronchitis virus), wherein the ORF 5a and ORF 5b and ORF 3b are inactivated. As shown in the Examples the immunogenic composition comprising an IBV (infectious bronchitis virus) wherein the ORF 5a or ORF 5b or ORF 3b is inactivated has been proven to be safe and efficacious.

In another aspect, the present invention provides an immunogenic composition comprising an IBV (infectious bronchitis virus), wherein the ORF 3a and ORF 3b and the ORF 5a and ORF 5b are inactivated. As shown in the Examples the immunogenic composition comprising an IBV (infectious bronchitis virus) wherein the ORF 3a and ORF 3b and the ORF 5a and ORF 5b are inactivated has been proven to be safe and efficacious.

The Prior Art IBV vaccines have several disadvantages. Inactivated vaccines in general only give a humoral immune response (but limited cellular immune response) and booster vaccinations are in general necessary when inactivated IBV vaccines are used. For that reason modified live IBV vaccines (inducing humoral and cellular immune response) in general would be the preferred choice. However, modified live IBV vaccines developed so far have different drawbacks. The Beaudette IBV strain (a non-pathogenic cell-culture adapted IBV strain) is too attenuated. Other strains such as H52 may not be sufficiently attenuated resulting in damage of the respiratory tract after vaccination. Further, most widely used modified live IBV vaccines were attenuated by serial passaging in embryonated eggs, which is laborious and time-consuming. In addition, this type of attenuation is random and the outcome is rather unpredictable. There is a risk of reversion to virulence while passaged in chickens. Thus, there is a need for new recombinant modified live IBV vaccines being safe and efficacious.

Further, it was not expected that the double mutants (inactivation of ORF 3a and ORF 3b; inactivation of ORF 5a and ORF 5b) were still not overattenuated because if to many deletions/inactivations are introduced a virus can become overattenuated which results in an insufficient ability to induce a protective immune response in the vaccinated host. This phenomenon that is also called "overattenuation" has been described in the literature exemplary in Rennick et al 2015 (J Virol. 2015 February; 89(4):2192-200) for one measles virus mutant which induced a low immune response. Another example was given by Chen et al 2016 (Arch Virol. 2016, 161:77-86) where a porcine reproductive and respiratory syndrome virus was passaged too often in cell culture which have led to overattenuation as indicated by a too low immunicity in swine. Manservigi et al 2010 (Open Virol J. 2010; 4: 123-156) raised concerns that to many deletions in the genome of an herpes simplex virus 1 might result in an overattenuation which negate its value. Therefore, it was surprising that the double mutants (inactivation of ORF 3a and ORF 3b; inactivation of ORF 5a and ORF 5b) were still able to induce a protective immune response compared to the single mutants (inactivation of ORF 3a; inactivation of ORF 3b; inactivation of ORF 5a; inactivation of ORF 5b). Even more surprising, the deletion mutant having an inactivation in all four ORF's (inactivation of ORF 3a and ORF 3b and the ORF 5a and ORF 5b) did not show an overattenuated phenotype.

The term "immunogenic composition" refers to a composition that comprises at least one antigen, which elicits an immunological response in the host to which the immunogenic composition is administered. Such immunological response may be a cellular and/or antibody-mediated immune response to the immunogenic composition of the invention. Preferably, the immunogenic composition induces an immune response and, more preferably, confers protective immunity against one or more of the clinical signs of a IBV infection. The host is also described as "subject". Preferably, any of the hosts or subjects described or mentioned herein is an avian or poultry.

Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the immunogenic composition of the invention. Preferably, the host will display either a protective immunological response or a therapeutically response.

A "protective immunological response" or "protective immunity" will be demonstrated by either a reduction or lack of clinical signs normally displayed by an infected host, a quicker recovery time and/or a lowered duration of infectivity or lowered pathogen titer in the tissues or body fluids or excretions of the infected host.

In cases where the host displays a protective immunological response such that resistance to new infection will be enhanced and/or the clinical severity of the disease reduced, the immunogenic composition is described as a "vaccine".

The term "IBV" refers to the infectious bronchitis virus which is well known to the person skilled in the art. The term "IBV" encompasses all strains, genotypes, protectotypes, and serotypes of infectious bronchitis virus.

The terms "ORF 3a" and "ORF 3b" refer to the open reading frames (ORF) 3a and 3b encoded by Gene 3 of the IBV. Gene 3 of IBV is functionally tricistronic and encodes three proteins 3a, 3b, and 3c. The protein 3c is also designated E protein. ORF 3a has a length of 174 nucleotides from the start codon (AUG) to the stop codon (UAA) as shown in SEQ ID NO: 29. However, the first nucleotide (A) of the AUG of ORF 3a is the last nucleotide of the stop codon (A) of ORF S (spike) and, thus, the ORF 3a overlaps with ORF S in one nucleotide. Further, the last nucleotide of the stop codon (A) of ORF 3a is the first nucleotide (A) of the AUG of ORF 3b, and, thus, the ORF 3a overlaps with ORF 3b in one nucleotide. ORF 3b has a length of 195 nucleotides from the start codon (AUG) to the stop codon (UAA) as shown in SEQ ID NO: 30. However, the ORF 3b overlaps with ORF 3c in 20 nucleotides.

The terms "ORF 5a" and "ORF 5b" refer to the open reading frames (ORF) 5a and 5b encoded by Gene 5 of the IBV. Gene 5 is functionally bicistronic and encodes two proteins, 5a and 5b. ORF 5a has a length of 198 nucleotides from the start codon (AUG) to the stop codon (UGA) as shown in SEQ ID NO: 31. However, the ORF 5a overlaps with ORF 5b in 4 nucleotides. ORF 5b has a length of 249 nucleotides from the start codon (AUG) to the stop codon (UAG) as shown in SEQ ID NO: 32. However, the ORF 5b overlaps with ORF N in 58 nucleotides.

The term "inactivated" refers to a mutation within the ORF 3a, ORF 3b, ORF 5a, and ORF 5b. The term mutation comprises modifications in the viral RNA encoding said proteins leading to an alteration of said encoded protein. The term mutation relates to, but is not limited to, substitutions (replacement of one or several nucleotides/base pairs), deletions (removal of one, several or all nucleotides/base pairs), and/or insertions (addition of one or several nucleotides/base pairs). Thus, the term mutation comprises mutations including, but not limited to point mutations (single nucleotide mutations) or larger mutations wherein e.g. parts of the encoding (and/or non-encoding) nucleotides/base pairs are deleted (partial deletion) or all the encoding (and/or non-encoding) nucleotides/base pairs are deleted (complete deletion), substituted and/or additional coding (and/or non-encoding) nucleotides/base pairs are inserted. It is to be understood that the term mutation also comprises mutations within the coding nucleotides/base pairs, mutations within the non-encoding nucleotides/base pairs such as within the regulatory nucleotides/base pairs and mutations within both the encoding nucleotides/base pairs and non-encoding nucleotides/base pairs. Further, the term mutation also comprises the inversion of nucleotides/base pairs (encoding and/or non-encoding) such as inversion of a part or all encoding nucleotides/base pairs or inversion of a part or all non-encoding nucleotides/base pairs or a combination thereof. Furthermore, the term mutation also comprises the relocation of nucleotides/base pairs (encoding and/or non-encoding) such as relocation of a part or all encoding nucleotides/base pairs or relocation of a part or all non-encoding nucleotides/base pairs or a combination thereof. As used herein, mutation may be a single mutation or several mutations, therefore, often the term "mutation(s)" used and relates to both a single mutation and several mutations. Said mutations may result in a modified expressed protein due to the change in the coding sequence. However, the term mutation is well known to the person skilled in the art and the person skilled in the art can generate mutations without further ado.

In embodiments of the invention, the inactivation of ORF 3b or ORF 3a and ORF 3b does not affect the expression of ORF 3c and/or not the activity of the E protein (encoded by ORF 3c). Thus, the ORF 3b or ORF 3a and ORF 3b expression (3b RNA or 3a and 3b RNA and/or 3b protein or 3a protein and 3b protein) and/or activity of the protein is reduced (or eliminated) whereas the expression of ORF 3c and/or the activity of the E protein is not affected. Thus, it is to be understood that deletions, truncations, substitutions, insertions, inversions, or relocations within the overlapping region of the Start codon (AUG) of the ORF 3c and the Stop (UAA) of the ORF 3b are encompassed as long as the expression of ORF 3c and/or the activity of the E protein is not affected.

In one aspect of the present invention said inactivation of ORF 3a or ORF 3a and ORF 3b does not affect the expression of ORF 3c and/or not the activity of the E protein. Thus, one embodiment of the present invention provides an IBV or an immunogenic composition comprising an IBV (infectious bronchitis virus), wherein:
the ORF 3a is inactivated; or
the ORF 3a and ORF 3b are inactivated; or
the ORF 3a and ORF 3b and the ORF 5a and ORF 5b are inactivated,
wherein said inactivation of ORF 3a or ORF 3a and ORF 3b does not affect the expression of ORF 3c and/or it does not affect the activity of the E protein.

In another aspect of the invention, the inactivation of ORF 3a or ORF 3a and ORF 3b does not affect the expression of ORF S and/or it does not affect the activity of the S protein as indicated by the protective immune response which is solely based on the S protein of IBV. Thus, the ORF 3a or ORF 3a and ORF 3b expression (3a RNA or 3a and 3b RNA and/or 3a protein or 3a protein and 3b protein) and/or the activity of the protein is reduced (or eliminated) whereas the expression of ORF S and/or the activity of the S protein is not affected. Preferably, the inactivation of ORF 3a or ORF 3a and ORF 3b leaves the termination codon (UAA) of the spike (S) protein intact which is overlapping with the start codon (AUG) of the ORF 3a. This may be done by not inactivating the A of the AUG of the start codon of the ORF 3a or by inactivating the ORF 3a and ORF 3b in a manner that the first nucleotide 3' of the last two nucleotides (UA) of the ORF S is an A or G for having a termination codon (UAA or UAG). Alternatively, a new stop codon in the ORF S may be generated by deletions, truncations, substitutions, insertions, inversions or relocations to read UAA, UAG or UGA (stop codon). Thus, it is to be understood that deletions, truncations, substitutions, insertions, inversions or relocations within the overlapping region of the Start codon (AUG) of the ORF 3a and the Stop (UAA) of the ORF S are encompassed as long as the expression and/or activity of ORF S is not affected.

In one aspect of the present invention said inactivation of ORF 3a or ORF 3a and ORF 3b does not affect the expression of ORF S and/or not the activity of the S protein. Thus, one embodiment of the present invention provides an IBV or an immunogenic composition comprising an IBV (infectious bronchitis virus), wherein:
the ORF 3a is inactivated; or
the ORF 3a and ORF 3b are inactivated; or
the ORF 3a and ORF 3b and the ORF 5a and ORF 5b are inactivated,
wherein said inactivation of ORF 3a or ORF 3a and ORF 3b does not affect the expression of ORF S and/or it does not affect the activity of the S protein.

In another aspect of the invention, the inactivation of ORF 5b or ORF 5a and ORF 5b does not affect the expression of ORF N and/or not the activity of the N protein (encoded by ORF N). Thus, the ORF 5b or ORF 5a and ORF 5b expression (5b RNA or 5a and 5b RNA and/or 5b protein or 5a protein and 5b protein) and/or the activity of the protein is reduced (or eliminated) whereas the expression of ORF N and/or the activity of the N protein is not affected. Preferably, the inactivation of ORF 5b or ORF 5a and ORF 5b leaves the start codon (AUG) of the N protein intact and therefore also the ORF N. However, it is to be understood that deletions, truncations, substitutions, insertions, inversions, or relocations within the overlapping region of the Start codon (AUG) of the ORF N and the Stop (UAG) of the ORF 5b are encompassed as long as the expression of ORF N and/or the activity of the N protein is not affected.

In one aspect of the present invention said inactivation of ORF 5b or ORF 5a and ORF 5b does not affect the expression of ORF N and/or not the activity of the N protein. Thus, one embodiment of the present invention provides an IBV or an immunogenic composition comprising an IBV (infectious bronchitis virus), wherein:

the ORF 5b is inactivated; or the ORF 5a and ORF 5b are inactivated; or the ORF 3a and ORF 3b and the ORF 5a and ORF 5b are inactivated wherein said inactivation of ORF 5b or ORF 5a and ORF 5b does not affect the expression of ORF N and/or it does not affect the activity of the N protein.

In one aspect of the present invention said inactivation is a complete or partial deletion of the ORF 3a and a partial deletion of ORF 3b and/or a complete or partial deletion of the ORF 5a and a partial deletion of ORF 5b, a complete or partial truncation of the ORF 3a and a partial truncation of ORF 3b and/or a complete or partial truncation of the ORF 5a and a partial truncation of ORF 5b, a complete or partial inversion of the ORF 3a and a partial inversion of ORF 3b and/or a complete or partial inversion the ORF 5a and a partial inversion of ORF 5b, a complete or partial relocation of the ORF 3a and a partial relocation of ORF 3b and/or a complete or partial relocation of the ORF 5a and a partial relocation of ORF 5b, an insertion of nucleic acids within the ORF 3a and ORF 3b and/or the ORF 5a and ORF 5b, a substitution of nucleic acids within the ORF 3a and ORF 3b and/or the ORF 5a and ORF 5b. Thus, one embodiment of the present invention provides an IBV or an immunogenic composition comprising an IBV (infectious bronchitis virus), wherein:

the ORF 3a and ORF 3b are inactivated; or the ORF 5a and ORF 5b are inactivated; or the ORF 3a and ORF 3b and the ORF 5a and ORF 5b are inactivated, wherein said inactivation is a complete or partial deletion of the ORF 3a and a partial deletion of ORF 3b and/or a complete or partial deletion of the ORF 5a and a partial deletion of ORF 5b, a complete or partial truncation of the ORF 3a and a partial truncation of ORF 3b and/or a complete or partial truncation of the ORF 5a and a partial truncation of ORF 5b, a complete or partial inversion of the ORF 3a and a partial inversion of ORF 3b and/or a complete or partial inversion the ORF 5a and a partial inversion of ORF 5b, a complete or partial relocation of the ORF 3a and a partial relocation of ORF 3b and/or a complete or partial relocation of the ORF 5a and a partial relocation of ORF 5b, an insertion of nucleic acids within the ORF 3a and ORF 3b and/or the ORF 5a and ORF 5b, a substitution of nucleic acids within the ORF 3a and ORF 3b and/or the ORF 5a and ORF 5b.

The term "inactivated" refers to either a reduced or eliminated expression of the protein (and/or RNA) and/or a reduced activity of the protein.

The term "inactivated" encompasses a reduced (or eliminated) expression of ORF 3a and/or ORF 3b (3a and/or 3b RNA and/or 3a protein and/or 3b protein) and/or ORF 5a and/or ORF 5b (5a and/or 5b RNA and/or 5a protein and/or 5b protein). It is to be understood that reduced expression encompasses both reduced RNA transcription as well as reduced protein expression. Preferably, the expression of ORF 3a and/or ORF 3b (3a and/or 3b RNA and/or 3a protein and/or 3b protein) and/or ORF 5a and/or ORF 5b (5a and/or 5b RNA and/or 5a protein and/or 5b protein) is reduced in the IBV of the present invention 5-10%, 10-20%, 20-30%, 30-40%, 40-50%, 50-60%, 60-70%, 70-80%, 80-90%, 90-95%, 95-99% or more by RNA and/or protein when compared to the expression of a wildtype IBV virus. More preferably, the expression of ORF 3a and/or ORF 3b (3a and/or 3b RNA and/or 3a protein and/or 3b protein) and/or ORF 5a and/or ORF 5b (5a and/or 5b RNA and/or 5a protein and/or 5b protein) is reduced in the IBV of the present invention 50-100%, 60-100%, 70-100% 80-100% or 90-100% by RNA and/or protein when compared to the expression of a wildtype IBV virus. Even more preferably, the expression of ORF 3a and/or ORF 3b (3a and/or 3b RNA and/or 3a protein and/or 3b protein) and/or ORF 5a and/or ORF 5b (5a and/or 5b RNA and/or 5a protein and/or 5b protein) is reduced in the IBV of the present invention 80%, 81%, 82%, 83%, 84%, 85%, 86%, 87%, 88%, 89%, 90%, 91%, 92%, 93%, 94%, 95%, 96%, 97%, 98%, 99% or 100% by RNA and/or protein when compared to the expression of a wildtype IBV virus.

In one aspect of the invention the expression of ORF 3a and/or ORF 3b (3a and/or 3b RNA and/or 3a protein and/or 3b protein) and/or ORF 5a and/or ORF 5b (5a and/or 5b RNA and/or 5a protein and/or 5b protein) is reduced in the IBV of the present invention approximately 1 to approximately 100 fold, approximately 5 to approximately 80 fold, approximately 20 to approximately 80 fold, approximately 1 to approximately 10 fold, or approximately 1 to approximately 5 fold, or approximately 40 to approximately 80 fold, or 1, 2, 3, 4, 5, 7, 10, 15, 20, 25, 30, 35, 40, 45, 50, 55, 60, 65, 70, 75, 80, 85, 90, 95 or 100 fold by RNA and/or protein when compared to the expression of a wildtype IBV virus.

The term "RNA" refers to any ribonucleic acid. The term encompasses single as well as double stranded RNA's. The RNA of the present invention encompasses isolated RNA (i.e. isolated from its natural context) and genetically modified forms. Moreover, comprised are also chemically modified RNA including naturally occurring modified RNA such as methylated RNA or artificial modified one such as biotinylated RNA. The terms "RNA" also specifically include RNA composed of bases other than the four biologically occurring nucleotides/bases (adenine, guanine, cytosine and uracil). The RNA of the present invention is characterized in that it shall encode a protein as referred to above (3a protein and/or 3b protein and/or 5a protein and/or 5b protein).

The term "nucleic acid" or "nucleic acid sequence" refers to polynucleotides including DNA molecules, RNA molecules, cDNA molecules or derivatives. The term encompasses single as well as double stranded polynucleotides. The nucleic acid of the present invention encompasses isolated polynucleotides (i.e. isolated from its natural context) and genetically modified forms. Moreover, comprised are also chemically modified polynucleotides including naturally occurring modified polynucleotides such as glycosylated or methylated polynucleotides or artificial modified one such as biotinylated polynucleotides. Further, the terms "nucleic acid" and "polynucleotide" are interchangeable and refer to any nucleic acid. The terms "nucleic acid" and "polynucleotide" also specifically include nucleic acids composed of bases other than the five biologically occurring bases (adenine, guanine, thymine, cytosine and uracil).

The term "protein", "amino acid" and "polypeptide" are used interchangeable. The term "protein" refers to a sequence of amino acids composed of the natural occurring amino acids as well as derivatives thereof. The naturally occurring amino acids are well known in the art and are described in standard text books of biochemistry. Within the amino acid sequence the amino acids are connected by peptide bonds. Further, the two ends of the amino acid sequence are referred to as the carboxyl terminus (C-terminus) and the amino terminus (N-terminus). The term "protein" encompasses essentially purified proteins or protein preparations comprising other proteins in addition. Further, the term also relates to protein fragments. Moreover, it includes chemically modified proteins. Such modifications may be artificial modifications or naturally occurring modifications such as phosphorylation, glycosylation, myristylation and the like.

Methods for measuring the reduced expression of ORF 3a and/or ORF 3b (3a and/or 3b RNA and/or 3a protein and/or 3b protein) and/or ORF 5a and/or ORF 5b (5a and/or 5b RNA and/or 5a protein and/or 5b protein) are well known to the person skilled in the art. Such methods include but are not limited to RT-PCR, Real Time RT-PCR, Northern blots, Western blots, radioimmunoassay, ELISA, immunofluorescence, immunohistochemistry, in situ hybridization.

However, the term "inactivated" also encompasses a reduced (or eliminated) activity of the protein (3a protein and/or 3b protein and/or 5a protein and/or 5b protein). Preferably, the activity of the protein (3a protein and/or 3b protein and/or 5a protein and/or 5b protein) of the IBV of the present invention is reduced 5-10%, 10-20%, 20-30%, 30-40%, 40-50%, 50-60%, 60-70%, 70-80%, 80-90%, 90-95%, 95-99% when compared to the activity of the protein (3a protein and/or 3b protein and/or 5a protein and/or 5b protein) of a wildtype IBV virus. More preferably, the activity of the protein (3a protein and/or 3b protein and/or 5a protein and/or 5b protein) of the IBV of the present invention is reduced 50-100%, 60-100%, 70-100% 80-100% or 90-100% when compared to the activity of the protein (3a protein and/or 3b protein and/or 5a protein and/or 5b protein) of a wildtype IBV virus. Even more preferably, the activity of the protein (3a protein and/or 3b protein and/or 5a protein and/or 5b protein) of the IBV of the present invention is reduced 80%, 81%, 82%, 83%, 84%, 85%, 86%, 87%, 88%, 89%, 90%, 91%, 92%, 93%, 94%, 95%, 96%, 97%, 98%, 99% or 100% when compared to the activity of the protein (3a protein and/or 3b protein and/or 5a protein and/or 5b protein) of a wildtype IBV virus.

Preferably, the activity of the protein (3a protein and/or 3b protein and/or 5a protein and/or 5b protein) of the IBV of the present invention is reduced approximately 1 to approximately 100 fold, approximately 5 to approximately 80 fold, approximately 20 to approximately 80 fold, approximately 1 to approximately 10 fold, or approximately 1 to approximately 5 fold, or approximately 40 to approximately 80 fold, or 1, 2, 3, 4, 5, 7, 10, 15, 20, 25, 30, 35, 40, 45, 50, 55, 60, 65, 70, 75, 80, 85, 90, 95 or 100 when compared to the activity of the protein (3a protein and/or 3b protein and/or 5a protein and/or 5b protein) of a wildtype IBV virus.

The accessory IBV proteins 3a and 3b were recently found to cause a delayed activation of the type I interferon response in vitro, with protein 3a additionally being involved in resistance of IBV to the cellular antiviral state induced by IFN (Kint et al 2015: J. Virol. 89:1156-1167; Kint et al 2015: J. Virol. doi: JVI.01057-15.). Accessory protein 5b contributes to host cell shut off, hereby amongst others inhibiting the translation of type I IFN (Kint, PhD thesis 2015).

The term "inactivated" encompasses a recombinant IBV having a reduced or inhibited cellular interferon immune response (IBV which is not able to fully interfere with the cellular interferon immune response). In one aspect, the recombinant IBV has a reduced or inhibited interference with the interferon expression and/or activity. Preferably, the expression and/or activity of one or two types of interferon (IFN) is reduced or inhibited. In another aspect of the present invention, the recombinant IBV causes an effect on the expression and/or activity of IFN-[alpha]. In another aspect, the expression and/or activity of IFN-[beta] is affected. In another aspect, the expression and/or activity of IFN-[gamma] is affected. Preferably, the expression and/or activity of IFN-[alpha] and/or IFN-[beta] and/or IFN-[gamma] is reduced 5-10%, 10-20%, 20-30%, 30-40%, 40-50%, 50-60%, 60-70%, 70-80%, 80-90% or more by protein, polypeptide, etc. with an interferon antagonist activity when compared to a control (e.g., PBS or a protein without interferon antagonist activity) in IFN-competent systems, e.g., a wild-type cell or animal under the same conditions. More preferably, the expression and/or activity of IFN-[alpha] and/or IFN-[beta] and/or IFN-[gamma] is reduced approximately 1 to approximately 100 fold, approximately 5 to approximately 80 fold, approximately 20 to approximately 80 fold, approximately 1 to approximately 10 fold, or approximately 1 to approximately 5 fold, or approximately 40 to approximately 80 fold, or 1, 2, 3, 4, 5, 7, 10, 15, 20, 25, 30, 35, 40, 45, 50, 55, 60, 65, 70, 75, 80, 85, 90, 95 or 100 fold by protein, polypeptide, etc. with an interferon antagonist activity when compared to a control (e.g., PBS or a protein without interferon antagonist activity) in IFN-competent systems under the same conditions. Methods for measuring the reduced or inhibited interferon expression and/or activity are well known to the person skilled in the art.

In one aspect of the present invention the ORF 3a is complete or partially deleted, substituted or inverted and wherein the ORF 3b is partially deleted, substituted or inverted. Thus, one embodiment of the present invention provides an IBV or an immunogenic composition comprising an IBV (infectious bronchitis virus), wherein:

the ORF 3a and ORF 3b are inactivated; or the ORF 3a and ORF 3b and the ORF 5a and ORF 5b are inactivated;

wherein the ORF 3a is complete or partially deleted, substituted or inverted and wherein the ORF 3b is partially deleted, substituted or inverted.

In one aspect of the present invention the ORF 5a is complete or partially deleted, substituted or inverted and wherein the ORF 5b is partially deleted, substituted or inverted. Thus, one embodiment of the present invention provides an IBV or an immunogenic composition comprising an IBV (infectious bronchitis virus), wherein:

the ORF 5a and ORF 5b are inactivated; or the ORF 3a and ORF 3b and the ORF 5a and ORF 5b are inactivated, wherein the ORF 5a is complete or partially deleted, substituted or inverted and wherein the ORF 5b is partially deleted, substituted or inverted.

In one aspect of the present invention the ORF 3a and the ORF 5a are complete or partially deleted, substituted or inverted and wherein the ORF 3b and the ORF 5b are partially deleted, substituted or inverted. Thus, one embodiment of the present invention provides an IBV or an immunogenic composition comprising an IBV (infectious bronchitis virus), wherein:

the ORF 3a and ORF 3b and the ORF 5a and ORF 5b are inactivated, wherein the ORF 3a and the ORF 5a are complete or partially deleted, substituted or inverted and wherein the ORF 3b and the ORF 5b are partially deleted, substituted or inverted.

The term "complete or partially deleted, substituted or inverted" encompasses a complete or partial deletion, a complete or partial substitution and a complete or partial inversion. The term "complete" means that the whole ORF is affected from the start codon to the stop of the ORF. Preferably, the ORF 3a and/or ORF 5a is complete deleted, substituted or inverted. However, the term "partial" means that only a part of the whole ORF is affected. Preferably, ORF 3a, ORF 3b, ORF 5a, ORF 5b is partially deleted, substituted or inverted. More preferably, ORF 3b and/or ORF 5b is partially deleted, substituted or inverted. Most preferably, the ORF 3b and/or ORF 5b are partially deleted for not affecting the expression of the ORF 3c (encoding for the E protein) and ORF N (encoding the N protein) and/or the activity of the E protein and N protein.

In one aspect of the present invention the ORF 3a is complete or partially deleted and the ORF 3b is partially deleted. Thus, one embodiment of the present invention provides an IBV or an immunogenic composition comprising an IBV (infectious bronchitis virus), wherein:
the ORF 3a and ORF 3b are inactivated; or
the ORF 3a and ORF 3b and the ORF 5a and ORF 5b are inactivated,
wherein the ORF 3a is complete or partially deleted and the ORF 3b is partially deleted.

In one aspect of the present invention the ORF 5a is complete or partially deleted and the ORF 5b is partially deleted. Thus, one embodiment of the present invention provides an IBV or an immunogenic composition comprising an IBV (infectious bronchitis virus), wherein:
the ORF 5a and ORF 5b are inactivated; or
the ORF 3a and ORF 3b and the ORF 5a and ORF 5b are inactivated,
wherein the ORF 5a is complete or partially deleted and the ORF 5b is partially deleted.

In one aspect of the present invention the ORF 3a and the ORF 5a are complete or partially deleted and the ORF 3b and the ORF 5b are partially deleted. Thus, one embodiment of the present invention provides an IBV or an immunogenic composition comprising an IBV (infectious bronchitis virus), wherein:
the ORF 3a and ORF 3b and the ORF 5a and ORF 5b are inactivated,
wherein the ORF 3a and the ORF 5a are complete or partially deleted and the ORF 3b and the ORF 5b are partially deleted.

In one aspect of the present invention the start codon of ORF 3a and/or ORF 3b and/or ORF 5a and/or ORF 5b is inactivated. Thus, one embodiment of the present invention provides an IBV or an immunogenic composition comprising an IBV (infectious bronchitis virus), wherein:
the ORF 3a; and/or
the ORF 3b; and/or
the ORF 5a; and/or
the ORF 5b is inactivated,
wherein the start codon of ORF 3a and/or ORF 3b and/or ORF 5a and/or ORF 5b is inactivated.

In one aspect of the present invention the start codon of ORF 3a and the start codon of ORF 3b are inactivated. Thus, one embodiment of the present invention provides an IBV or an immunogenic composition comprising an IBV (infectious bronchitis virus), wherein:
the ORF 3a and ORF 3b are inactivated; or
the ORF 3a and ORF 3b and the ORF 5a and ORF 5b are inactivated,
wherein the start codon of ORF 3a and the start codon of ORF 3b are inactivated.

In one aspect of the present invention the start codon of ORF 3a (AUG, nucleotides 1-3 of SEQ ID NO:1) and the start codon of ORF 3b (AUG, nucleotides 174-176 of SEQ ID NO:1) are inactivated. Thus, it has to be understood that the inactivation of the AUG encompasses the inactivation/mutation of 1, 2, or 3 nucleotide(s) within the AUG. Therefore, inactivation of the start codon AUG encompasses the mutation of the A and/or mutation of the U and/or mutation of the G. Thus, one embodiment of the present invention provides an IBV or an immunogenic composition comprising an IBV (infectious bronchitis virus), wherein:
the ORF 3a and ORF 3b are inactivated; or
the ORF 3a and ORF 3b and the ORF 5a and ORF 5b are inactivated,
wherein the start codon of ORF 3a (AUG, nucleotides 1-3 of SEQ ID NO:1) and the start codon of ORF 3b (AUG, nucleotides 174-176 of SEQ ID NO:1) are inactivated.

In one aspect of the present invention said inactivation of the start codon (AUG) of ORF 3a and ORF 3b is a deletion, substitution or inversion. Thus, one embodiment of the present invention provides an IBV or an immunogenic composition comprising an IBV (infectious bronchitis virus), wherein:
the ORF 3a and ORF 3b are inactivated; or
the ORF 3a and ORF 3b and the ORF 5a and ORF 5b are inactivated,
wherein the start codon of ORF 3a (AUG, nucleotide 1-3 of SEQ ID NO:1) and the start codon of ORF 3b (AUG, nucleotides 174-176 of SEQ ID NO:1) are inactivated by a deletion, substitution or inversion.

In one aspect of the present invention the start codon of ORF 5a and the start codon of ORF 5b are inactivated. Thus, one embodiment of the present invention provides an IBV or an immunogenic composition comprising an IBV (infectious bronchitis virus), wherein:
the ORF 5a and ORF 5b are inactivated; or
the ORF 3a and ORF 3b and the ORF 5a and ORF 5b are inactivated,
wherein the start codon of ORF 5a and the start codon of ORF 5b are inactivated.

In one aspect of the present invention the start codon of ORF 5a (AUG, nucleotides 1-3 of SEQ ID NO:2) and the start codon (AUG, nucleotides 195-197 of SEQ ID NO:2) of ORF 5b are inactivated. Thus, it has to be understood that the inactivation of the AUG encompasses the inactivation/mutation of 1, 2, or 3 nucleotide(s) within the AUG. Therefore, inactivation of the start codon AUG encompasses the mutation of the A and/or mutation of the U and/or mutation of the G. Thus, one embodiment of the present invention provides an IBV or an immunogenic composition comprising an IBV (infectious bronchitis virus), wherein:
the ORF 5a and ORF 5b are inactivated; or
the ORF 3a and ORF 3b and the ORF 5a and ORF 5b are inactivated,
wherein the start codon of ORF 5a (AUG, nucleotides 1-3 of SEQ ID NO:2) and the start codon of ORF 5b (AUG, nucleotides 195-197 of SEQ ID NO:2) are inactivated.

In one aspect of the present invention said inactivation of the start codon (AUG) of ORF 5a and ORF 5b is a deletion, substitution, or inversion. Thus, one embodiment of the present invention provides an IBV or an immunogenic composition comprising an IBV (infectious bronchitis virus), wherein:
the ORF 5a and ORF 5b are inactivated; or
the ORF 3a and ORF 3b and the ORF 5a and ORF 5b are inactivated,
wherein the start codon of ORF 5a (AUG, nucleotides 1-3 of SEQ ID NO:2) and the start codon of ORF 5b (AUG, nucleotides 195-197 of SEQ ID NO:2) are inactivated by a deletion, substitution or inversion.

In one aspect of the present invention the ORF 3a and ORF 3b are truncated from the 5'-Terminus of the start codon (AUG, nucleotides 1-3 of SEQ ID NO:1) of ORF 3a and ORF 3b (AUG, nucleotides 174-176 of SEQ ID NO:1). Thus, one embodiment of the present invention provides an IBV or an immunogenic composition comprising an IBV (infectious bronchitis virus), wherein:
    the ORF 3a and ORF 3b are inactivated; or
    the ORF 3a and ORF 3b and the ORF 5a and ORF 5b are inactivated,
wherein the ORF 3a and ORF 3b are truncated from the 5'-Terminus of the start codon (AUG, nucleotides 1-3 of SEQ ID NO:1) of ORF 3a and ORF 3b (AUG, nucleotides 174-176 of SEQ ID NO:1).

The term "truncated from the 5'-Terminus of the start codon" refers to the truncation of the ORF at the 5'-Terminus. The term "5'-Terminus" already has been described elsewhere. The term "truncated or truncation" refers to the deletion of one or more nucleotides/bases within the ORF. Thus, portions of the 3'-Terminus of the ORF are retained whereas portions of the 5'-Terminus region of the ORF are deleted. However, the truncation at the 5'-Terminus may result in the deletion of one or more amino acids within the corresponding protein or in a frameshift in the ORF which results in a coding region which is different from the protein of the wildtype. However, the truncation at the 5'-Terminus may result in the expression of no protein at all as the start codon is truncated.

The term "5'-Terminus of the start codon" as used herein is to be understood that said truncation affects (includes) the start codon of the ORF. The 5'-terminus of the start codon (AUG) is the A, whereas the 3' Terminus of the AUG is the G. However, the terms "5'-" and "3-" are well known to the person skilled in the art.

In one aspect of the present invention the ORF 3a and ORF 3b are truncated from the A, U, or G of the start codon (AUG, nucleotides 1-3 of SEQ ID NO:1) of ORF 3a and ORF 3b (AUG, nucleotides 174-176 of SEQ ID NO:1). Thus, one embodiment of the present invention provides an IBV or an immunogenic composition comprising an IBV (infectious bronchitis virus), wherein:
    the ORF 3a and ORF 3b are inactivated; or
    the ORF 3a and ORF 3b and the ORF 5a and ORF 5b are inactivated,
wherein invention the ORF 3a and ORF 3b are truncated from the A, U, or G of the start codon (AUG, nucleotides 1-3 of SEQ ID NO:1) of ORF 3a and ORF 3b (AUG, nucleotides 174-176 of SEQ ID NO:1).

The term "truncated from the A, U or G of the start codon" as used herein is to be understood that said truncation may start with the A or U or G. In case the truncation starts with the A, the A is truncated. However, if the truncation from the A comprises the deletion of two or more nucleotides, the U is deleted as well. Further, if the truncation from the A comprises the deletion of three or more nucleotides the A, U, and G is deleted. However, it is to be understood that if the truncation starts with the U, the U is deleted, whereas the A of AUG still remains. Further, if the truncation starts with the G, the G is deleted, whereas the A and U of AUG still remain.

In one aspect of the present invention the ORF 5a and ORF 5b are truncated from the 5'-Terminus of the start codon of ORF 5a (AUG, nucleotides 1-3 of SEQ ID NO:2) and ORF 5b (AUG, nucleotides 195-197 of SEQ ID NO:2). Thus, one embodiment of the present invention provides an IBV or an immunogenic composition comprising an IBV (infectious bronchitis virus), wherein:
    the ORF 5a and ORF 5b are inactivated; or
    the ORF 3a and ORF 3b and the ORF 5a and ORF 5b are inactivated,
wherein the ORF 5a and ORF 5b are truncated from the 5'-Terminus of the start codon of ORF 5a (AUG, nucleotides 1-3 of SEQ ID NO:2) and ORF 5b (AUG, nucleotides 195-197 of SEQ ID NO:2).

In one aspect of the present invention the ORF 5a and ORF 5b are truncated from the A, U, or G of the start codon of ORF 5a (AUG, nucleotides 1-3 of SEQ ID NO:2) and ORF 5b (AUG, nucleotides 195-197 of SEQ ID NO:2). Thus, one embodiment of the present invention provides an IBV or an immunogenic composition comprising an IBV (infectious bronchitis virus), wherein:
    the ORF 5a and ORF 5b are inactivated; or
    the ORF 3a and ORF 3b and the ORF 5a and ORF 5b are inactivated,
wherein the ORF 5a and ORF 5b are truncated from the A, U, or G of the start codon of ORF 5a (AUG, nucleotides 1-3 of SEQ ID NO:2) and ORF 5b (AUG, nucleotides 195-197 of SEQ ID NO:2).

In one aspect of the present invention the ORF 3a and ORF 3b are truncated from the 5'-Terminus of the start codon (AUG) of ORF 3a (AUG, nucleotides 1-3 of SEQ ID NO:1) and the start codon of ORF 3b (AUG, nucleotides 174-176 of SEQ ID NO:1) and wherein the ORF 5a and ORF 5b are truncated from the 5'-Terminus of the start codon of ORF 5a (AUG, nucleotides 1-3 of SEQ ID NO:2) and the start codon ORF 5b (AUG, nucleotides 195-197 of SEQ ID NO:2). Thus, one embodiment of the present invention provides an IBV or an immunogenic composition comprising an IBV (infectious bronchitis virus), wherein:
    ORF 3a and ORF 3b and the ORF 5a and ORF 5b are inactivated,
wherein the ORF 3a and ORF 3b are truncated from the 5'-Terminus of the start codon (AUG) of ORF 3a (AUG, nucleotides 1-3 of SEQ ID NO:1) and the start codon of ORF 3b (AUG, nucleotides 174-176 of SEQ ID NO:1) and wherein the ORF 5a and ORF 5b are truncated from the 5'-Terminus of the start codon of ORF 5a (AUG, nucleotides 1-3 of SEQ ID NO:2) and the start codon ORF 5b (AUG, nucleotides 195-197 of SEQ ID NO:2).

In one aspect of the present invention at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides from the 5'-Terminus of the start codon (AUG, nucleotides 1-3 of SEQ ID NO:1) of the ORF 3a are deleted, substituted or inverted, and, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides from the 5'-Terminus of the start codon (AUG, nucleotides 174-176 of SEQ ID NO:1) of the ORF 3b are deleted, substituted or inverted. Thus, one embodiment of the present invention provides an IBV or an immunogenic composition comprising an IBV (infectious bronchitis virus), wherein:
    the ORF 3a and ORF 3b are inactivated; or
    the ORF 3a and ORF 3b and the ORF 5a and ORF 5b are inactivated,
wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides from the 5'-Terminus of the start codon (AUG, nucleotides 1-3 of SEQ ID NO:1) of the ORF 3a are deleted, substituted or inverted, and, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides from the 5'-Terminus of the start codon (AUG, nucleotides 174-176 of SEQ ID NO:1) of the ORF 3b are deleted, substituted or inverted.

In one aspect of the present invention at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides from the A, U, or G of the start codon (AUG, nucleotides 1-3 of SEQ ID NO:1) of the ORF 3a are deleted, substituted or inverted, and, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides from the A, U, or G of the start codon (AUG, nucleotides 174-176 of SEQ ID NO:1) of the ORF 3b are deleted, substituted or inverted. Thus, one embodiment of the present invention provides an IBV or an immunogenic composition comprising an IBV (infectious bronchitis virus), wherein:

the ORF 3a and ORF 3b are inactivated; or the ORF 3a and ORF 3b and the ORF 5a and ORF 5b are inactivated, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides from the A, U, or G of the start codon (AUG, nucleotides 1-3 of SEQ ID NO:1) of the ORF 3a are deleted, substituted or inverted, and, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides from the A, U, or G of the start codon (AUG, nucleotides 174-176 of SEQ ID NO:1) of the ORF 3b are deleted, substituted or inverted.

In one aspect of the present invention at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides from the 5'-Terminus of the start codon (AUG, nucleotides 1-3 of SEQ ID NO:2) of the ORF 5a are deleted, substituted or inverted and, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 170 nucleotides, at least 190 nucleotides from the 5'-Terminus of the start codon (AUG, nucleotide 195-197 of SEQ ID NO:2) of the ORF 5b are deleted, substituted or inverted. Thus, one embodiment of the present invention provides an IBV or an immunogenic composition comprising an IBV (infectious bronchitis virus), wherein:

the ORF 5a and ORF 5b are inactivated; or the ORF 3a and ORF 3b and the ORF 5a and ORF 5b are inactivated, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides from the 5'-Terminus of the start codon (AUG, nucleotides 1-3 of SEQ ID NO:2) of the ORF 5a are deleted, substituted or inverted and, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides from the 5'-Terminus of the start codon (AUG, nucleotides 195-197 of SEQ ID NO:2) of the ORF 5b are deleted, substituted or inverted.

In one aspect of the present invention at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides from the A, U, or G of the start codon (AUG, nucleotides 1-3 of SEQ ID NO:2) of the ORF 5a are deleted, substituted or inverted and, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides from the A, U, or G of the start codon (AUG, nucleotides 195-197 of SEQ ID NO:2) of the ORF 5b are deleted, substituted or inverted.

In one aspect of the present invention between 1 and 173 nucleotides from the 5'-Terminus of the start codon (AUG, nucleotides 1-3 of SEQ ID NO:1) of the ORF 3a are deleted, substituted or inverted and wherein between 1 and 175 nucleotides from the 5'-Terminus of the start codon (AUG, nucleotides 174-176 of SEQ ID NO:1) of the ORF 3b are deleted, substituted or inverted. Thus, one embodiment of the present invention provides an IBV or an immunogenic composition comprising an IBV (infectious bronchitis virus), wherein:

the ORF 3a and ORF 3b are inactivated; or the ORF 3a and ORF 3b and the ORF 5a and ORF 5b are inactivated, wherein between 1 and 173 nucleotides from the 5'-Terminus of the start codon (AUG, nucleotide 1-3 SEQ ID NO:1) of the ORF 3a are deleted, substituted or inverted and wherein between 1 and 175 nucleotides from the 5'-Terminus of the start codon (AUG, nucleotides 174-176 of SEQ ID NO:1) of the ORF 3b are deleted, substituted or inverted.

The term "between 1 and 173 nucleotides from the 5'-Terminus of the start codon of the ORF 3a are deleted, substituted or inverted" refers to a deletion, substitution, or inversion of nucleotides of the ORF 3a from the 5'-Terminus, wherein the 5'-Terminal nucleotide (the A of AUG; nucleotides 1-3 of SEQ ID NO:1) is number 1. Thus, said term encompasses deletions, substitutions or inversions from the 5'-Terminus of nucleotides 1 to 173, 1 to 172, 1 to 171, 1 to 170, 1 to 169 and so forth until 1 to 5, 1 to 4, 1 to 3, 1 to 2 and 1 to 1. Thus, it is to be understood that the term "between 1 and 173 nucleotides from the 5'-Terminus of the start codon of the ORF 3a are deleted, substituted or inverted" encompasses 173 variants, wherein in all 173 variants the 5'-Terminal nucleotide (the A of AUG is defined as number 1) is deleted, substituted or inverted.

The term "between 1 and 175 nucleotides from the 5'-Terminus of the start codon of the ORF 3b are deleted, substituted or inverted" refers to a deletion, substitution or inversion of nucleotides of the ORF 3b from the 5'-Terminus, wherein the 5'-Terminal nucleotide (the A of AUG; nucleotides 174-176 of SEQ ID NO:1) is number 1. Thus, said term encompasses deletions, substitutions or inversions from the 5'-Terminus of nucleotides 1 to 175, 1 to 174, 1 to 173, 1 to 172, 1 to 170 and so forth until 1 to 5, 1 to 4, 1 to 3, 1 to 2 and 1 to 1. Thus, it is to be understood that the term "between 1 and 175 nucleotides from the 5'-Terminus of the start codon of the ORF 3b are deleted, substituted or inverted" encompasses 175 variants, wherein in all 175 variants the 5'-Terminal nucleotide (the A of AUG is defined as number 1) is deleted, substituted or inverted.

In one aspect, the IBV of the present invention comprises a deletion, substitution or inversion from the 5'-Terminus of the ORF 3a of nucleotides 1-10, nucleotides 1-20, nucleotides 1-30, nucleotides 1-40, nucleotides 1-50, nucleotides 1-60, nucleotides 1-70, nucleotides 1-80, nucleotides 1-90, nucleotides 1-100, nucleotides 1-110, nucleotides 1-120, nucleotides 1-130, nucleotides 1-140, nucleotides 1-150, nucleotides 1-160, nucleotides 1-170, nucleotides 1-173, wherein the 5'-Terminal nucleotide (the A of AUG; nucleotide 1 of SEQ ID NO:1) is number 1, and, preferably, the IBV of the present invention comprises a deletion, substitution or inversion from the 5'-Terminus of the ORF 3b of nucleotides 1-10, nucleotides 1-20, nucleotides 1-30, nucleotides 1-40, nucleotides 1-50, nucleotides 1-60, nucleotides 1-70, nucleotides 1-80, nucleotides 1-90, nucleotides 1-100, nucleotides 1-110, nucleotides 1-120, nucleotides 1-130, nucleotides 1-140, nucleotides 1-150, nucleotides 1-160, nucleotides 1-170, nucleotides 1-175, wherein the 5'-Terminal nucleotide (the A of AUG; nucleotides 174 of SEQ ID NO:1) is number 1.

In one aspect of the present invention between 1 and 173 nucleotides from the A of the start codon (A of AUG, nucleotide 1 of SEQ ID NO:1) or between 1 and 172 nucleotides from the U of the start codon (U of AUG, nucleotide 2 of SEQ ID NO:1) or between 1 and 171 nucleotides from the G of the start codon (G of AUG, nucleotide 3 of SEQ ID NO:1) of the ORF 3a are deleted, substituted or inverted and wherein between 1 and 175 nucleotides from the A of the start codon (A of AUG, nucleotide 174 of SEQ ID NO:1) or between 1 and 174 nucleotides from the U of the start codon (U of AUG, nucleotide 175 of SEQ ID NO:1) or between 1 and 173 nucleotides from the G of the start codon (G of AUG, nucleotide 176 of SEQ ID NO:1) of the ORF 3b are deleted, substituted or inverted. Thus, one embodiment of the present invention provides an IBV or an immunogenic composition comprising an IBV (infectious bronchitis virus), wherein:

the ORF 3a and ORF 3b are inactivated; or
the ORF 3a and ORF 3b and the ORF 5a and ORF 5b are inactivated,
wherein between 1 and 173 nucleotides from the A of the start codon (A of AUG, nucleotide 1 of SEQ ID NO:1) or between 1 and 172 nucleotides from the U of the start codon (U of AUG, nucleotide 2 of SEQ ID NO:1) or between 1 and 171 nucleotides from the G of the start codon (G of AUG, nucleotide 3 of SEQ ID NO:1) of the ORF 3a are deleted, substituted or inverted and wherein between 1 and 175 nucleotides from the A of the start codon (A of AUG, nucleotide 174 of SEQ ID NO:1) or between 1 and 174 nucleotides from the U of the start codon (U of AUG, nucleotide 175 of SEQ ID NO:1) or between 1 and 173 nucleotides from the G of the start codon (G of AUG, nucleotide 176 of SEQ ID NO:1) of the ORF 3b are deleted, substituted or inverted.

The terms "between 1 and 171 nucleotides", "between 1 and 172 nucleotides", "between 1 and 173 nucleotides", between 1 and 174 nucleotides" and between "1 and 175 nucleotides" have to be understood according to the other definitions as set forth above. Thus, said terms encompass 171 variants, 172 variants, 173 variants, 174 variants or 175 variants. The terms "from the A of the start codon", "from the U of the start codon" or "from the G of the start codon" define the starting points of the deletion, substitution or inversion. The term "from the A of the start codon" exemplary defines that the deletion, substitution or inversion starts from the A of the start codon (AUG) and affects the A.

Preferably, the IBV of one aspect of the present invention comprises a deletion, substitution or inversion from the A, U or G of the start codon (AUG) of the ORF 3a and ORF 3b of nucleotides 1-10, nucleotides 1-20, nucleotides 1-30, nucleotides 1-40, nucleotides 1-50, nucleotides 1-60, nucleotides 1-70, nucleotides 1-80, nucleotides 1-90, nucleotides 1-100, nucleotides 1-110, nucleotides 1-120, nucleotides 1-130, nucleotides 1-140, nucleotides 1-150, nucleotides 1-160, nucleotides 1-170.

In another aspect of the present invention between 1 and 194 nucleotides from the 5'-Terminus of the start codon (AUG, nucleotides 1-3 of SEQ ID NO:2) of the ORF 5a are deleted, substituted or inverted and wherein between 1 and 191 nucleotides from the 5'-Terminus of the start codon (AUG, nucleotides 195-197 of SEQ ID NO:2) of the ORF 5b are deleted, substituted or inverted. Thus, one embodiment of the present invention provides an IBV or an immunogenic composition comprising an IBV (infectious bronchitis virus), wherein:

the ORF 5a and ORF 5b are inactivated; or
the ORF 3a and ORF 3b and the ORF 5a and ORF 5b are inactivated,
wherein between 1 and 194 nucleotides from the 5'-Terminus of the start codon (AUG, nucleotides 1-3 of SEQ ID NO:2) of the ORF 5a are deleted, substituted or inverted and wherein between 1 and 191 nucleotides from the 5'-Terminus of the start codon (AUG, nucleotides 195-197 of SEQ ID NO:2) of the ORF 5b are deleted, substituted or inverted.

The term "between 1 and 194 nucleotides from the 5'-Terminus of the start codon of the ORF 5a are deleted, substituted, or inverted" refers to a deletion, substitution or inversion of nucleotides of the ORF 5a from the 5'-Terminus, wherein the 5'-Terminal nucleotide (the A of AUG; nucleotides 1-3 of SEQ ID NO:2) is number 1. Thus, said term encompasses deletions, substitutions or inversions from the 5'-Terminus of nucleotides 1 to 194, 1 to 193, 1 to 192, 1 to 191, 1 to 190 and so forth until 1 to 5, 1 to 4, 1 to 3, 1 to 2 and 1 to 1. Thus, it is to be understood that the term "between 1 and 194 nucleotides from the 5'-Terminus of the start codon of the ORF 5a are deleted, substituted or inverted" encompasses 194 variants, wherein in all 194 variants the 5'-Terminal nucleotide (the A of AUG is defined as number 1) is deleted, substituted or inverted.

The term "between 1 and 191 nucleotides from the 5'-Terminus of the start codon of the ORF 5b are deleted, substituted or inverted" refers to a deletion, substitution or inversion of nucleotides of the ORF 5b from the 5'-Terminus, wherein the 5'-Terminal nucleotide (the A of AUG, nucleotides 195-197 of SEQ ID NO:2) is number 1. Thus, said term encompasses deletions, substitutions or inversions from the 5'-Terminus of nucleotides 1 to 191, 1 to 190, 1 to 189, 1 to 188, 1 to 187 and so forth until 1 to 5, 1 to 4, 1 to 3, 1 to 2 and 1 to 1. Thus, it is to be understood that the term "between 1 and 191 nucleotides from the 5'-Terminus of the start codon of the ORF 5b are deleted, substituted or inverted" encompasses 191 variants, wherein in all 191 variants the 5'-Terminal nucleotide (the A of AUG is defined as number 1) is deleted, substituted or inverted.

Preferably, the IBV of the present invention comprises a deletion, substitution or inversion from the 5'-Terminus of the ORF 5a of nucleotides 1-10, nucleotides 1-20, nucleotides 1-30, nucleotides 1-40, nucleotides 1-50, nucleotides 1-60, nucleotides 1-70, nucleotides 1-80, nucleotides 1-90, nucleotides 1-100, nucleotides 1-110, nucleotides 1-120, nucleotides 1-130, nucleotides 1-140, nucleotides 1-150, nucleotides 1-160, nucleotides 1-170, nucleotides 1-180, nucleotides 1-190, nucleotides 1-194, wherein the 5'-Terminal nucleotide (the A of AUG, nucleotide 1 of SEQ ID NO:2) is number 1, and, preferably, the IBV of the present invention comprises a deletion, substitution or inversion from the 5'-Terminus of the ORF 5b of nucleotides 1-10, nucleotides 1-20, nucleotides 1-30, nucleotides 1-40, nucleotides 1-50, nucleotides 1-60, nucleotides 1-70, nucleotides 1-80, nucleotides 1-90, nucleotides 1-100, nucleotides 1-110, nucleotides 1-120, nucleotides 1-130, nucleotides 1-140, nucleotides 1-150, nucleotides 1-160, nucleotides 1-170, nucleotides 1-180, nucleotides 1-190, nucleotides 1-191, wherein the 5'-Terminal nucleotide (the A of AUG, nucleotide 195 of SEQ ID NO:2) is number 1.

In one aspect of the present invention between 1 and 194 nucleotides from the A of the start codon (A of AUG, nucleotide 1 of SEQ ID NO:2) or between 1 and 193 nucleotides from the U of the start codon (U of AUG, nucleotide 2 of SEQ ID NO:2) or between 1 and 192 nucleotides from the G of the start codon (G of AUG, nucleotide 3 of SEQ ID NO:2) of the ORF 5a are deleted, substituted or inverted and wherein between 1 and 191 nucleotides from the A of the start codon (A of AUG, nucleotide 195 of SEQ ID NO:2) or between 1 and 190 nucleotides from the U of the start codon (U of AUG, nucleotide 196 of SEQ ID NO:2) or between 1 and 189 nucleotides from the G of the start codon (G of AUG, nucleotide 197 of SEQ ID NO:2) of the ORF 5b are deleted, substituted or inverted. Thus, one embodiment of the present invention provides an IBV or an immunogenic composition comprising an IBV (infectious bronchitis virus), wherein:
  the ORF 5a and ORF 5b are inactivated; or
  the ORF 3a and ORF 3b and the ORF 5a and ORF 5b are inactivated,
wherein between 1 and 194 nucleotides from the A of the start codon (A of AUG, nucleotide 1 of SEQ ID NO:2) or between 1 and 193 nucleotides from the U of the start codon (U of AUG, nucleotide 2 of SEQ ID NO:2) or between 1 and 192 nucleotides from the G of the start codon (G of AUG, nucleotide 3 of SEQ ID NO:2) of the ORF 5a are deleted, substituted or inverted and wherein between 1 and 191 nucleotides from the A of the start codon (A of AUG, nucleotide 195 of SEQ ID NO:2) or between 1 and 190 nucleotides from the U of the start codon (U of AUG, nucleotide 196 of SEQ ID NO:2) or between 1 and 189 nucleotides from the G of the start codon (G of AUG, nucleotide 197 of SEQ ID NO:2) of the ORF 5b are deleted, substituted or inverted.

The terms "between 1 and 189 nucleotides", "between 1 and 190 nucleotides", "between 1 and 191 nucleotides", "between 1 and 192 nucleotides", "between 1 and 193 nucleotides", between 1 and 194 nucleotides" have to be understood according to the other definitions as set forth above. Said terms encompass 189 variants, 190 variants, 191 variants, 192 variants, 193 variants or 194 variants. The terms "from the A of the start codon", "from the U of the start codon" or "from the G of the start codon" define the starting points of the deletion, substitution or inversion. The term "from the A of the start codon" exemplary defines that the deletion, substitution or inversion starts from the A of the start codon (AUG) and affects the A.

In one aspect, the IBV of the present invention comprises a deletion, substitution or inversion from the A, U, or G of the start codon (AUG) of the ORF 5a and ORF 5b of nucleotides 1-10, nucleotides 1-20, nucleotides 1-30, nucleotides 1-40, nucleotides 1-50, nucleotides 1-60, nucleotides 1-70, nucleotides 1-80, nucleotides 1-90, nucleotides 1-100, nucleotides 1-110, nucleotides 1-120, nucleotides 1-130, nucleotides 1-140, nucleotides 1-150, nucleotides 1-160, nucleotides 1-170, nucleotides 1-180, nucleotides 1-189.

In another aspect of the present invention at least 174 nucleotides, at least 175 nucleotides, at least 176 nucleotides, at least 180, nucleotides, at least 190 nucleotides, at least 200 nucleotides, at least 225 nucleotides, at least 250 nucleotides, at least 300 nucleotides, at least 325 nucleotides, at least 340 nucleotides from the 5'-Terminus of the start codon (AUG, nucleotides 1-3 of SEQ ID NO:1) of ORF 3a are deleted, substituted or inverted within the ORF 3a and ORF 3b. Thus, one embodiment of the present invention provides an IBV or an immunogenic composition comprising an IBV (infectious bronchitis virus), wherein:
  the ORF 3a and ORF 3b are inactivated; or
  the ORF 3a and ORF 3b and the ORF 5a and ORF 5b are inactivated,
wherein at least 174 nucleotides, at least 175 nucleotides, at least 176 nucleotides, at least 180, nucleotides, at least 190 nucleotides, at least 200 nucleotides, at least 225 nucleotides, at least 250 nucleotides, at least 300 nucleotides, at least 325 nucleotides, at least 340 nucleotides from the 5'-Terminus of the ORF 3a are deleted, substituted or inverted within the ORF 3a and ORF 3b.

In one aspect of the present invention at least 174 nucleotides, at least 175 nucleotides, at least 176 nucleotides, at least 180, nucleotides, at least 190 nucleotides, at least 200 nucleotides, at least 225 nucleotides, at least 250 nucleotides, at least 300 nucleotides, at least 325 nucleotides, at least 340 nucleotides from the A, U, or G of the start codon (AUG, nucleotides 1-3 of SEQ ID NO:1) of ORF 3a are deleted, substituted or inverted within the ORF 3a and ORF 3b. Thus, one embodiment of the present invention provides an IBV or an immunogenic composition comprising an IBV (infectious bronchitis virus), wherein:
  the ORF 3a and ORF 3b are inactivated; or
  the ORF 3a and ORF 3b and the ORF 5a and ORF 5b are inactivated, wherein at least 174 nucleotides, at least 175 nucleotides, at least 176 nucleotides, at least 180, nucleotides, at least 190 nucleotides, at least 200 nucleotides, at least 225 nucleotides, at least 250 nucleotides, at least 300 nucleotides, at least 325 nucleotides, at least 340 nucleotides from the A, U or G of the start codon (AUG, nucleotides 1-3 of SEQ ID NO:1) of ORF 3a are deleted, substituted or inverted within the ORF 3a and ORF 3b.

In one aspect of the present invention at least 195 nucleotides, at least 196 nucleotides, at least 197 nucleotides, at least 200, nucleotides, at least 210 nucleotides, at least 220 nucleotides, at least 225 nucleotides, at least 250 nucleotides, at least 300 nucleotides, at least 325 nucleotides, at least 350 nucleotides, at least 380 nucleotides from the 5'-Terminus of the start codon (AUG, nucleotides 1-3 of SEQ ID NO:2) of ORF 5a are deleted, substituted or inverted within the ORF 5a and ORF 5b. Thus, one embodiment of the present invention provides an IBV or an immunogenic composition comprising an IBV (infectious bronchitis virus), wherein:

the ORF 5a and ORF 5b are inactivated; or
the ORF 3a and ORF 3b and the ORF 5a and ORF 5b are inactivated,
wherein at least 195 nucleotides, at least 196 nucleotides, at least 197 nucleotides, at least 200, nucleotides, at least 210 nucleotides, at least 220 nucleotides, at least 225 nucleotides, at least 250 nucleotides, at least 300 nucleotides, at least 325 nucleotides, at least 350 nucleotides, at least 380 nucleotides from the 5'-Terminus of the start codon (AUG, nucleotides 1-3 of SEQ ID NO:2) of ORF 5a are deleted, substituted or inverted within the ORF 5a and ORF 5b.

In one aspect of the present invention at least 195 nucleotides, at least 196 nucleotides, at least 197 nucleotides, at least 200, nucleotides, at least 210 nucleotides, at least 220 nucleotides, at least 225 nucleotides, at least 250 nucleotides, at least 300 nucleotides, at least 325 nucleotides, at least 350 nucleotides, at least 380 nucleotides from the A, U or G of the start codon (AUG, nucleotides 1-3 of SEQ ID NO:2) of ORF 5a are deleted, substituted or inverted within the ORF 5a and ORF 5b. Thus, one embodiment of the present invention provides an IBV or an immunogenic composition comprising an IBV (infectious bronchitis virus), wherein:

the ORF 5a and ORF 5b are inactivated; or
the ORF 3a and ORF 3b and the ORF 5a and ORF 5b are inactivated,
wherein at least 195 nucleotides, at least 196 nucleotides, at least 197 nucleotides, at least 200, nucleotides, at least 210 nucleotides, at least 220 nucleotides, at least 225 nucleotides, at least 250 nucleotides, at least 300 nucleotides, at least 325 nucleotides, at least 350 nucleotides, at least 380 nucleotides from the A, U, or G of the start codon (AUG, nucleotides 1-3 of SEQ ID NO:2) of ORF 5a are deleted, substituted or inverted within the ORF 5a and ORF 5b.

In one aspect of the present invention between 174 and 200 nucleotides or between 174 and 300 nucleotides or between 174 and 348 nucleotides from the 5'-Terminus of the start codon (AUG, nucleotides 1-3 of SEQ ID NO:1) of ORF 3a are deleted, substituted or inverted within the ORF 3a and ORF 3b. Thus, one embodiment of the present invention provides an IBV or an immunogenic composition comprising an IBV (infectious bronchitis virus), wherein:

the ORF 3a and ORF 3b are inactivated; or
the ORF 3a and ORF 3b and the ORF 5a and ORF 5b are inactivated,
wherein between 174 and 200 nucleotides or between 174 and 300 nucleotides or between 174 and 348 nucleotides from the 5'-Terminus of the start codon (AUG, nucleotides 1-3 of SEQ ID NO:1) of ORF 3a are deleted, substituted or inverted within the ORF 3a and ORF 3b.

In one aspect of the present invention between 174 and 348 nucleotides from the A of the start codon (A of AUG, nucleotide 1 of SEQ ID NO:1) or between 173 and 347 nucleotides from the U of the start codon (U of AUG, nucleotide 2 of SEQ ID NO:1) or between 172 and 346 nucleotides from the G of the start codon (G of AUG, nucleotide 3 of SEQ ID NO:1) of ORF 3a are deleted, substituted or inverted within the ORF 3a and ORF 3b. Thus, one embodiment of the present invention provides an IBV or an immunogenic composition comprising an IBV (infectious bronchitis virus), wherein:

the ORF 3a and ORF 3b are inactivated; or
the ORF 3a and ORF 3b and the ORF 5a and ORF 5b are inactivated,
wherein between 174 and 348 nucleotides from the A of the start codon (A of AUG, nucleotide 1 of SEQ ID NO:1) or between 173 and 347 nucleotides from the U of the start codon (U of AUG, nucleotide 2 of SEQ ID NO:1) or between 172 and 346 nucleotides from the G of the start codon (G of AUG, nucleotide 3 of SEQ ID NO:1) of ORF 3a are deleted, substituted or inverted within the ORF 3a and ORF 3b.

In one aspect of the present invention between 195 and 250 nucleotides or between 195 and 300 nucleotides or between 195 and 350 or between 195 and 385 nucleotides from the 5'-Terminus of the start codon (AUG, nucleotides 1-3 of SEQ ID NO:2) of the ORF 5a are deleted, substituted or inverted within the ORF 5a and ORF 5b. Thus, one embodiment of the present invention provides an IBV or an immunogenic composition comprising an IBV (infectious bronchitis virus), wherein:

the ORF 5a and ORF 5b are inactivated; or
the ORF 3a and ORF 3b and the ORF 5a and ORF 5b are inactivated,
wherein between 195 and 250 nucleotides or between 195 and 300 nucleotides or between 195 and 350 or between 195 and 385 nucleotides from the 5'-Terminus of the start codon (AUG, nucleotides 1-3 of SEQ ID NO:2) of the ORF 5a are deleted, substituted or inverted within the ORF 5a and ORF 5b.

In one aspect of the present invention between 195 and 385 nucleotides from the A of the start codon (A of AUG, nucleotide 1 of SEQ ID NO:2) or between 194 and 384 nucleotides from the U of the start codon (U of AUG, nucleotide 2 of SEQ ID NO:2) or between 193 and 383 nucleotides from the G of the start codon (G of AUG, nucleotide 3 of SEQ ID NO:2) of the ORF 5a are deleted, substituted or inverted within the ORF 5a and ORF 5b. Thus, one embodiment of the present invention provides an IBV or an immunogenic composition comprising an IBV (infectious bronchitis virus), wherein:

the ORF 5a and ORF 5b are inactivated; or
the ORF 3a and ORF 3b and the ORF 5a and ORF 5b are inactivated,
wherein between 195 and 385 nucleotides from the A of the start codon (A of AUG, nucleotide 1 of SEQ ID NO:2) or between 194 and 384 nucleotides from the U of the start codon (U of AUG, nucleotide 2 of SEQ ID NO:2) or between 193 and 383 nucleotides from the G of the start codon (G of AUG, nucleotide 3 of SEQ ID NO:2) of the ORF 5a are deleted, substituted or inverted within the ORF 5a and ORF 5b.

In one aspect of the present invention at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides of the ORF 3a are deleted, substituted or inverted, and, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides of the ORF 3b are deleted, substituted or inverted. Thus, one embodiment of the present invention provides an IBV or an immunogenic composition comprising an IBV (infectious bronchitis virus), wherein:

the ORF 3a and ORF 3b are inactivated; or the ORF 3a and ORF 3b and the ORF 5a and ORF 5b are inactivated, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides of the ORF 3a are deleted, substituted or inverted, and, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides of the ORF 3b are deleted, substituted or inverted.

In one aspect of the present invention at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides of the ORF 5a are deleted, substituted or inverted, and, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides of the ORF 5b are deleted, substituted or inverted. Thus, one embodiment of the present invention provides an IBV or an immunogenic composition comprising an IBV (infectious bronchitis virus), wherein:

the ORF 5a and ORF 5b are inactivated; or the ORF 3a and ORF 3b and the ORF 5a and ORF 5b are inactivated, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides of the ORF 5a are deleted, substituted or inverted and, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides of the ORF 5b are deleted, substituted or inverted.

In general, the term "nucleotides of the ORF 3a/3b/5a/5b are deleted, substituted or inverted" refers to a deletion, substitution or inversion of nucleotides that may occur everywhere within said ORF. Thus, said deletion, substitution or inversion of nucleotides may affect only the 5'-Terminus of said ORF, only the 3'-Terminus of said ORF or the rest of the nucleotides (excluding 5'-Terminus and 3'-Terminus) of said ORF or any combinations thereof (such as exemplary the 5'-Terminus of said ORF and further nucleotides or the 3'-Terminus of said ORF and further nucleotides). Thus, exemplary the wording "at least 25 nucleotides of the ORF 3a/3b/5a/5b are deleted, substituted or inverted" means that said 25 nucleotides can be deleted, substituted or inverted everywhere within said ORF with no limitation towards the localization of the deletion, substitution or inversion of nucleotides within said ORF. Further, exemplary the wording "between 1 and 173 nucleotides of the ORF 3a are deleted, substituted or inverted" means that said nucleotides can be deleted, substituted or inverted everywhere within said ORF with no limitation towards the localization of the deletion, substitution or inversion of nucleotides within said ORF. Furthermore, as set forth above, it is to be understood that the term "between 1 and 173 nucleotides" encompasses 173 variants (deletions, substitutions or inversions of 1, 2, 3, 4 and so forth until 171, 172 or 173 nucleotides). Accordingly, it is to be understood that the term "between 1 and 175 nucleotides" encompasses 175 variants (deletions, substitutions or inversions of 1, 2, 3, 4 and so forth until 173, 174 or 175 nucleotides), the term "between 1 and 194 nucleotides" encompasses 194 variants (deletions, substitutions or inversions of 1, 2, 3, 4 and so forth until 192, 193 or 194 nucleotides), the term "between 1 and 90 nucleotides" encompasses 90 variants (deletions, substitutions or inversions of 1, 2, 3, 4 and so forth until 88, 89 or 90 nucleotides), the term "between 1 and 191 nucleotides" encompasses 191 variants (deletions, substitutions or inversions of 1, 2, 3, 4 and so forth until 189, 190 or 191 nucleotides), the term "between 1 and 348 nucleotides" encompasses 348 variants (deletions, substitutions or inversions of 1, 2, 3, 4 and so forth until 346, 347 or 348 nucleotides) and the term "between 1 and 385 nucleotides" encompasses 385 variants (deletions, substitutions or inversions of 1, 2, 3, 4 and so forth until 383, 384 or 385 nucleotides).

In one aspect of the present invention between 1 and 173 nucleotides of the ORF 3a are deleted, substituted or inverted, and, wherein between 1 and 175 nucleotides of the ORF 3b are deleted, substituted or inverted. Thus, one embodiment of the present invention provides an IBV or an immunogenic composition comprising an IBV (infectious bronchitis virus), wherein:

the ORF 3a and ORF 3b are inactivated; or the ORF 3a and ORF 3b and the ORF 5a and ORF 5b are inactivated, wherein between 1 and 173 nucleotides of the ORF 3a are deleted, substituted or inverted, and, wherein between 1 and 175 nucleotides of the ORF 3b are deleted, substituted or inverted.

In one aspect of the present invention between 1 and 194 nucleotides of the ORF 5a are deleted, substituted or inverted, and, wherein between 1 and 191 nucleotides of the ORF 5b are deleted, substituted or inverted. Thus, one embodiment of the present invention provides an IBV or an immunogenic composition comprising an IBV (infectious bronchitis virus), wherein:

the ORF 5a and ORF 5b are inactivated; or the ORF 3a and ORF 3b and the ORF 5a and ORF 5b are inactivated, wherein between 1 and 194 nucleotides of the ORF 5a are deleted, substituted or inverted, and, wherein between 1 and 191 nucleotides of the ORF 5b are deleted, substituted or inverted.

In one aspect of the present invention between 176 and 348 nucleotides of the ORF 3a and ORF 3b are deleted, substituted or inverted within the 5'-Terminus of the start codon of the ORF 3a and the start codon of the ORF 3c. Thus, one embodiment of the present invention provides an IBV or an immunogenic composition comprising an IBV (infectious bronchitis virus), wherein:

the ORF 3a and ORF 3b are inactivated; or the ORF 3a and ORF 3b and the ORF 5a and ORF 5b are inactivated, wherein between 176 and 348 nucleotides of the ORF 3a and ORF 3b are deleted, substituted or inverted within the 5'-Terminus of the start codon of the ORF 3a and the start codon of the ORF 3c.

The term "within the 5'-Terminus of the start codon of the ORF 3a and the start codon of the ORF 3c" as used herein is to be understood that said deletion, substitution or inversion of nucleotides may affect (may include) the start codon of the ORF 3a, wherein the start codon of the ORF 3c is not affected (excluded). Thus, the expression of ORF 3c and/or the activity of the E protein is not affected. Thus, the term "within the 5'-Terminus of the start codon of the ORF 3a and the start codon of the ORF 3c" refers to a deletion, substitution or inversion of nucleotides that may occur everywhere within said ORF's as long as the start codon of the ORF 3c is not affected. Thus, said deletion, substitution or inversion of nucleotides may affect only the 5'-Terminus of ORF 3a, only the 3'-Terminus of ORF 3b (without affecting the start codon of the ORF 3c) or the rest of the nucleotides (excluding said 5'-Terminus and 3'-Terminus) of said ORF's or any combinations thereof. Furthermore, it is to be understood from the above that the term "between 176 and 348 nucleotides" encompasses deletions, substitutions or inversions of 176, 177, 178 and so forth until 346, 347 or 348 nucleotides.

In one aspect of the present invention between 176 and 348 nucleotides of the ORF 3a and ORF 3b are deleted, substituted or inverted within the 5'-Terminus of the start codon (AUG, nucleotides 1-3 of SEQ ID NO:1) of the ORF 3a to nucleotide 348 of SEQ ID NO:1. Thus, one embodiment of the present invention provides an IBV or an immunogenic composition comprising an IBV (infectious bronchitis virus), wherein:

the ORF 3a and ORF 3b are inactivated; or the ORF 3a and ORF 3b and the ORF 5a and ORF 5b are inactivated, wherein between 176 and 348 nucleotides of the ORF 3a and ORF 3b are deleted, substituted or inverted within the 5'-Terminus of the start codon (AUG, nucleotides 1-3 of SEQ ID NO:1) of the ORF 3a to nucleotide 348 of SEQ ID NO:1. Thus, the inactivation of ORF 3a and ORF 3b does not affect the expression of ORF 3c and/or not the activity of the E protein. Thus, the ORF 3a and ORF 3b expression (3a and 3b RNA and/or 3a protein and 3b protein) and/or activity of the protein is reduced (or eliminated) whereas the expression ORF 3c is and/or activity of the E protein is not affected.

In one aspect of the present invention at least 176 nucleotides, at least 180 nucleotides, at least 200 nucleotides, at least 225, nucleotides, at least 250 nucleotides, at least 300 nucleotides, at least 340 nucleotides of the ORF 3a and ORF 3b are deleted, substituted or inverted within the 5'-Terminus of the start codon of the ORF 3a and the start codon of the ORF 3c. Thus, one embodiment of the present invention provides an IBV or an immunogenic composition comprising an IBV (infectious bronchitis virus), wherein:

the ORF 3a and ORF 3b are inactivated; or the ORF 3a and ORF 3b and the ORF 5a and ORF 5b are inactivated, wherein at least 176 nucleotides, at least 180 nucleotides, at least 200 nucleotides, at least 225, nucleotides, at least 250 nucleotides, at least 300 nucleotides, at least 340 nucleotides of the ORF 3a and ORF 3b are deleted, substituted or inverted within the 5'-Terminus of the start codon of the ORF 3a and the start codon of the ORF 3c.

In one aspect of the present invention at least 176 nucleotides, at least 180 nucleotides, at least 200 nucleotides, at least 225, nucleotides, at least 250 nucleotides, at least 300 nucleotides, at least 340 nucleotides of the ORF 3a and ORF 3b are deleted, substituted or inverted within the 5'-Terminus of the start codon (AUG, nucleotides 1-3 of SEQ ID NO:1) of the ORF 3a to nucleotide 348 of SEQ ID NO:1. Thus, one embodiment of the invention provides an IBV or an immunogenic composition comprising an IBV (infectious bronchitis virus), wherein:

the ORF 3a and ORF 3b are inactivated; or the ORF 3a and ORF 3b and the ORF 5a and ORF 5b are inactivated, wherein at least 176 nucleotides, at least 180 nucleotides, at least 200 nucleotides, at least 225, nucleotides, at least 250 nucleotides, at least 300 nucleotides, at least 340 nucleotides of the ORF 3a and ORF 3b are deleted, substituted or inverted within the 5'-Terminus of the start codon (AUG, nucleotides 1-3 of SEQ ID NO:1) of the ORF 3a to nucleotide 348 of SEQ ID NO:1. Thus, the inactivation of ORF 3a and ORF 3b does not affect the expression of ORF 3c and/or not the activity of the E protein. Thus, the ORF 3a and ORF 3b expression (3a and 3b RNA and/or 3a protein and 3b protein) and/or activity of the protein is reduced (or eliminated) whereas the expression of ORF 3c and/or the activity of the E protein is not affected.

In one aspect of the present invention between 195 and 385 nucleotides of the ORF 5a and ORF 5b are deleted, substituted or inverted within the 5'-Terminus of the start codon of the ORF 5a and the start codon of the ORF N. Thus, one embodiment of the invention provides an IBV or an immunogenic composition comprising an IBV (infectious bronchitis virus), wherein:

the ORF 5a and ORF 5b are inactivated; or the ORF 3a and ORF 3b and the ORF 5a and ORF 5b are inactivated, wherein invention between 195 and 385 nucleotides of the ORF 5a and ORF 5b are deleted, substituted or inverted within the 5'-Terminus of the start codon of the ORF 5a and the start codon of the ORF N.

The term "within the 5'-Terminus of the start codon of the ORF 5a and the start codon of the ORF N" as used herein is to be understood that said deletion, substitution or inversion of nucleotides may affect (may include) the start codon of the ORF 5a, wherein the start codon of the ORF N is not affected (excluded). Thus, the expression of ORF N and/or the activity of the N protein is not affected. Thus, the term "within the 5'-Terminus of the start codon of the ORF 5a and the start codon of the ORF N" refers to a deletion, substitution or inversion of nucleotides that may occur everywhere within said ORF's as long as the start codon of the ORF N is not affected. Thus, said deletion, substitution or inversion of nucleotides may affect only the 5'-Terminus of ORF 5a, only the 3'-Terminus of ORF 5b (without affecting the start codon of the ORF N) or the rest of the nucleotides (excluding said 5'-Terminus and 3'-Terminus) of said ORF's or any combinations thereof. Furthermore, it is to be understood from the above that the term "between 195 and 385 nucleotides" encompasses deletions, substitutions or inversions of 195, 196, 197 and so forth until 383, 384 or 385 nucleotides.

In one aspect of the present invention between 195 and 385 nucleotides of the ORF 5a and ORF 5b are deleted, substituted or inverted within the 5'-Terminus of the start codon (AUG, nucleotides 1-3 of SEQ ID NO:2) of the ORF 5a to nucleotide 385 of SEQ ID NO:2. Thus, one embodiment of the present invention provides an IBV or an immunogenic composition comprising an IBV (infectious bronchitis virus), wherein:

the ORF 5a and ORF 5b are inactivated; or the ORF 3a and ORF 3b and the ORF 5a and ORF 5b are inactivated, wherein between 195 and 385 nucleotides of the ORF 5a and ORF 5b are deleted, substituted or inverted within the 5'-Terminus of the start codon (AUG, nucleotides 1-3 of SEQ ID NO:2) of the ORF 5a to nucleotide 385 of SEQ ID NO:2. Thus, the inactivation of ORF 5a and ORF 5b does not affect the expression of ORF N and/or not the activity of the N protein. Thus, the ORF 5a and ORF 5b expression (5a and 5b RNA and/or 5a protein and 5b protein) and/or activity of the protein is reduced (or eliminated) whereas the expression of ORF N and/or the activity of the N protein is not affected.

In one aspect of the present invention wherein at least 195 nucleotides, at least 200 nucleotides, at least 225 nucleotides, at least 250, nucleotides, at least 300 nucleotides, at least 350 nucleotides, at least 380 nucleotides of the ORF 5a and ORF 5b are deleted, substituted or inverted within the 5'-Terminus of the start codon of the ORF 5a and the start codon of the ORF N. Thus, one embodiment of the present invention provides an IBV or an immunogenic composition comprising an IBV (infectious bronchitis virus), wherein:

the ORF 5a and ORF 5b are inactivated; or the ORF 3a and ORF 3b and the ORF 5a and ORF 5b are inactivated, wherein at least 195 nucleotides, at least 200 nucleotides, at least 225 nucleotides, at least 250, nucleotides, at least 300 nucleotides, at least 350 nucleotides, at least 380 nucleotides of the ORF 5a and ORF 5b are deleted, substituted or inverted within the 5'-Terminus of the start codon of the ORF 5a and the start codon of the ORF N.

In one aspect of the present invention at least 195 nucleotides, at least 200 nucleotides, at least 225 nucleotides, at least 250, nucleotides, at least 300 nucleotides, at least 350 nucleotides, at least 380 nucleotides of the ORF 5a and ORF 5b are deleted, substituted or inverted within the 5'-Terminus of the start codon (AUG, nucleotides 1-3 of SEQ ID NO:2) of the ORF 5a to nucleotide 385 of SEQ ID NO:2. Thus, one embodiment of the present invention provides an IBV or an immunogenic composition comprising an IBV (infectious bronchitis virus), wherein:

the ORF 5a and ORF 5b are inactivated; or the ORF 3a and ORF 3b and the ORF 5a and ORF 5b are inactivated, wherein at least 195 nucleotides, at least 200 nucleotides, at least 225 nucleotides, at least 250, nucleotides, at least 300 nucleotides, at least 350 nucleotides, at least 380 nucleotides of the ORF 5a and ORF 5b are deleted, substituted or inverted within the 5'-Terminus of the start codon (AUG, nucleotides 1-3 of SEQ ID NO:2) of the ORF 5a to nucleotide 385 of SEQ ID NO:2.

In one aspect of the present invention the ORF 3a and ORF 3b from the 5'-Terminus of the start codon (AUG, nucleotides 1-3 of SEQ ID NO:1) of the ORF 3a to nucleotide 348 of SEQ ID NO:1 is deleted, substituted or inverted. Thus, one embodiment of the present invention provides an IBV or an immunogenic composition comprising an IBV (infectious bronchitis virus), wherein:

the ORF 3a and ORF 3b are inactivated; or the ORF 3a and ORF 3b and the ORF 5a and ORF 5b are inactivated, wherein the ORF 3a and ORF 3b from the 5'-Terminus of the start codon (AUG, nucleotides 1-3 of SEQ ID NO:1) of the ORF 3a to nucleotide 348 of SEQ ID NO:1 is deleted, substituted or inverted.

In one aspect of the present invention the RNA sequence as set forth in SEQ ID NO:1 is deleted, substituted or inverted within the ORF 3a and ORF 3b. Thus, one embodiment of the present invention provides an IBV or an immunogenic composition comprising an IBV (infectious bronchitis virus), wherein:

the ORF 3a and ORF 3b are inactivated; or the ORF 3a and ORF 3b and the ORF 5a and ORF 5b are inactivated, wherein the RNA sequence as set forth in SEQ ID NO:1 is deleted, substituted or inverted within the ORF 3a and ORF 3b.

In one aspect of the present invention a RNA sequence having at least 70% identity to the RNA sequence as set forth in SEQ ID NO:1 is deleted, substituted or inverted within the ORF 3a and ORF 3b. Thus, one embodiment of the present invention provides an IBV or an immunogenic composition comprising an IBV (infectious bronchitis virus), wherein:

the ORF 3a and ORF 3b are inactivated; or the ORF 3a and ORF 3b and the ORF 5a and ORF 5b are inactivated, wherein a RNA sequence having at least 70% identity to the RNA sequence as set forth in SEQ ID NO:1 is deleted, substituted or inverted within the ORF 3a and ORF 3b.

In one aspect of the present invention a RNA sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the RNA sequence as set forth in SEQ ID NO:1 is deleted, substituted, or inverted within the ORF 3a and ORF 3b. Thus, one embodiment of the present invention provides an IBV or an immunogenic composition comprising an IBV (infectious bronchitis virus), wherein:

the ORF 3a and ORF 3b are inactivated; or the ORF 3a and ORF 3b and the ORF 5a and ORF 5b are inactivated, wherein a RNA sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the RNA sequence as set forth in SEQ ID NO:1 is deleted, substituted, or inverted within the ORF 3a and ORF 3b.

The term "identity" or "sequence identity" is known in the art and refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

The terms "identity", "sequence identity" and "percent identity" are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length.

A sequence comparison may be carried out over the entire lengths of the two sequences being compared or over fragment of the two sequences. Typically, the comparison will be carried out over the full length of the two sequences being compared. However, sequence identity may be carried out over a region of, for example, twenty, fifty, one hundred or more contiguous amino acid residues.

The skilled person will be aware of the fact that different computer programs are available to determine the homology between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch (J. Mol. Biol. (48): 444-453 (1970)) algorithm which has been incorporated into the GAP program in the Accelrys GCG software package (available at http://www.accelrys.com/products/gcg/), using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms The protein sequences or nucleic acid sequences of the present invention can further be used as a "query sequence" to perform a search against public databases to, for example, to identify other family members or related sequences. Such searches can be performed using the BLASTN and BLASTP programs (version 2.0) of Altschul, et al. (1990) J. Mol. Biol.

215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al. (1997) Nucleic Acids Res. 25(17): 3389-3402. When utilizing BLAST and Gapped BLAST programs, the default parameters of the respective programs (e.g., BLASTP and BLASTN) can be used. See the homepage of the National Center for Biotechnology Information at http://www.ncbi.nlm.nih.gov/.

In one aspect of the present invention the ORF 5a and ORF 5b from the 5'-Terminus of the start codon (AUG, nucleotides 1-3 of SEQ ID NO:2) of the ORF 5a to nucleotide 385 of SEQ ID NO:2 is deleted, substituted, or inverted. Thus, one embodiment of the present invention provides an IBV or an immunogenic composition comprising an IBV (infectious bronchitis virus), wherein:
  the ORF 5a and ORF 5b are inactivated; or
  the ORF 3a and ORF 3b and the ORF 5a and ORF 5b are inactivated,
wherein the ORF 5a and ORF 5b from the 5'-Terminus of the start codon (AUG, nucleotides 1-3 of SEQ ID NO:2) of the ORF 5a to nucleotide 385 of SEQ ID NO:2 is deleted, substituted or inverted.

In one aspect of the present invention the RNA sequence as set forth in SEQ ID NO:2 is deleted, substituted or inverted within the ORF 5a and ORF 5b. Thus, one embodiment of the present invention provides an IBV or an immunogenic composition comprising an IBV (infectious bronchitis virus), wherein:
  the ORF 5a and ORF 5b are inactivated; or
  the ORF 3a and ORF 3b and the ORF 5a and ORF 5b are inactivated,
wherein the RNA sequence as set forth in SEQ ID NO:2 is deleted, substituted or inverted within the ORF 5a and ORF 5b.

In one aspect of the present invention a RNA having at least 70% identity to the RNA sequence as set forth in SEQ ID NO:2 is deleted, substituted or inverted within the ORF 5a and ORF 5b. Thus, one embodiment of the present invention provides an IBV or an immunogenic composition comprising an IBV (infectious bronchitis virus), wherein:
  the ORF 5a and ORF 5b are inactivated; or
  the ORF 3a and ORF 3b and the ORF 5a and ORF 5b are inactivated,
wherein a RNA sequence having at least 70% identity to the RNA sequence as set forth in SEQ ID NO:2 is deleted, substituted or inverted within the ORF 5a and ORF 5b.

In one aspect of the present invention a RNA sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the RNA sequence as set forth in SEQ ID NO:2 is deleted, substituted or inverted within the ORF 5a and ORF 5b. Thus, one embodiment of the present invention provides an IBV or an immunogenic composition comprising an IBV (infectious bronchitis virus), wherein:
  the ORF 5a and ORF 5b are inactivated; or
  the ORF 3a and ORF 3b and the ORF 5a and ORF 5b are inactivated,
wherein a RNA sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the RNA sequence as set forth in SEQ ID NO:2 is deleted, substituted or inverted within the ORF 5a and ORF 5b.

In one aspect of the present invention the E protein has an amino acid sequence of genotype QX, Beaudette, H120 or H52 or a sequence having at least 70%, at least 75%, at least 80%, at least 85%, at least 90%, at least 91%, at least 92%, at least 93%, at least 94%, at least 95%, at least 96%, at least 97%, at least 98%, at least 99% or at least 99.5% sequence identity to at least one of the above mentioned genotypes.

In one aspect of the present invention the E protein has an amino acid sequence as shown for KM586818 (QX), AJ311317 (Beaudette), FJ807652 (H120) or SEQ ID NO: 38 (H52) or a sequence having at least 70%, at least 75%, at least 80%, at least 85%, at least 90%, at least 91%, at least 92%, at least 93%, at least 94%, at least 95%, at least 96%, at least 97%, at least 98%, at least 99% or at least 99.5% sequence identity to at least one of the above mentioned sequences.

In one aspect of the present invention the IBV is attenuated.

The term "attenuated" refers to a pathogen having a reduced virulence in comparison to the wildtype isolate. In the present invention, an attenuated IBV is one in which the virulence has been reduced so that it does not cause clinical signs of an IBV infection but is capable of inducing an immune response in the target animal, but may also mean that the clinical signs are reduced in incidence or severity in animals infected with the attenuated IBV in comparison with a "control group" of animals infected with non-attenuated IBV and not receiving the attenuated virus. In this context, the term "reduce/reduced" means a reduction of at least 10%, preferably 25%, even more preferably 50%, still more preferably 60%, even more preferably 70%, still more preferably 80%, still more preferably 90%, even more preferably 95% and most preferably of 100% as compared to the control group infected with non-attenuated IBV as defined above. Thus, an attenuated, IBV strain is one that is suitable for incorporation into an immunogenic composition comprising a modified live IBV.

Thus, one embodiment of the present invention provides an attenuated IBV or an immunogenic composition comprising an attenuated IBV (infectious bronchitis virus), wherein:
  the ORF 3a and ORF 3b are inactivated; or
  the ORF 5a and ORF 5b are inactivated; or
  the ORF 3a and ORF 3b and the ORF 5a and ORF 5b are inactivated.

Thus, one embodiment of the present invention provides an attenuated IBV or an immunogenic composition comprising an attenuated IBV (infectious bronchitis virus), wherein the ORF 3a and ORF 3b are inactivated.

Thus, one embodiment of the present invention provides an attenuated IBV or an immunogenic composition comprising an attenuated IBV (infectious bronchitis virus), wherein the ORF 5a and ORF 5b are inactivated.

Thus, one embodiment of the present invention provides an attenuated IBV or an immunogenic composition comprising an attenuated IBV (infectious bronchitis virus), wherein the ORF 3a and ORF 3b and the ORF 5a and ORF 5b are inactivated.

Inactivated Virus

In one aspect of the present invention the IBV of the present invention has been inactivated resulting in whole inactivated viruses. Thus, one embodiment of the present invention also refers to an immunogenic composition comprising an inactivated IBV wherein:

the ORF 3a; and/or
the ORF 3b; and/or
the ORF 5a; and/or
the ORF 5b is inactivated.

In another aspect of the present invention the IBV of the present invention has been inactivated resulting in whole inactivated viruses. Thus, one embodiment of the present invention also refers to an immunogenic composition comprising:

an inactivated IBV, wherein the ORF 3a and ORF 3b are inactivated; or
an inactivated IBV, wherein the ORF 5a and ORF 5b are inactivated; or
an inactivated IBV, wherein the ORF 3a and ORF 3b and the ORF 5a and ORF 5b are inactivated.

Any conventional inactivation method can be used for purposes of the present invention. Thus, inactivation can be performed by chemical and/or physical treatments which are known to the person skilled in the art. Preferred inactivation methods include the addition of cyclized binary ethylenimine (BEI) including the addition of a solution of 2-bromoethyleneamine hydrobromide (BEA), which has been cyclized to binary ethylenimine (BEI). Preferred further chemical inactivation agents comprise but are not limited to Triton X-100, Sodium deoxycholate, Cetyltrimethylammonium bromide, β-Propiolactone, Thimerosal, Phenol and Formaldehyde (Formalin). However, the inactivation may also comprise a neutralization step. Preferred neutralization agents include but are not limited to sodium thiosulfate, sodium bisulfite and the alike.

Preferred formalin inactivation conditions include formalin concentration between from about 0.02% (v/v)-2.0% (v/v), more preferably from about 0.1% (v/v)-1.0% (v/v), still more preferably from about 0.15% (v/v)-0.8% (v/v), even more preferably from about 0.16% (v/v)-0.6% (v/v), and most preferably about 0.2% (v/v)-0.4% (v/v). Incubation time depends on the resistance of the IBV. In general, the inaction process is performed until no growth of the IBV can be detected in a suitable cultivation system.

Preferably, the inactivated IBV of the present invention is formalin inactivated, preferably using the concentrations as described hereinabove.

The inactivated IBV of the invention may be incorporated into liposomes using known technology such as that described in Nature, 1974, 252, 252-254 or Journal of Immunology, 1978, 120, 1109-13. In another embodiment of the invention, the inactivated IBV of the invention may be conjugated to suitable biological compounds such as polysaccharides, peptides, proteins, or the like, or a combination thereof.

In one aspect of the present invention the IBV is genetically engineered.

The term "genetically engineered" refers to an IBV which has been mutated by using "reverse genetics" approaches. Preferably, the IBV according to the present invention has been genetically engineered. The reverse genetics technique involves the preparation of synthetic recombinant viral RNAs. However, "reverse genetics" techniques are well known to the person skilled in the art.

In one aspect of the present invention the IBV is a recombinant IBV.

The term "recombinant" as used herein relates to a RNA genome (or RNA sequence or protein) having any modifications that do not naturally occur to the corresponding RNA genome (or RNA sequence or protein). For instance, a RNA genome (or RNA sequence or protein) is considered "recombinant" if it contains an insertion, deletion, inversion, relocation or a point mutation introduced artificially, e.g., by human intervention. Therefore, the RNA genomic sequence (or RNA sequence or protein) is not associated with all or a portion of the sequences (RNA sequence or amino acid sequence of the protein) with which it is associated in nature. The term "recombinant" as used with respect to a virus, means a virus produced by artificial manipulation of the viral genome. The term "recombinant virus" encompasses genetically modified viruses.

IBV Strains

IBV strains can be classified by serotype and genotype. Serotype classification involves treatment of the virus with neutralizing antibodies, whereas genotype classification involves examining the sequence of the S1 (spike) protein. However, the different IBV strains are well known to the person skilled in the art. Infectious bronchitis virus was first discovered in the United States in the 1930s. The first IBV serotype identified was Massachusetts, but in the United States several serotypes, including Arkansas and Delaware have been identified in addition to the originally identified Massachusetts type.

The IBV strain Beaudette is of Massachusetts type and was derived following at least 150 passages in chick embryos. IBV strain Beaudette was originally isolated by Beaudette and Hudson (J. Am. Vet. Med. A. 90, 51-60, 1937) and passaged several hundred times in chicken embryos, it is commonly referred to as a "chicken embryo adapted" or "egg adapted" strain. Other Massachusetts type IBV strains besides Beaudette are H120, H52, and M41.

IB QX has described as virulent field isolate of IBV which was originally isolated in China. However, the virus has crept towards Europe and has been identified in parts of Western Europe, predominantly in the Netherlands, but also in Germany, France, Belgium, Denmark and in the UK. The QX serotype has been described in several countries in Asia and Africa.

Another IBV strain is the 4/91 genotype which is commonly also called 793B.

The Strains designated "Italien-02" or "Italy-02" have been isolated in the late 1990's in Italy. The sequence analysis of one of these isolates was published in 2002 (NCBI-BLAST, number AJ457137). However, studies have shown that this Italian-02 strain is widespread in Europe and that, apart from IBV variant strain 4/91 it has become one of the most predominant genotypes in the UK, Spain, France and The Netherlands.

Furthermore, strains D274, B1648/D8880, D1466, V1397 and Arkansas have been identified in Europe as well.

In one aspect of the present invention the IBV has a genotype selected from a list of strains containing of: Arkansas (such as Arkansas 99), California (such as California 1734/04, California 99), Connecticut, Delaware (such as Delaware 98), Dutch (such as D207, D212, D274, D3128, D3896, D8880, D1466), Florida, Georgia (such as Georgia GA-08, GA-12, GA-13), Gray, Holte, Iowa (such as Iowa 97 and Iowa 69), Italy (such as Italy 02), JMK, Maine (such as Maine 209), Massachusetts (such as M41, Beaudette, 246 G, D 580, H52, H120), Pennsylvania (such as Pennsylvania 1220/98, Pennsylvania Wolg/98), Qu, (such as Qu-mv), QX (such as GB341/96), Q1, SE 17, Variant 2 (such as IS/1494/06) and 4/91(793B).

In one aspect of the present invention the IBV is of QX, Massachusetts, 4/91, Q1 or Italy 02 genotype.

In one aspect of the present invention the QX genotype is selected from a list containing of: FR-L1450T-05, FR-L1450L-05, NL-L1449T-04, NL-L1449K-04, IBV/Ck/

SP/170/09, IBV/Ck/SP/79/08, IBV/Ck/SP/248/09, HBN, IBVQX, LX4, BJQ, CK/CH/LGD/03, GB341/96.

In one aspect of the present invention the Massachusetts genotype is selected from a list containing of: H120, H52, Spain/98/308, IBMA5-1, SD/97/01, Beaudette, Spain/96/334, M41-M21883.

In one aspect of the present invention the 4/91 genotype is selected from a list containing of: Spain/98/328, Spain/92/35, IR-3654-VM, FR-CR88061-88, FR-85131-85, UK-1233-95, UK/3/91, Spain/00/336, UK/7/91, 4/91-pathogenic, 4/91 attenuated, IB4-91.

In one aspect of the present invention the Q1 genotype is selected from a list containing of: CK/CH/LDL/98I, CK/CH/LSD/08-10, J2, Q1, AR08ER22, AR08BA21, Chile-295-10.

In one aspect of the present invention the Italy 02 genotype is selected from a list containing of: Spain/99/316, Italy-02, UK-L633-04, It-497-02, Spain/05/866, Spain/04/221, Spain/00/337, Spain/155/09, Spain/03/08.

In one aspect of the present invention the IBV is of the Massachusetts genotype strain H52.

In one aspect of the present invention the H52 is H52U.

In one aspect of the present invention the H52 has a nucleotide sequence as shown for EU817497 or a sequence having at least 95%, at least 96%, at least 97%, at least 98%, at least 99% or at least 99.5% sequence identity thereto.

In one aspect of the present invention the H52 strain has a Spike (51) protein having an amino acid sequence as shown for AF352315 or a sequence having at least 95%, at least 96%, at least 97%, at least 98%, at least 99% or at least 99.5% sequence identity thereto.

In one aspect of the present invention the H52 strain has a Nucleocapsid (N) protein having an amino acid sequence as shown for AY044185 or AF352310 or a sequence having at least 95%, at least 96%, at least 97%, at least 98%, at least 99% or at least 99.5% sequence identity to at least one of the above mentioned sequences.

In one aspect of the present invention the H52 strain has an Envelope (E) protein having an amino acid sequence as shown for AF317210 or a sequence having at least 95%, at least 96%, at least 97%, at least 98%, at least 99% or at least 99.5% sequence identity thereto.

In one aspect of the present invention the H52 strain has a Membrane glycoprotein (M) protein having an amino acid sequence as shown for AF286185 or a sequence having at least 95%, at least 96%, at least 97%, at least 98%, at least 99% or at least 99.5% sequence identity thereto.

It is in the general knowledge of a person skilled in the art where to obtain any IBV strains. IBV strains can be commercially purchased, obtained from scientific Institutes or the genomes can be synthetically synthesized as complementary DNA as IBV strains have been sequenced and the sequences have been published and are, thus, available. Furthermore, IBV strains can be isolated from the field. The methods to isolate IBV strains and to characterize the IBV strains are well known to the person skilled in the art. Valter Leonardo de Quadros 2011 (Dissertation, Das Infektiose Bronchitis Virus (IBV): Molekularbiologische Untersuchungen zur Diagnostik and zum Vorkommen sowie zur Pathogenität des Genotyps IBV QX in spezifisch pathogenfreien (SPF) Broilern, Freie Universität Berlin), Worthington et al 2009 (Avian Pathology 37(3), 247-257), Liu et al 2009 (Virus Genes 38: 56-65), Dolz et al 2006 (Avian Pathology 35 (2): 77-85), Farsang et al 2002 (Avian Pathology 31: 229-236) and Feng et al 2014 (Virus Genes 49: 292-303) describe how to isolate and differentiate different IBV strains.

Exemplary, it is in the general knowledge of a person skilled in the art where to obtain IBV H52. IBV H52 strains can be commercially purchased such as exemplary Nobilis IB H52 (MSD Animal Health), AviPro IB H52 (Lohmann Animal Health GmbH & Co. KG), Bronchovac (Ceva) and the alike. Further, McDonald et al 1980 (Avian Pathology 9:245-259) disclose that IBV H52 can be obtained by Central Veterinary Laboratory Rotterdam, Kusters (J. gen Virol 68:343-352) disclose that IBV H52 can be obtained by the Poultry Health Institute Dorn in the Netherlands (which is now Deventer Institute; IBV H52 can be obtained at Deventer) and Chen et al 2007 (Avian Pathology 36(4):269-274) disclose that IBV H52 can be obtained by the China Institute of Veterinary Drug Control. Furthermore, IBV H52 is used as vaccine strain for decades (Bijlenga et al 2004, Avian Pathology 33 (6): 550-557) and, therefore, can be found and isolated from the field. The methods to isolate IBV H52 strains and to characterize the IBV H52 strains are well known to the person skilled in the art. Exemplary, IBV H52 strains can be characterized as described in Zwaagstra et al 1992 (J. Clin. Microbiol. 30 (1): 79-84), Handberg et al 1999 (Avian Pathology 28: 327-335) or Callison et al 2006 (Journal of Virological Methods 138: 60-65). Zwaagstra et al 1992 and Handberg et al 1999 for example disclose Massachusetts specific Primers (for the S and N protein, respectively) for RT-PCR and sequencing and reference sequences for comparison.

Further, the term "IBV" is meant to encompass numerous serotypes of IBV which have been isolated and characterized including (but not limited to): B/D207/84; B/D274/84; B/UK 167/84; B/UK142/86; E D3S96/84; E/UK 123/82; Brazil/BR1/USP-73/09; 793B/4-91/91; FR/CR88121 88; China/Q1/98; Chka/LDL971 97 aaz09202; CAV/CAV9437/95; CAV/CAV1 86/95; CAV/CAV56b 91; PA/Wolgemnth/98; PA/i 71/99; C/557/03 SI; JAA/04 SI vaccine; HN99 SI; N1/62/SI; GAGS SI GU301925; Ark/ArkDPI 81 SI; Ark/Ark99/73; CAL99/CAL99/99 SI; CAL99/NE15172/95 SI; Holte/Holte/54; JMK/JMK/64; Gray/Gray/60; Iowa/Iowa609/56; Ca 1737/04 SI; DMA/5642/06 SI; GA07/GA07/07 Si; QX/QXIBV/99; Mass/H52/SI; Mass/Hi 20/SI; Mass/Mass41/41 SI; Cofln/Corm46/51 SI vaccine: FL/FL i 8288/71; DE DE072/92 SI vaccine; GA98/Q470/98 SI; and Dutch/D 1466/81.

Further examples of typical reference strains and the nucleotide sequence database accession numbers of their spike gene sequences are M41 (Massachusetts serotype; X04722), NUD274/78 (D274 serotype; X15832), USA/Arkansas 99 (Ark 99 serotype; L10384), Belgium/B1648 (B1648 serotype; X87238), USA (DE)/072/92 (DE072 serotype; U77298), US (GA)/0470/98 (Georgia 98 serotype; AF274437), Ut14/91 (793B1 serotype; AF093794), USA/Connecticut (Connecticut serotype; L18990) and NL/D1466 (D1466 serotype; M21971).

In one aspect of the present invention the immunogenic composition is a vaccine. The term "vaccine" already has been described elsewhere herein. However, in case where the host displays a protective immunological response such that resistance to new infection will be enhanced and/or the clinical severity of the disease reduced, the immunogenic composition is described as a "vaccine.

In one aspect of the present invention the immunogenic composition comprises a pharmaceutically acceptable carrier.

The term "pharmaceutical-acceptable carrier" includes any and all solvents, dispersion media, coatings, stabilizing agents, diluents, preservatives, antibacterial and antifungal agents, isotonic agents, adsorption delaying agents, adjuvants, immune stimulants, and combinations thereof.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

In one aspect of the present invention the pharmaceutically acceptable carrier is phosphate buffered saline.

Preferably, the immunogenic composition further comprises sucrose gelatin stabilizer.

In one aspect of the present invention the pharmaceutically acceptable carrier is chitosan.

Chitosan is a natural deacetylated polysaccharide from chitin in crustaceans (e.g., shrimp, crab), insects, and other invertebrates. Recently, Rauw et al. 2009 (Vet Immunol Immunop 134:249-258) demonstrated that chitosan enhanced the cellular immune response of live Newcastle disease vaccine and promoted its protective effect. Further, Wang et al., 2012 (Arch Virol (2012) 157:1451-1461) have shown results revealing the potential of chitosan as an adjuvant for use in a live attenuated influenza vaccine.

In one aspect of the invention, the immunogenic composition can further include one or more other immunomodulatory agents such as, e.g. interleukins, interferons, or other cytokines. The amounts and concentrations of adjuvants and additives useful in the context of the present invention can readily be determined by the skilled artisan.

In some aspects, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.), John Wiley and Sons, NY, pp 51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of Carbopol 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from E. coli (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant can be added in an amount of about 100 μg to about 10 mg per dose, preferably in an amount of about 100 μg to about 10 mg per dose, more preferably in an amount of about 500 μg to about 5 mg per dose, even more preferably in an amount of about 750 μg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

In one aspect of the present invention the immunogenic composition is effective in the treatment and/or prophylaxis of clinical signs caused by IBV in a subject of need. The terms "treatment and/or prophylaxis", "clinical signs" and "of need" have been defined elsewhere.

In one aspect of the present invention the immunogenic composition protects against a homologous challenge. The terms "protects" and "prophylaxis" and "preventing" are used interchangeable in this application. However, these terms have been defined elsewhere.

In one aspect of the present invention the immunogenic composition protects against a challenge with M41.

In one aspect of the present invention the immunogenic composition is formulated for a single-dose administration.

The volume for a single-dose has been defined elsewhere herein.

It has furthermore been shown that one dose of the immunogenic composition of the present invention is effective after the administration of such single dose of such immunogenic composition.

In one aspect of the present invention the immunogenic composition is administered subcutaneously, intramuscularly, oral, in ovo, via spray, via drinking water or by eye drop.

In one aspect of the present invention the immunogenic composition comprises 1 to 10 $\log_{10}$ EID50/ml per dose of the IBV.

In one aspect of the present invention the immunogenic composition comprises 2 to 5 $\log_{10}$ EID50/ml per dose of the IBV.

In one aspect of the present invention the immunogenic composition comprises 2 to 4 $\log_{10}$ EID50/ml per dose of the IBV.

Kits

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration preferably for administration to subjects, especially poultry. Associated with such container(s) can be a notice in the form prescribed by a governmental agency regulating the manufacture, use or sale of pharmaceuticals or biological products, which notice reflects approval by the agency of manufacture, use or sale for human administration.

Thus, one embodiment of the present invention provides a kit comprising the IBV or the immunogenic composition as described herein.

In one aspect of the present invention the kit further comprises an instruction letter for the treatment and/or prophylaxis of diseases of avians.

In one aspect of the present invention the kit further comprises an instruction letter for the treatment and/or prophylaxis of diseases of poultry.

In one aspect of the present invention the kit further comprises an instruction letter for the treatment and/or prophylaxis of IB (infectious bronchitis).

Method of Treatments

Further, the present invention provides a method for immunizing a subject comprising administering to such subject an immunogenic composition as described herein.

The term "immunizing" relates to an active immunization by the administration of an immunogenic composition to a subject to be immunized, thereby causing an immunological response against the antigen included in such immunogenic composition.

Preferably, immunization results in lessening of the incidence of the particular IBV infection in a flock or in the reduction in the severity of clinical signs caused by or associated with the particular IBV infection.

Further, the immunization of a subject in need with the immunogenic compositions as provided herewith, results in preventing infection of a subject by IBV infection. Even more preferably, immunization results in an effective, long-lasting, immunological-response against IBV infection. It will be understood that the said period of time will last more than 1 month, preferably more than 2 months, preferably more than 3 months, more preferably more than 4 months, more preferably more than 5 months, more preferably more than 6 months. It is to be understood that immunization may not be effective in all subjects immunized. However, the term requires that a significant portion of subjects of a flock are effectively immunized.

Preferably, a flock of subjects is envisaged in this context which normally, i.e. without immunization, would develop clinical signs normally caused by or associated with a IBV infection. Whether the subjects of a flock are effectively immunized can be determined without further ado by the person skilled in the art. Preferably, the immunization shall be effective if clinical signs in at least 33%, at least 50%, at least 60%, at least 70%, at least 80%, at least 90%, still more preferably in at least 95% and most preferably in 100% of the subjects of a given flock are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not immunized or immunized with an immunogenic composition that was available prior to the present invention but subsequently infected by the particular IBV.

Further, the present invention provides a method of treating or preventing clinical signs caused by IBV in a subject of need, the method comprising administering to the subject a therapeutically effective amount of an immunogenic composition as described herein.

The term "treatment and/or prophylaxis" refers to the lessening of the incidence of the particular IBV infection in a flock or the reduction in the severity of clinical signs caused by or associated with the particular IBV infection. Thus, the term "treatment and/or prophylaxis" also refers to the reduction of the number of subjects in a flock that become infected with the particular IBV (=lessening of the incidence of the particular IBV infection) or to the reduction of the severity of clinical signs normally associated with or caused by a IBV infection or the reduction of virus shedding after infection with the particular IBV or preventing or lessening egg drop in laying hens after infection with the particular IBV in a group of subjects which subjects have received an effective amount of the immunogenic composition as provided herein in comparison to a group of subjects which subjects have not received such immunogenic composition.

The "treatment and/or prophylaxis" generally involves the administration of an effective amount of the immunogenic composition of the present invention to a subject or flock of subjects in need of or that could benefit from such a treatment/prophylaxis. The term "treatment" refers to the administration of the effective amount of the immunogenic composition once the subject or at least some subjects of the flock is/are already infected with such IBV and wherein such subjects already show some clinical signs caused by or associated with such IBV infection. The term "prophylaxis" refers to the administration of a subject prior to any infection of such subject with IBV or at least where such subject or none of the subjects in a group of subjects do not show any clinical signs caused by or associated with the infection by such IBV. The terms "prophylaxis" and "preventing" are used interchangeable in this application.

The term "an effective amount" as used herein means, but is not limited to an amount of antigen, that elicits or is able to elicit an immune response in a subject. Such effective amount is able to lessen the incidence of the particular IBV infection in a flock or to reduce the severity of clinical signs of the particular IBV infection.

In one aspect of the invention, clinical signs are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not treated or treated with an immunogenic composition that was available prior to the present invention but subsequently infected by the particular IBV.

The term "clinical signs" as used herein refers to signs of infection of a subject from IBV. The clinical signs of infection depend on the pathogen selected. Examples for such clinical signs include but are not limited to respiratory distress, nephritis, salphingitis, abnormal egg production, ruffled feathers, depression, reduced growth rates and reduced appetite. Signs of respiratory distress encompass respiratory signs including gasping, coughing, sneezing, tracheal rales, nasal and ocular discharge, tracheal lesions and ciliostasis in the trachea. Signs of nephritis encompass kidney lesions and watery diarrhea. Signs of abnormal egg production encompass egg drop, eggs of smaller size, inferior shell, reduced internal egg quality, eggs with thin albumen and ciliostasis in the oviduct. However, the clinical signs also include but are not limited to clinical signs that are directly observable from a live animal. Examples for clinical signs that are directly observable from a live animal include nasal and ocular discharge, coughing, gasping, sneezing, tracheal rales, ruffled feathers, conjunctivitis, weight loss, reduced growth rates, reduced appetite, dehydration, watery diarrhea, lameness, lethargy, wasting and unthriftiness and the like.

In one aspect of the invention, the clinical signs lessened in incidence or severity in a treated subject compared to subjects that are either not treated or treated with an immunogenic composition that was available prior to the present invention but subsequently infected by the particular IBV refer to a reduction of ciliostasis, a reduction of rales, a reduction of egg drop, a reduction of kidney lesions, a reduction of watery diarrhea, a reduction in weight loss, a lower virus load, a reduced viral shedding, or combinations thereof.

The term "in need" or "of need", as used herein means that the administration/treatment is associated with the boosting or improvement in health or clinical signs or any other positive medicinal effect on health of the subjects which receive the immunogenic composition in accordance with the present invention.

The term "reducing" or "reduced" or "reduction" or lower" are used interchangeable in this application. The term "reduction" means, that the clinical sign is reduced by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, even more preferably by at least 90%, still more preferably by at least 95% most preferably by 100% in comparison to subjects that are not treated (not immunized) but subsequently infected by the particular IBV.

Further, one embodiment of the present invention provides a method of reducing the ciliostasis in a subject of need, in comparison to a subject of a non-immunized control group of the same species, the method comprising administering to the subject a therapeutically effective amount of an immunogenic composition as described herein.

As shown in the Examples, the immunogenic composition as provided herein has been proven to be efficacious in reducing ciliostasis.

The term "ciliostasis" refers to a reduced movement of the cilia in the trachea. Thus, ciliostasis may be determined by examining the inner lining of the tracheal rings for the movement of the cilia. It is in the general knowledge of a person skilled in the art how to determine the movement of the cilia in the trachea.

In one aspect of the invention, the movement of the cilia is not reduced from day 10 after challenge or infection, more preferably from day 5 after challenge or infection, more preferably from day 4 after challenge or infection, more preferably from day 3 after challenge or infection and most preferably from day 1 or 2 after challenge or infection with the IBV as compared to a subject of a non-immunized control group of the same species.

The term "reduction of ciliostasis" means, that the ciliostasis is reduced by at least 10%, preferably by at least 20%, more preferably by at least 30%, even more preferably by at least 40%, even more preferably by at least 50%, even more preferably by at least 60%, even more preferably by at least 70%, even more preferably by at least 80%, even more preferably by at least 90%, even more preferably by at least 95% and most preferably by 100% as compared to a subject of a non-immunized control group of the same species. It is in the general knowledge of a person skilled in the art how to measure the reduction of the ciliostasis.

In one aspect of the present invention said subject is avian.

The term "avian" is well known to the person skilled in the art. The term "avian" encompasses all birds including poultry.

In one aspect of the present invention said subject is poultry.

The term "poultry" is well known to the person skilled in the art. The term "poultry" encompasses chickens, turkeys, quails, pheasants, guineafowl, geese, and ducks. Further, the term "chicken" includes broiler, laying hens, and reproductive stocks for both also referred to as breeders.

In one aspect of the present invention said subject is selected from the list consisting of chicken, turkey, quail, or pheasant.

In one aspect of the present invention the immunogenic composition is administered once.

It is understood, that a single-dose is administered only once. As shown in the Examples the immunogenic composition as provided herein has been proven to be efficacious after the administration of a single dose to a subject of need.

The dose volume per poultry depends on the route of vaccination and the age of the poultry.

Typically, eye drop vaccines are administered in a volume of 1 to 100 μl per dose at any age. Preferably, the single-dose for eye drop vaccines has a total volume between about 5 μl and 70 μl and more preferably between about 20 μl and 50 μl with a single 20 μl, 25 μl, 30 μl, 35 μl, 40 μl, 45 μl or 50 μl dose being preferred. Most preferred, the single-dose for eye drop vaccines has a total volume between about 30 μl and 50 μl with a single 30 μl, 35 μl, 40 μl, 45 μl or 50 μl dose being preferred.

Spray vaccines may contain the dose in a volume of 25 to 1000 μl for day-old poultry. Preferably, the single-dose for spray vaccines has a total volume between about 50 μl and 5000 more preferably between about 75 μl and 2000 more preferably between about 100 μl and 1000 even more preferably between about 200 μl and 900 even more preferably between about 300 μl and 800 μl and even more preferably between about 400 μl and 700 μl with a single 400 μl, 425 μl, 450 μl, 475 μl, 500 μl, 525 μl, 550 μl, 575 μl, 600 μl, 625 Ξl, 650 μl, 675 μl or 700 μl dose being preferred. Most preferred the single-dose has a total volume of 400 μl, 450 μl, 500 μl, 550 μl, 600 μl, 650 μl or 700 μl.

The vaccine for in ovo vaccination may contain the dose in a volume of 50 to 100 preferably 50 Preferably, the single-dose for in ovo vaccines has a total volume between about 10 µl and 250 more preferably between about 15 µl and 200 even more preferably between about 20 µl and 150 even more preferably between about 30 µl and 100 even more preferably between about 30 µl and 75 µl and with a single 30 µl, 35 µl, 45 µl, 50 µl, 55 µl, 60 µl, 65 µl, 70 µl or 75 µl dose being preferred. Most preferred the single-dose has a total volume of 40 µl, 45 µl, 50 µl, 55 µl or 60 µl.

The vaccine for intramuscular or subcutaneous vaccination or one dose of a drinking water vaccine may contain the dose in a volume of 30 µl to 1000 µl. Preferably, the single-dose has a total volume between about 30 µl and 1000 µl, more preferably between about 50 µl and 500 µl, more preferably between about 75 µl and 250 µl and even more preferably between about 100 µl and 200 µl with a single 100 µl, 110 µl, 120 µl, 125 µl, 130 µl, 135 µl, 140 µl, 145 µl, 150 µl, 160 µl, 170 µl, 175 µl, 180 µl, 190 µl, 155 µl, or 200 µl dose being the most preferred.

In one aspect of the present invention the immunogenic composition is administered at two or more doses.

However, the immunogenic composition can be administered at two or more doses, with a first dose being administered prior to the administration of a second (booster) dose.

In one aspect of the two-time administration regimen, both the first and second doses of the immunogenic composition are administered in the same amount. Preferably, each dose is in the preferred amounts specified above. In addition to the first and second dose regimen, an alternate embodiment comprises further subsequent doses. For example, a third, fourth, or fifth dose could be administered in these aspects. Preferably, subsequent third, fourth, and fifth dose regimens are administered in the same amount as the first dose, with the time frame between the doses being consistent with the timing between the first and second doses mentioned above.

In one aspect of the invention, the first administration of the vaccine is performed within the first three weeks of age, more preferably within the first week of age and most preferred at one day-of-age by methods as described below. A second administration can be performed within the first 20 weeks of age, preferably within 16-18 weeks of age, more preferably between 6-12 weeks of age. Exemplary the initial (first) vaccination is performed at 1-10 days of age and the second vaccination (booster) is performed with a live or inactivated vaccine at 6-12 or 16-18 weeks of age. More preferably, the initial (first) vaccination is performed at one day-of-age and the second vaccination (booster) is performed with a live or inactivated vaccine at 6-12 or 16-18 weeks of age.

In case in ovo vaccination is used, in one non-limiting embodiment, the first administration is performed when embryos are between 15 to 19 days old, preferably at day 17, 18 or 19, most preferably at day 18 of age. A second administration can be performed within the first three weeks of age, preferably within the first 10 days of age.

In one aspect of the present invention said immunogenic composition is administered subcutaneously, intramuscularly, oral, in ovo, via spray, via drinking water or by eye drop.

The immunogenic composition is, in one non-limiting embodiment, administered topically or systemically. Suitable routes of administration conventionally used are oral or parenteral administration, such as intranasal, intravenous, intradermal, transdermal, intramuscular, intraperitoneal, subcutaneous, as well as inhalation, in ovo, via spray, via drinking water or by eye drop. However, depending on the nature and mode of action of a compound, the immunogenic composition may be administered by other routes as well. For example, such other routes include intracutaneously, intravenously, intravascularly, intraarterially, intraperitoneally, intrathecally, intratracheally, intracutaneously, intracardially, intralobally, intralobarly, intramedullary, intrapulmonarily, intrarectally, and intravaginally. However, most preferred the immunogenic composition is administered subcutaneously, intramuscularly, oral, in ovo, via spray, via drinking water or by eye drop.

Live IBV vaccines are in one embodiment administered individually by eye drop, intranasal, intramuscular or subcutaneous.

In another embodiment of the invention, mass application methods, including drinking water and aerosol spray vaccination, are used. Also preferred is the use of vaccines as embryo vaccines (so-called in ovo vaccines) as described further below.

For example, broilers may be vaccinated at one-day of age or at 1-3 weeks of age, particularly for broilers with high levels of MDA. Laying stock or reproduction stock may be vaccinated initially at 1-10 days of age and boosted with the vaccine at 7-12 or 16-18 weeks of age.

In Ovo Administration

As outlined above, in one embodiment the present invention also provides an IBV vaccine that can be safely administered via the in ovo route and at the same time is able to induce a protective immune response. The in ovo administration is well known to the person skilled in the art and the person skilled in the art can perform in ovo administration without further ado. The in ovo administration of the vaccine involves the administration of the vaccine to an avian embryo while contained in the egg (for a review on in ovo vaccination see: Ricks et al., Advances in Vet. Med. 495-515, 1999). The vaccine may be administered to any suitable compartment of the egg (e. g. allantois fluid, yolk sac, amnion, air cell or into the embryo) as described in the art (Sharma; Am. J. Vet. Res. 45 1619-1623, 1984). Preferably the vaccine is administered below the shell (aircell) membrane and chorioallantoic membrane.

In one aspect of the present invention, the vaccine is injected into embryonated eggs during late stages of the embryonation, generally during the final quarter of the incubation period, preferably 3-4 days prior to hatch. In another aspect, the administration is performed when embryos are between 15 to 19 days old, for example at day 17, 18 or 19, or in another example at day 18 of age. Subsequently, the vaccinated embryonated eggs are transferred to an incubator for hatch. The process of in ovo administration can be automated using a robotic injection process as described in the prior art.

Usually conventional vaccines for post-hatch vaccination of poultry cannot be used for in ovo vaccination, because late stage embryos are highly susceptible to infection with most vaccine viruses examined. However, International patent application WO 01/64244 discloses that IBV vaccines can be used for in ovo administration provided it is applied at a very low doses. Further, Wakenell et al. 1986 (Am. J. Vet. Res., 47 933-938) discloses that passaging an IB vaccine virus in tissue culture rendered the virus apathogenic for embryos.

In one aspect of the present invention said immunogenic composition is administered via eye drop.

Typically, the live vaccine for post-hatch administration comprises the attenuated IBV in a concentration of $10^1$ to $10^8$ $EID_{50}$ (50% Egg Infective Dose) per unit dose, preferably in a concentration of $10^2$ to $10^5$ $EID_{50}$ per unit dose and, more preferably, in a concentration of $10^2$ to $10^4$ $EID_{50}$ per unit dose and, even more preferably, in a concentration of $10^2$ to $10^3$ $EID_{50}$ per unit dose.

The live vaccine for in ovo administration typically comprises an amount of the attenuated IBV of $10^2$ to $10^7$ $EID_{50}$/embryo, preferably $10^2$ to $10^3$ $EID_{50}$/embryo in a volume of 50 to 100 µl, preferably 50 µl.

In one aspect of the invention, the immunogenic composition of the present invention comprises the IBV of the present invention in amounts of about 1 to about 10 $\log_{10}$ EID (egg infective dose)$_{50}$/ml per dose, preferably about 2 to about 8 $\log_{10}$ $EID_{50}$/ml per dose, preferably in an amount of about 2 to about 7 $\log_{10}$ $EID_{50}$/ml per dose, more preferably in an amount of about 2 to about 6 $\log_{10}$ $EID_{50}$/ml per dose, even more preferably in an amount of about 2 to about 5 $\log_{10}$ $EID_{50}$/ml per dose, even more preferably in an amount of about 2 to about 4 $\log_{10}$ $EID_{50}$/ml per dose, most preferably in an amount of about 2 to about 3 $\log_{10}$ $EID_{50}$/ml per dose. More preferably, the immunogenic composition of the present invention comprises the IBV of the present invention in amounts of about 1, 1.5, 2, 2.5, 3, 3.5, 4, 4.5, 5, 5.5, 6, 6.5, 7, 7.5 or $\log_{10}$ $EID_{50}$/ml per dose.

In one aspect of the present invention the immunogenic composition comprises 1 to 10 $\log_{10}$ $EID_{50}$/ml of the IBV.

In one aspect of the present invention the immunogenic composition comprises 2 to 5 $\log_{10}$ $EID_{50}$/ml of the IBV.

In one aspect of the present invention the immunogenic composition comprises 2 to 4 $\log_{10}$ $EID_{50}$/ml of the IBV.

In one aspect of the present invention the immunogenic composition is administered to subjects within the first week of age, within the first three days of age, within the first two days of age, or within the first day of age.

In one aspect, the subject to be immunized is 1, 2, 3, 4, 5, 6, 7, 8, 9, 10, 11, 12, 13, 14, 15, 16, 17, 18, 19, 20 or 21 days of age. As one embodiment of the invention, said subject to be immunized is 1, 2, 3, 4, 5, 6, 7, 8, 9, 10, 11, 12, 13 or 14 days of age. In another embodiment, said subject to be immunized is 1, 2, 3, 4, 5, 6 or 7 days of age.

However, it has to be understood that after vaccination of the subject being a few days of age, it does need several days for the immune system of the poultry to build up immunity against an IBV infection. Therefore, in one non-limiting example, the subjects are immunized within the first 24 h of age.

In one aspect of the present invention the immunogenic composition is administered to subjects within the first day of age. As shown in the Examples the immunogenic composition as provided herein has been proven to be safe and efficacious when administered to 1-day old poultry.

In one aspect of the present invention said method results in an improvement in an efficacy parameter selected from the group consisting of: prevention or reduction of ciliostasis, prevention or reduction of rales, prevention or reduction of egg drop, prevention or reduction of kidney lesions, prevention or reduction of watery diarrhea, prevention or reduction in weight loss, a lower virus load, a reduced viral shedding or combinations thereof, in comparison to a subject of a non-immunized control group of the same species.

The terms "treatment and/or prophylaxis" have been defined elsewhere, wherein the terms "prophylaxis" and "preventing" or "prevention" are used interchangeable in this application. Further, the terms "shedding" has been defined elsewhere, too.

The term "reducing", "reduced", "reduction" or "lower" means, that the efficacy parameter (ciliostasis, rales, egg drop, kidney lesions, watery diarrhea, weight loss, virus load, viral shedding) is reduced by at least 10%, preferably by at least 20%, more preferably by at least 30%, even more preferably by at least 40%, even more preferably by at least 50%, even more preferably by at least 60%, even more preferably by at least 70%, even more preferably by at least 80%, even more preferably by at least 90%, even more preferably by at least 95% and most preferably by 100% as compared to a subject of a non-immunized control group of the same species. It is in the general knowledge of a person skilled in the art how to measure the improvement in the efficacy parameters.

The term "virus load" is well known to the person skilled in that art. The term virus load is interchangeable used with the term viral titer herein. The virus load or virus titer is a measure of the severity of an active viral infection, and can be determined by methods known to the person skilled in the art. The determination can be based on the detection of viral proteins such as by antibody binding to the viral proteins and further detection or, alternatively, by detection of viral RNA by amplification methods such as RT-PCR. Monitoring of virion associated viral RNA in plasma by nucleic acid amplification methods is a widely used parameter to assess the status and progression of retroviral disease, and to evaluate the effectiveness of prophylactic and therapeutic interventions. Exemplary, the virus load or virus titer can be calculated by estimating the live amount of virus in an involved body fluid such as a number of RNA copies per milliliter of blood plasma.

The term "ciliostasis" is well known to the person skilled in that art. The surface of the trachea is covered with specialized epithelial cells, which are lined with numerous, motile, hair-like structures called cilia. The term "ciliostasis" encompasses the reduction or loss of cilia and/or loss or partial loss of ciliary activity. Ciliostasis can be determined without further ado by the person skilled in the art.

The term "rales" is well known to the person skilled in that art. However, the term "rales" encompasses tracheal rales and refers to sounds emanating from the bronchi. Rales can be determined without further ado by the person skilled in the art.

The term "egg drop" is well known to the person skilled in that art. The term "egg drop" encompasses a decreased egg production.

In one aspect of the present invention the treatment or prevention results in a prevention or reduction of ciliostasis as compared to subjects of a non-treated control group of the same species.

In one aspect of the present invention the treatment or prevention results in a prevention or reduction of kidney lesions as compared to subjects of a non-treated control group of the same species.

In one aspect of the present invention the treatment or prevention results in a prevention or reduction of egg drop as compared to subjects of a non-treated control group of the same species.

In one embodiment the present invention further provides an IBV or an immunogenic composition as described herein for therapeutic use.

One embodiment of the present invention further provides an IBV or an immunogenic composition as described herein for use as an immunogen or vaccine.

One embodiment of the present invention further provides an IBV or an immunogenic composition as described herein for use as a medicament.

One embodiment of the present invention further provides the use of the IBV or immunogenic composition as described herein for the manufacture of a medicament.

One embodiment of the present invention further provides the use of the IBV or immunogenic composition as described herein for the treatment and/or prophylaxis of IBV infections in a subject.

Further, it has to be understood that a single inactivation of ORF 3a or a single inactivation of ORF 3b or a single inactivation of ORF 5a or a single inactivation of ORF 5b leads to the attenuation of the IBV as well. Therefore, an IBV having a single inactivation of ORF 3a or a single inactivation of ORF 3b or a single inactivation of ORF 5a or a single inactivation of ORF 5b can be used for preparing an immunogenic composition. Furthermore, such an immunogenic composition has the effect as described herein (such as protection against IBV challenge infection).

Furthermore, when generating such single inactivation (ORF 3a or ORF 3b or ORF 5a or ORF 5b) it has to be understood that a sequence comprising stop codons can be inserted downstream of an ORF to ensure the stop of the translation of said ORF. This may be necessary when two ORF's are overlapping and the inactivation of one ORF may inactivate the stop codon of the other ORF.

EMBODIMENTS

The following clauses are also described herein:
1. An IBV (infectious bronchitis virus), wherein:
the ORF 3a and ORF 3b are inactivated; or
the ORF 5a and ORF 5b are inactivated; or
the ORF 3a and ORF 3b and the ORF 5a and ORF 5b are inactivated.
2. An immunogenic composition comprising an IBV (infectious bronchitis virus), wherein:
the ORF 3a and ORF 3b are inactivated; or
the ORF 5a and ORF 5b are inactivated; or
the ORF 3a and ORF 3b and the ORF 5a and ORF 5b are inactivated.
3. The IBV of clause 1 or the immunogenic composition of clause 2, wherein said inactivation of ORF 3a and ORF 3b does not affect the expression of ORF 3c and/or not the activity of the E protein.
4. The IBV or the immunogenic composition of any one of clauses 1 to 3, wherein said inactivation of ORF 3a and ORF 3b does not affect the expression of ORF S and/or not the activity of the S protein.
5. The IBV or the immunogenic composition of any one of clauses 1 to 4, wherein said inactivation of ORF 5a and ORF 5b does not affect the expression of ORF N and/or not the activity of the N protein.
6. The IBV or the immunogenic composition of any one of clauses 1 to 5, wherein said inactivation is a complete or partial deletion of the ORF 3a and a partial deletion of ORF 3b and/or a complete or partial deletion of the ORF 5a and a partial deletion of ORF 5b, a complete or partial truncation of the ORF 3a and a partial truncation of ORF 3b and/or a complete or partial truncation of the ORF 5a and a partial truncation of ORF 5b, a complete or partial inversion of the ORF 3a and a partial inversion of ORF 3b and/or a complete or partial inversion the ORF 5a and a partial inversion of ORF 5b, a complete or partial relocation of the ORF 3a and a partial relocation of ORF 3b and/or a complete or partial relocation of the ORF 5a and a partial relocation of ORF 5b, an insertion of nucleic acids within the ORF 3a and ORF 3b and/or the ORF 5a and ORF 5b, a substitution of nucleic acids within the ORF 3a and ORF 3b and/or the ORF 5a and ORF 5b.
7. The IBV or the immunogenic composition of any one of clauses 1 to 6, wherein the ORF 3a is complete or partially deleted, substituted or inverted and wherein the ORF 3b is partially deleted, substituted or inverted.
8. The IBV or the immunogenic composition of any one of clauses 1 to 7, wherein the ORF 5a is complete or partially deleted, substituted or inverted and wherein the ORF 5b is partially deleted, substituted or inverted.
9. The IBV or the immunogenic composition of any one of clauses 1 to 8, wherein the ORF 3a and the ORF 5a are complete or partially deleted, substituted or inverted and wherein the ORF 3b and the ORF 5b are partially deleted, substituted or inverted.
10. The IBV or the immunogenic composition of any one of clauses 1 to 9, wherein the ORF 3a is complete or partially deleted and the ORF 3b is partially deleted.
11. The IBV or the immunogenic composition of any one of clauses 1 to 10, wherein the ORF 5a is complete or partially deleted and the ORF 5b is partially deleted.
12. The IBV or the immunogenic composition of any one of clauses 1 to 11, wherein the ORF 3a and the ORF 5a are complete or partially deleted and the ORF 3b and the ORF 5b are partially deleted.
13. The IBV or the immunogenic composition of any one of clauses 1 to 12, wherein the start codon of ORF 3a and the start codon of ORF 3b are inactivated.
14. The IBV or the immunogenic composition of any one of clauses 1 to 13, wherein the start codon of ORF 3a (AUG, nucleotides 1-3 of SEQ ID NO:1) and the start codon of ORF 3b (AUG, nucleotides 174-176 of SEQ ID NO:1) are inactivated.
15. The IBV or the immunogenic composition of clause 13 or clause 14, wherein said inactivation of the start codon (AUG) of ORF 3a and ORF 3b is a deletion, substitution or inversion.
16. The IBV or the immunogenic composition of any one of clauses 1 to 15, wherein the start codon of ORF 5a and the start codon of ORF 5b are inactivated.
17. The IBV or the immunogenic composition of any one of clauses 1 to 16, wherein the start codon of ORF 5a (AUG, nucleotides 1-3 of SEQ ID NO:2) and the start codon (AUG, nucleotides 195-197 of SEQ ID NO:2) of ORF 5b are inactivated.
18. The IBV or the immunogenic composition of clause 16 or clause 17, wherein said inactivation of the start codon (AUG) of ORF 5a and ORF 5b is a deletion, substitution or inversion.
19. The IBV or the immunogenic composition of any one of clauses 1 to 18, wherein the ORF 3a and ORF 3b are truncated from the 5'-Terminus of the start codon (AUG, nucleotides 1-3 of SEQ ID NO:1) of ORF 3a and ORF 3b (AUG, nucleotides 174-176 of SEQ ID NO:1).
20. The IBV or the immunogenic composition of any one of clauses 1 to 19, wherein the ORF 3a and ORF 3b are truncated from the A, U, or G of the start codon (AUG, nucleotides 1-3 of SEQ ID NO:1) of ORF 3a and ORF 3b (AUG, nucleotides 174-176 of SEQ ID NO:1).
21. The IBV or the immunogenic composition of any one of clauses 1 to 20, wherein the ORF 5a and ORF 5b are truncated from the 5'-Terminus of the start codon of ORF 5a (AUG, nucleotides 1-3 of SEQ ID NO:2) and ORF 5b (AUG, nucleotides 195-197 of SEQ ID NO:2).
22. The IBV or the immunogenic composition of any one of clauses 1 to 21, wherein the ORF 5a and ORF 5b are truncated from the A, U, or G of the start codon of ORF 5a (AUG, nucleotides 1-3 of SEQ ID NO:2) and ORF 5b (AUG, nucleotides 195-197 of SEQ ID NO:2).

23. The IBV or the immunogenic composition of any one of clauses 1 to 22, wherein the ORF 3a and ORF 3b are truncated from the 5'-Terminus of the start codon (AUG) of ORF 3a (AUG, nucleotides 1-3 of SEQ ID NO:1) and the start codon of ORF 3b (AUG, nucleotides 174-176 of SEQ ID NO:1) and wherein the ORF 5a and ORF 5b are truncated from the 5'-Terminus of the start codon of ORF 5a (AUG, nucleotides 1-3 of SEQ ID NO:2) and the start codon ORF 5b (AUG, nucleotides 195-197 of SEQ ID NO:2).

24. The IBV or the immunogenic composition of any one of clauses 1 to 23, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides from the 5'-Terminus of the start codon (AUG, nucleotides 1-3 of SEQ ID NO:1) of the ORF 3a are deleted, substituted or inverted, and, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides from the 5'-Terminus of the start codon (AUG, nucleotides 174-176 of SEQ ID NO:1) of the ORF 3b are deleted, substituted or inverted.

25. The IBV or the immunogenic composition of any one of clauses 1 to 24, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides from the A, U, or G of the start codon (AUG, nucleotides 1-3 of SEQ ID NO:1) of the ORF 3a are deleted, substituted or inverted, and, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides from the A, U, or G of the start codon (AUG, nucleotides 174-176 of SEQ ID NO:1) of the ORF 3b are deleted, substituted, or inverted.

26. The IBV or the immunogenic composition of any one of clauses 1 to 25, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides from the 5'-Terminus of the start codon (AUG, nucleotides 1-3 of SEQ ID NO:2) of the ORF 5a are deleted, substituted, or inverted and, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides from the 5'-Terminus of the start codon (AUG, nucleotides 195-197 of SEQ ID NO:2) of the ORF 5b are deleted, substituted, or inverted.

27. The IBV or the immunogenic composition of any one of clauses 1 to 26, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides from the A, U, or G of the start codon (AUG, nucleotides 1-3 of SEQ ID NO:2) of the ORF 5a are deleted, substituted, or inverted and, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides from the A, U, or G of the start codon (AUG, nucleotides 195-197 of SEQ ID NO:2) of the ORF 5b are deleted, substituted or inverted.

28. The IBV or the immunogenic composition of any one of clauses 1 to 27, wherein between 1 and 173 nucleotides from the 5'-Terminus of the start codon (AUG, nucleotides 1-3 of SEQ ID NO:1) of the ORF 3a are deleted, substituted or inverted, and, wherein between 1 and 175 nucleotides from the 5'-Terminus of the start codon (AUG, nucleotides 174-176 of SEQ ID NO:1) of the ORF 3b are deleted, substituted or inverted.

29. The IBV or the immunogenic composition of any one of clauses 1 to 28, wherein between 1 and 173 nucleotides from the A of the start codon (A of AUG, nucleotide 1 of SEQ ID NO:1) or between 1 and 172 nucleotides from the U of the start codon (U of AUG, nucleotide 2 of SEQ ID NO:1) or between 1 and 171 nucleotides from the G of the start codon (G of AUG, nucleotide 3 of SEQ ID NO:1) of the ORF 3a are deleted, substituted, or inverted and wherein between 1 and 175 nucleotides from the A of the start codon (A of AUG, nucleotide 174 of SEQ ID NO:1) or between 1 and 174 nucleotides from the U of the start codon (U of AUG, nucleotide 175 of SEQ ID NO:1) or between 1 and 173 nucleotides from the G of the start codon (G of AUG, nucleotide 176 of SEQ ID NO:1) of the ORF 3b are deleted, substituted, or inverted.

30. The IBV or the immunogenic composition of any one of clauses 1 to 29, wherein between 1 and 194 nucleotides from the 5'-Terminus of the start codon (AUG, nucleotides 1-3 of SEQ ID NO:2) of the ORF 5a are deleted, substituted or inverted and wherein between 1 and 191 nucleotides from the 5'-Terminus of the start codon (AUG, nucleotides 195-197 of SEQ ID NO:2) of the ORF 5b are deleted, substituted or inverted.

31. The IBV or the immunogenic composition of any one of clauses 1 to 30, wherein between 1 and 194 nucleotides from the A of the start codon (A of AUG, nucleotide 1 of SEQ ID NO:2) or between 1 and 193 nucleotides from the U of the start codon (U of AUG, nucleotide 2 of SEQ ID NO:2) or between 1 and 192 nucleotides from the G of the start codon (G of AUG, nucleotide 3 of SEQ ID NO:2) of the ORF 5a are deleted, substituted, or inverted, and, wherein between 1 and 191 nucleotides from the A of the start codon (A of AUG, nucleotide 195 of SEQ ID NO:2) or between 1 and 190 nucleotides from the U of the start codon (U of AUG, nucleotide 196 of SEQ ID NO:2) or between 1 and 189 nucleotides from the G of the start codon (G of AUG, nucleotide 197 of SEQ ID NO:2) of the ORF 5b are deleted, substituted, or inverted.

32. The IBV or the immunogenic composition of any one of clauses 1 to 31, wherein at least 174 nucleotides, at least 175 nucleotides, at least 176 nucleotides, at least 180, nucleotides, at least 190 nucleotides, at least 200 nucleotides, at least 225 nucleotides, at least 250 nucleotides, at least 300 nucleotides, at least 325 nucleotides, at least 340 nucleotides from the 5'-Terminus of the start codon (AUG, nucleotides 1-3 of SEQ ID NO:1) of ORF 3a are deleted, substituted, or inverted within the ORF 3a and ORF 3b.

33. The IBV or the immunogenic composition of any one of clauses 1 to 32, wherein at least 174 nucleotides, at least 175 nucleotides, at least 176 nucleotides, at least 180, nucleotides, at least 190 nucleotides, at least 200 nucleotides, at least 225 nucleotides, at least 250 nucleotides, at least 300 nucleotides, at least 325 nucleotides, at least 340 nucleotides from the A, U, or G of the start codon (AUG, nucleotides 1-3 of SEQ ID NO:1) of ORF 3a are deleted, substituted or inverted within the ORF 3a and ORF 3b.

34. The IBV or the immunogenic composition of any one of clauses 1 to 33, wherein at least 195 nucleotides, at least 196 nucleotides, at least 197 nucleotides, at least 200, nucleotides, at least 210 nucleotides, at least 220 nucleotides, at least 225 nucleotides, at least 250 nucleotides, at least 300 nucleotides, at least 325 nucleotides, at least 350 nucleotides, at least 380 nucleotides from the 5'-Terminus of the start codon (AUG, nucleotides 1-3 of SEQ ID NO:2) of ORF 5a are deleted, substituted, or inverted within the ORF 5a and ORF 5b.

35. The IBV or the immunogenic composition of any one of clauses 1 to 34, wherein at least 195 nucleotides, at least 196 nucleotides, at least 197 nucleotides, at least 200, nucleotides, at least 210 nucleotides, at least 220 nucleotides, at least 225 nucleotides, at least 250 nucleotides, at least 300 nucleotides, at least 325 nucleotides, at least 350 nucleotides, at least 380 nucleotides from the A, U, or G of the start codon (AUG, nucleotides 1-3 of SEQ ID NO:2) of ORF 5a are deleted, substituted, or inverted within the ORF 5a and ORF 5b.

36. The IBV or the immunogenic composition of any one of clauses 1 to 35, wherein between 174 and 200 nucleotides or between 174 and 300 nucleotides or between 174 and 348 nucleotides from the 5'-Terminus of the start codon (AUG, nucleotides 1-3 of SEQ ID NO:1) of ORF 3a are deleted, substituted, or inverted within the ORF 3a and ORF 3b.

37. The IBV or the immunogenic composition of any one of clauses 1 to 36, wherein between 174 and 348 nucleotides from the A of the start codon (A of AUG, nucleotide 1 of SEQ ID NO:1) or between 173 and 347 nucleotides from the U of the start codon (U of AUG, nucleotide 2 of SEQ ID NO:1) or between 172 and 346 nucleotides from the G of the start codon (G of AUG, nucleotide 3 of SEQ ID NO:1) of ORF 3a are deleted, substituted, or inverted within the ORF 3a and ORF 3b.

38. The IBV or the immunogenic composition of any one of clauses 1 to 37, wherein between 195 and 250 nucleotides or between 195 and 300 nucleotides or between 195 and 350 or between 195 and 385 nucleotides from the 5'-Terminus of the start codon (AUG, nucleotides 1-3 of SEQ ID NO:2) of the ORF 5a are deleted, substituted, or inverted within the ORF 5a and ORF 5b.

39. The IBV or the immunogenic composition of any one of clauses 1 to 38, wherein between 195 and 385 nucleotides from the A of the start codon (A of AUG, nucleotide 1 of SEQ ID NO:2) or between 194 and 384 nucleotides from the U of the start codon (U of AUG, nucleotide 2 of SEQ ID NO:2) or between 193 and 383 nucleotides from the G of the start codon (G of AUG, nucleotide 3 of SEQ ID NO:2) of the ORF 5a are deleted, substituted, or inverted within the ORF 5a and ORF 5b.

40. The IBV or the immunogenic composition of any one of clauses 1 to 39, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides of the ORF 3a are deleted, substituted, or inverted, and, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides of the ORF 3b are deleted, substituted, or inverted.

41. The IBV or the immunogenic composition of any one of clauses 1 to 40, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides of the ORF 5a are deleted, substituted, or inverted, and, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides of the ORF 5b are deleted, substituted, or inverted.

42. The IBV or the immunogenic composition of any one of clauses 1 to 41, wherein between 1 and 173 nucleotides of the ORF 3a are deleted, substituted, or inverted, and, wherein between 1 and 175 nucleotides of the ORF 3b are deleted, substituted, or inverted.

43. The IBV or the immunogenic composition of any one of clauses 1 to 42, wherein between 1 and 194 nucleotides of the ORF 5a are deleted, substituted or inverted, and, wherein between 1 and 191 nucleotides of the ORF 5b are deleted, substituted, or inverted.

44. The IBV or the immunogenic composition of any one of clauses 1 to 43, wherein between 176 and 348 nucleotides of the ORF 3a and ORF 3b are deleted, substituted or inverted within the 5'-Terminus of the start codon of the ORF 3a and the start codon of the ORF 3c.

45. The IBV or the immunogenic composition of any one of clauses 1 to 44, wherein between 176 and 348 nucleotides of the ORF 3a and ORF 3b are deleted, substituted or inverted within the 5'-Terminus of the start codon (AUG, nucleotides 1-3 of SEQ ID NO:1) of the ORF 3a to nucleotide 348 of SEQ ID NO:1.

46. The IBV or the immunogenic composition of any one of clauses 1 to 45, wherein at least 176 nucleotides, at least 180 nucleotides, at least 200 nucleotides, at least 225, nucleotides, at least 250 nucleotides, at least 300 nucleotides, at least 340 nucleotides of the ORF 3a and ORF 3b are deleted, substituted or inverted within the 5'-Terminus of the start codon of the ORF 3a and the start codon of the ORF 3c.

47. The IBV or the immunogenic composition of any one of clauses 1 to 46, wherein at least 176 nucleotides, at least 180 nucleotides, at least 200 nucleotides, at least 225, nucleotides, at least 250 nucleotides, at least 300 nucleotides, at least 340 nucleotides of the ORF 3a and ORF 3b are deleted, substituted or inverted within the 5'-Terminus of the start codon (AUG, nucleotides 1-3 of SEQ ID NO:1) of the ORF 3a to nucleotide 348 of SEQ ID NO:1.

48. The IBV or the immunogenic composition of any one of clauses 1 to 47, wherein between 195 and 385 nucleotides of the ORF 5a and ORF 5b are deleted, substituted, or inverted within the 5'-Terminus of the start codon of the ORF 5a and the start codon of the ORF N.

49. The IBV or the immunogenic composition of any one of clauses 1 to 48, wherein between 195 and 385 nucleotides of the ORF 5a and ORF 5b are deleted, substituted, or inverted within the 5'-Terminus of the start codon (AUG, nucleotides 1-3 of SEQ ID NO:2) of the ORF 5a to nucleotide 385 of SEQ ID NO:2.

50. The IBV or the immunogenic composition of any one of clauses 1 to 49, wherein at least 195 nucleotides, at least 200 nucleotides, at least 225 nucleotides, at least 250, nucleotides, at least 300 nucleotides, at least 350 nucleotides, at least 380 nucleotides of the ORF 5a and ORF 5b are deleted, substituted or inverted within the 5'-Terminus of the start codon of the ORF 5a and the start codon of the ORF N.

51. The IBV or the immunogenic composition of any one of clauses 1 to 50, wherein at least 195 nucleotides, at least 200 nucleotides, at least 225 nucleotides, at least 250, nucleotides, at least 300 nucleotides, at least 350 nucleotides, at least 380 nucleotides of the ORF 5a and ORF 5b are deleted, substituted or inverted within the 5'-Terminus of the start codon (AUG, nucleotides 1-3 of SEQ ID NO:2) of the ORF 5a to nucleotide 385 of SEQ ID NO:2.

52. The IBV or the immunogenic composition of any one of clauses 1 to 51, wherein the ORF 3a and ORF 3b from the 5'-Terminus of the start codon (AUG, nucleotides 1-3 of SEQ ID NO:1) of the ORF 3a to nucleotide 348 of SEQ ID NO:1 is deleted, substituted, or inverted.

53. The IBV or the immunogenic composition of any one of clauses 1 to 52, wherein the RNA sequence as set forth in SEQ ID NO:1 is deleted, substituted, or inverted within the ORF 3a and ORF 3b.

54. The IBV or the immunogenic composition of any one of clauses 1 to 53, wherein a RNA sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the RNA sequence as set forth in SEQ ID NO:1 is deleted, substituted, or inverted within the ORF 3a and ORF 3b.

55. The IBV or the immunogenic composition of any one of clauses 1 to 54, wherein the ORF 5a and ORF 5b from the 5'-Terminus of the start codon (AUG, nucleotides 1-3 of SEQ ID NO:2) of the ORF 5a to nucleotide 385 of SEQ ID NO:2 is deleted, substituted, or inverted.

56. The IBV or the immunogenic composition of any one of clauses 1 to 55, wherein the RNA sequence as set forth in SEQ ID NO:2 is deleted, substituted, or inverted within the ORF 5a and ORF 5b.

57. The IBV or the immunogenic composition of any one of clauses 1 to 56, wherein a RNA sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the RNA sequence as set forth in SEQ ID NO:2 is deleted, substituted, or inverted within the ORF 5a and ORF 5b.

58. The IBV or the immunogenic composition of any one of clauses 1 to 57, wherein the IBV is attenuated.

59. The IBV or the immunogenic composition of any one of clauses 1 to 58, wherein the IBV is genetically engineered.

60. The IBV or the immunogenic composition of any one of clauses 1 to 59, wherein the IBV is a recombinant IBV.

61. The IBV or the immunogenic composition of any one of clauses 1 to 60, wherein the IBV has a genotype selected from a list of strains containing of: Arkansas (such as Arkansas 99), California (such as California 1734/04, California 99), Connecticut, Delaware (such as Delaware 98), Dutch (such as D207, D212, D274, D3128, D3896, D8880, D1466), Florida, Georgia (such as Georgia GA-08, GA-12, GA-13), Gray, Holte, Iowa (such as Iowa 97 and Iowa 69), Italy (such as Italy 02), JMK, Maine (such as Maine 209), Massachusetts (such as M41, Beaudette, 246 G, D 580, H52, H120), Pennsylvania (such as Pennsylvania 1220/98, Pennsylvania Wolg/98), Qu, (such as Qu-mv), QX (such as GB341/96), Q1, SE 17, Variant 2 (such as IS/1494/06) and 4/91 (793B).

62. The IBV or the immunogenic composition of any one of clauses 1 to 61, wherein the IBV is of QX, Massachusetts, 4/91, Q1 or Italy 02 genotype.

63. The IBV or the immunogenic composition of clause 62, wherein the QX genotype is selected from a list containing of: FR-L1450T-05, FR-L1450L-05, NL-L1449T-04, NL-L1449K-04, IBV/Ck/SP/170/09, IBV/Ck/SP/79/08, IBV/Ck/SP/248/09, HBN, IBVQX, LX4, BJQ, CK/CH/LGD/03, GB341/96.

64. The IBV or the immunogenic composition of clause 62, wherein the Massachusetts genotype is selected from a list containing of: H120, H52, Spain/98/308, IBMA5-1, SD/97/01, Beaudette, Spain/96/334, M41-M21883.

65. The IBV or the immunogenic composition of clause 62, wherein the 4/91 genotype is selected from a list containing of: Spain/98/328, Spain/92/35, IR-3654-VM, FR-CR88061-88, FR-85131-85, UK-1233-95, UK/3/91, Spain/00/336, UK/7/91, 4/91-pathogenic, 4/91 attenuated, IB4-91.

66. The IBV or the immunogenic composition of clause 62, wherein the Q1 genotype is selected from a list containing of: CK/CH/LDL/98I, CK/CH/LSD/08-10, J2, Q1, AR08ER22, AR08BA21, Chile-295-10.

67. The IBV or the immunogenic composition of clause 62, wherein the Italy 02 genotype is selected from a list containing of: Spain/99/316, Italy-02, UK-L633-04, It-497-02, Spain/05/866, Spain/04/221, Spain/00/337, Spain/155/09, Spain/03/08.

68. The IBV or the immunogenic composition of any one of clauses 1 to 62, wherein the IBV is of the Massachusetts genotype strain H52.

69. The immunogenic composition of any one of clauses 2 to 68, wherein the immunogenic composition is a vaccine.

70. The immunogenic composition of any one of clauses 2 to 69, wherein the immunogenic composition comprises a pharmaceutically acceptable carrier.

71. The immunogenic composition of clause 70, wherein the pharmaceutically acceptable carrier is phosphate buffered saline.

72. The immunogenic composition of any one of clauses 2 to 71, wherein the immunogenic composition is effective in the treatment and/or prophylaxis of clinical signs caused by IBV in a subject of need.

73. The immunogenic composition of any one of clauses 2 to 72, wherein the immunogenic composition protects against a homologous challenge.

74. The immunogenic composition of any one of clauses 2 to 73, wherein the immunogenic composition protects against a challenge with M41.

75. The immunogenic composition of any one of clauses 2 to 74, wherein said immunogenic composition is formulated for a single-dose administration.

76. The immunogenic composition of any one of clauses 2 to 75, wherein said immunogenic composition is administered subcutaneously, intramuscularly, oral, in ovo, via spray, via drinking water or by eye drop.

77. The immunogenic composition of any one of clauses 2 to 76, wherein the immunogenic composition comprises 1 to 10 $\log_{10}$ $EID_{50}$ of the IBV.

78. The immunogenic composition of any one of clauses 2 to 77, wherein the immunogenic composition comprises 2 to 5 $\log_{10}$ $EID_{50}$ of the IBV.

79. The immunogenic composition of any one of clauses 2 to 78, wherein the immunogenic composition comprises 2 to 4 $\log_{10}$ $EID_{50}$ of the IBV.

80. A kit comprising the IBV or the immunogenic composition of any one of clauses 1 to 79.

81. The kit according to clause 80, wherein the kit further comprises an instruction letter for the treatment and/or prophylaxis of diseases of avians.

82. The kit according to clause 81, wherein the kit further comprises an instruction letter for the treatment and/or prophylaxis of diseases of poultry.

83. The kit according to clauses 82, wherein the kit further comprises an instruction letter for the treatment and/or prophylaxis of IB.

84. A method for immunizing a subject comprising administering to such subject an immunogenic composition according to any one of clauses 2 to 79.

85. A method of treating or preventing clinical signs caused by IBV in a subject of need, the method comprising administering to the subject a therapeutically effective amount of an immunogenic composition according to any one of clauses 2 to 79.

86. A method of reducing the ciliostasis in a subject of need, in comparison to a subject of a non-immunized control group of the same species, the method comprising administering to the subject a therapeutically effective amount of an immunogenic composition according to any one of clauses 2 to 79.

87. The immunogenic composition according to any one of clauses 2 to 79 for use in a method for immunizing a subject, the method comprising administering to the subject a therapeutically effective amount of said immunogenic composition.

88. The immunogenic composition according to any one of clauses 2 to 79 for use in a method of treating or preventing clinical signs caused by IBV in a subject of need, the method comprising administering to the subject a therapeutically effective amount of said immunogenic composition.

89. The immunogenic composition according to any one of clauses 2 to 79 for use in a method of reducing the ciliostasis in a subject of need, in comparison to a subject of a non-immunized control group of the same species, the method comprising administering to the subject a therapeutically effective amount of said immunogenic composition.

90. The method or use of any one of clauses 84 to 89, wherein said subject is avian.

91. The method or use of any one of clauses 84 to 90, wherein said subject is poultry.

92. The method or use of any one of clauses 84 to 91, wherein said subject is selected from the list consisting of chicken, turkey, quail, or pheasant.

93. The method or use of any one of clauses 84 to 92, wherein the immunogenic composition is administered once.

94. The method or use of any one of clauses 84 to 92, wherein the immunogenic composition is administered at two or more doses.

95. The method or use of any one of clauses 84 to 94, wherein said immunogenic composition is administered subcutaneously, intramuscularly, oral, in ovo, via spray, via drinking water or by eye drop.

96. The method or use of any one of clauses 84 to 95, wherein said immunogenic composition is administered via eye drop.

97. The method or use of any one of clauses 84 to 96, wherein the immunogenic composition comprises 1 to 10 $\log_{10}$ $EID_{50}$ of the IBV.

98. The method or use of any one of clauses 84 to 97, wherein the immunogenic composition comprises 2 to 5 $\log_{10}$ $EID_{50}$ of the IBV.

99. The method or use of any one of clauses 84 to 98, wherein the immunogenic composition comprises 2 to 4 $\log_{10}$ $EID_{50}$ of the IBV.

100. The method or use of any one of clauses 84 to 99, wherein the immunogenic composition is administered to subjects within the first week of age, within the first three days of age, within the first two days of age, or within the first day of age.

101. The method or use of any one of clauses 84 to 100, wherein the immunogenic composition is administered to subjects within the first day of age.

102. The method or use of any one of clauses 84 to 101, wherein said method results in an improvement in an efficacy parameter selected from the group consisting of: prevention or reduction of ciliostasis, prevention or reduction of rales, prevention or reduction of egg drop, prevention or reduction of kidney lesions, prevention or reduction of watery diarrhea, prevention or reduction in weight loss, a lower virus load, a reduced viral shedding or combinations thereof, in comparison to a subject of a non-treated control group of the same species.

103. The method or use of any one of clauses 84 to 102, wherein the treatment or prevention results in a prevention or reduction of ciliostasis as compared to subjects of a non-treated control group of the same species.

104. The method or use of any one of clauses 84 to 103, wherein the treatment or prevention results in a prevention or reduction of kidney lesions as compared to subjects of a non-treated control group of the same species.

105. The method or use of any one of clauses 84 to 104, wherein the treatment or prevention results in a prevention or reduction of egg drop as compared to subjects of a non-treated control group of the same species.

106. The IBV or immunogenic composition of any one of clauses 1 to 79 for therapeutic use.

107. The IBV or immunogenic composition of any one of clauses 1 to 79 for use as an immunogen or vaccine.

108. The IBV or immunogenic composition any one of clauses 1 to 79 for use as a medicament.

109. Use of the IBV or immunogenic composition of any one of clauses 1 to 79 for the manufacture of a medicament.

110. Use of the IBV or immunogenic composition of any one of clauses 1 to 79 for the treatment and/or prophylaxis of IBV infections in a subject.

Further, the Following Clauses are Also Described Herein:

1. A method of propagating and genomically modifying IBV comprising:
a) Transfecting viral RNA of an IBV into cells;
b) Co transfecting the cells from step a) with a first partial IBV viral RNA, wherein said first partial IBV viral RNA encodes a surface protein of a different coronavirus;
c) Selecting chimeric infectious IBV clones positive for said surface protein of the different coronavirus of said partial IBV viral RNA;
d) Transfecting a second partial IBV viral RNA into a cell line positive for an chimeric infectious IBV clone of step c), wherein said second partial IBV viral RNA encodes a surface protein of an IBV, and, wherein said second partial IBV viral RNA carries further modifications;
e) Inoculating the cells from step d) into embryonated avian eggs;
f) Selecting genomically modified IBV from the embryonated avian eggs of step e), wherein the genomically modified IBV has the surface protein of an IBV and, wherein the genomically modified IBV carries said further modifications.

2. The method of clause 1, wherein the IBV is of QX, Massachusetts, 4/91, Q1, or Italy 02 genotype.

3. The method of clause 1 or 2, wherein the IBV has a genotype selected from a list of strains containing of: Arkansas (such as Arkansas 99), California (such as California 1734/04, California 99), Connecticut, Delaware (such as Delaware 98), Dutch (such as D207, D212, D274, D3128, D3896, D8880, D1466), Florida, Georgia (such as Georgia GA-08), Gray, Holte, Iowa (such as Iowa 97 and Iowa 69), Italy (such as Italy 02), JMK, Maine (such as Maine 209), Massachusetts (such as M41, Beaudette, 246 G, D 580, H52, H120 correct?), Pennsylvania (such as Pennsylvania 1220/98, Pennsylvania Wolg/98), Qu, (such as Qu-mv), QX (such as GB341/96), Q1, SE 17, Variant 2 (such as IS/1494/06) and 4/91 (793B).

4. The method of any one of clauses 1 to 3, wherein transfecting is microinjection.

5. The method of any one of clauses 1 to 3, wherein transfecting is electroporation.

6. The method of anyone of clauses 1 to 5, wherein the transfection in step a) of clause 1 and the co-transfection in step b) of clause 1 is done simultaneously.

7. The method of anyone of clauses 1 to 6, wherein the cells have a mammalian, avian, or vertebrate origin.

8. The method of anyone of clauses 1 to 7, wherein the cells are selected from the group consisting of: BHK (baby hamster kidney)-21, Vero (African green monkey kidney epithelial cells), Cos-7 (African green monkey *Cercopithecus aethiops* fibroblast-like kidney cells), CK (chicken kidney), CEF (chicken embryo fibroblasts), chicken embryo liver cells (CELC), chicken embryo dermal cells (CED), Vero cells, and 293T cells.

9. The method of anyone of clauses 1 to 8, wherein the cells are co-cultivated with a second type of cells, wherein the second type of cells is originated from the same species than the species specificity is from said different coronavirus.

10. The method of clause 9, wherein the second type of cells for co-cultivation are cells originated from mouse, feline, swine, human, or turkey.

11. The method of clause 9 or 10, wherein the second type of cells for co-cultivation is mouse LR7, mouse L2R, mouse L2, mouse mTAL (mouse medullary thick ascending limb), feline FCWF (*Felis catus* whole fetus), ST (swine testis) or LLC-PK (Pig Kidney Epithelial cells).

12. The method of clause 9 or 10, wherein the second type of cells for co-cultivation is mouse LR7.

13. The method of anyone of clauses 1 to 12, wherein the co transfection step in step b) of clause 1 further comprises the co transfection of a RNA encoding a coronavirus nucleocapsid protein (N protein).

14. The method of clause 13, wherein the RNA encoding a coronavirus N gene is a RNA encoding the IBV N protein, the MHV N protein, the FIPV N protein or the SDCV N protein 15. The method of anyone of clauses 1 to 14, wherein the surface protein is a receptor binding protein or a part thereof.

16. The method of anyone of clauses 1 to 15, wherein the surface protein is a spike protein or a part thereof.

17. The method of anyone of clauses 1 to 16, wherein the surface protein is the ectodomain of the spike protein or a part thereof.

18. The method of anyone of clauses 1 to 17, wherein the surface protein of a different coronavirus of step b) of clause 1 is an MHV, FIPV, PEDV, or SDCV surface protein or a part thereof.

19. The method of anyone of clauses 1 to 17, wherein the surface protein of a different coronavirus of step b) of clause 1 is an MHV, FIPV, PEDV, or SDCV receptor binding protein or a part thereof.

20. The method of anyone of clauses 1 to 19, wherein the surface protein of a different coronavirus of step b) of clause 1 is an MHV, FIPV, PEDV, or SDCV spike protein or a part thereof.

21. The method of anyone of clauses 1 to 19, wherein the surface protein of a different coronavirus of step b) of clause 1 is an MHV, FIPV, PEDV, or SDCV ectodomain of a spike protein or a part thereof.

22. The method of any one of clauses 1 to 21, wherein said surface protein of a different coronavirus is from a coronavirus other than IBV.

23. The method of anyone of clauses 1 to 22, wherein said surface protein of a different coronavirus is a MHV spike protein or a part thereof.

24. The method of anyone of clauses 1 to 23, wherein said surface protein of a different coronavirus is the ectodomain of the MHV spike protein or a part thereof.

25. The method of anyone of clauses 1 to 24, wherein said chimeric infectious IBV clone comprises a spike protein or a part thereof of MHV, FIPV, PEDV, or SDCV.

26. The method of anyone of clauses 1 to 25, wherein said chimeric infectious IBV clone comprises the ectodomain of a spike protein or a part thereof of MHV, FIPV, PEDV, or SDCV.

27. The method of anyone of clauses 1 to 26, wherein said chimeric infectious IBV clone comprises a MHV spike protein or a part thereof.

28. The method of anyone of clauses 1 to 27, wherein said chimeric infectious IBV clone comprises the ectodomain of the MHV spike protein or a part thereof.

29. The method of anyone of clauses 1 to 28, wherein said embryonated avian egg is from chicken, turkey, quail, or pheasant.

30. The method of anyone of clauses 1 to 29, wherein said embryonated avian egg is a chicken egg.

31. The method of anyone of clauses 1 to 30, wherein selecting infectious IBV clones comprises a method selected from the group consisting of: RT-PCR, Real Time RT-PCR, Northern Blots, Western Blots, radioimmunoassay, ELISA assay, Immunofluorescence, Immunohistochemistry, in situ hybridization.

32. The method of anyone of clauses 1 to 31, wherein said partial IBV viral RNA is a recombinant viral RNA.

33. The method of anyone of clauses 1 to 32, wherein said partial IBV viral RNA is a synthetic viral RNA.

34. The method of anyone of clauses 1 to 33, wherein said second partial IBV viral RNA of clause 1 encodes an IBV spike protein or part thereof.

35. The method of anyone of clauses 1 to 34, wherein said second partial IBV viral RNA of clause 1 encodes the ectodomain of an IBV spike protein or part thereof.

36. The method of anyone of clauses 1 to 35, wherein said modification in said second partial IBV viral RNA is selected from the group consisting of: a complete deletion of a gene, ORF, promoter or any non-encoding sequence, a partial deletion of a gene, ORF, promoter or any non-encoding sequence, a truncation of a gene, ORF, promoter or any non-encoding sequence, an inversion of a gene, ORF, promoter or any non-encoding sequence, a relocation of a gene, ORF, promoter or any non-encoding sequence, an insertion of nucleic acids within a gene, ORF, promoter or any non-encoding sequence, a substitution of nucleic acids within a gene, ORF, promoter or any non-encoding sequence.

37. The method of anyone of clauses 1 to 36, wherein said modification in said second partial IBV viral RNA is a complete or partial deletion of the ORF 3a and a partial deletion of ORF 3b and/or a complete or partial deletion of the ORF 5a and a partial deletion of ORF 5b, a complete or partial truncation of the ORF 3a and a partial deletion of ORF 3b and/or a complete or partial truncation of the ORF 5a and a partial deletion of ORF 5b, a complete or partial inversion of the ORF 3a and a partial inversion of ORF 3b and/or a complete or partial inversion the ORF 5a and a partial inversion of ORF 5b, a complete or partial relocation of the ORF 3a and a partial relocation of ORF 3b and/or a complete or partial relocation of the ORF 5a and a partial relocation of ORF 5b, an insertion of nucleic acids within the ORF 3a and ORF 3b and/or the ORF 5a and ORF 5b, a substitution of nucleic acids within the ORF 3a and ORF 3b and/or the ORF 5a and ORF 5b.

38. The method of anyone of clauses 1 to 36, wherein said modification in said second partial IBV viral RNA is a complete or partial deletion, substitution or inversion of the ORF 3a and a partial deletion, substitution or inversion of the ORF 3b and/or a complete or partial deletion, substitution or inversion of the ORF 5a and a partial deletion, substitution or inversion of the ORF 5b.

39. The method of anyone of clauses 1 to 36, wherein said modification in said second partial IBV viral RNA is a truncation of the ORF 3a and ORF 3b and/or ORF 5a and ORF 5b.

40. The method of anyone of clauses 1 to 39, wherein selecting genomically modified IBV from the embryonated chicken eggs comprises a method selected from the group consisting of RT-PCR, Real Time RT-PCR, Northern Blots, Western Blots, radioimmunoassay, ELISA assay, Immunofluorescence Immunohistochemistry, In situ hybridization, end point dilution.

41. The method of anyone of clauses 1 to 40, wherein said genomically modified IBV is a recombinant IBV.

42. The method of anyone of clauses 1 to 41, wherein said genomically modified IBV is attenuated.

43. The method of anyone of clauses 1 to 42, wherein the selecting of said genomically modified coronavirus in embryonated chicken eggs is done by limited dilution.

44. A method of preparing an attenuated IBV vaccine comprising the method according to any one of clauses 1 to 43.

45. The method of clause 44 comprising admixing the attenuated IBV with a pharmaceutically acceptable carrier.

46. A cell comprising an IBV according to any one of clauses 1 to 43.

47. An embryonated avian egg comprising an IBV according to any one of clauses 1 to 43.

48. An embryonated chicken egg comprising an IBV according to any one of clauses 1 to 42.

49. An attenuated IBV obtained by the method according to any one of clauses 1 to 42.

Further, the Following Clauses Relating to an ORF 3a Inactivation are Also Described Herein:

1. An IBV (infectious bronchitis virus), wherein the ORF 3a is inactivated.

2. An immunogenic composition comprising an IBV (infectious bronchitis virus), wherein the ORF 3a is inactivated.

3. The IBV or the immunogenic composition of clause 1 or 2, wherein said inactivation of ORF 3a does not affect the expression of ORF S and/or not the activity of the S protein.

4. The IBV or the immunogenic composition of any one of clauses 1 to 3, wherein said inactivation of ORF 3a does not affect the expression of ORF 3b and/or not the activity of the 3b protein.

5. The IBV or the immunogenic composition of any one of clauses 1 to 4, wherein said inactivation is a complete or partial deletion of the ORF 3a, a complete or partial truncation of the ORF 3a, a complete or partial inversion of the ORF 3a, a complete or partial relocation of the ORF 3a, an insertion of nucleic acids within the ORF 3a, a substitution of nucleic acids within the ORF 3a.

6. The IBV or the immunogenic composition of any one of clauses 1 to 5, wherein the ORF 3a is partially deleted, substituted or inverted.

7. The IBV or the immunogenic composition of any one of clauses 1 to 6, wherein the ORF 3a is partially deleted.

8. The IBV or the immunogenic composition of any one of clauses 1 to 7, wherein the start codon of ORF 3a is inactivated.

9. The IBV or the immunogenic composition of any one of clauses 1 to 8, wherein the start codon of ORF 3a (AUG, nucleotides 1-3 of SEQ ID NO:1) is inactivated.

10. The IBV or the immunogenic composition of clause 8 or clause 9, wherein said inactivation of the start codon (AUG) of ORF 3a is a deletion, substitution, or inversion.

11. The IBV or the immunogenic composition of any one of clauses 1 to 10, wherein the ORF 3a is truncated from the 5'-Terminus of the start codon (AUG, nucleotides 1-3 of SEQ ID NO:1) of ORF 3a.

12. The IBV or the immunogenic composition of any one of clauses 1 to 11, wherein the ORF 3a is truncated from the A, U, or G of the start codon (AUG, nucleotides 1-3 of SEQ ID NO:1) of ORF 3a.

13. The IBV or the immunogenic composition of any one of clauses 1 to 12, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides from the 5'-Terminus of the start codon (AUG, nucleotides 1-3 of SEQ ID NO:1) of the ORF 3a are deleted, substituted, or inverted.

14. The IBV or the immunogenic composition of any one of clauses 1 to 13, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides from the A, U, or G of the start codon (AUG, nucleotides 1-3 of SEQ ID NO:1) of the ORF 3a are deleted, substituted, or inverted.

15. The IBV or the immunogenic composition of any one of clauses 1 to 14, wherein between 1 and 173 nucleotides from the 5'-Terminus of the start codon (AUG, nucleotides 1-3 of SEQ ID NO:1) of the ORF 3a are deleted, substituted, or inverted.

16. The IBV or the immunogenic composition of any one of clauses 1 to 15, wherein between 1 and 173 nucleotides from the A of the start codon (A of AUG, nucleotide 1 of SEQ ID NO:1) or between 1 and 172 nucleotides from the U of the start codon (U of AUG, nucleotide 2 of SEQ ID NO:1) or between 1 and 171 nucleotides from the G of the start codon (G of AUG, nucleotide 3 of SEQ ID NO:1) of the ORF 3a are deleted, substituted, or inverted.

17. The IBV or the immunogenic composition of any one of clauses 1 to 16, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides of the ORF 3a are deleted, substituted, or inverted.

18. The IBV or the immunogenic composition of any one of clauses 1 to 17, wherein between 1 and 173 nucleotides of the ORF 3a are deleted, substituted, or inverted.

19. The IBV or the immunogenic composition of any one of clauses 1 to 18, wherein the ORF 3a from the 5'-Terminus of the start codon (AUG, nucleotides 1-3 of SEQ ID NO:1) of the ORF 3a to nucleotide 173 of SEQ ID NO:1 is deleted, substituted, or inverted.

20. The IBV or the immunogenic composition of any one of clauses 1 to 19, wherein the RNA sequence as set forth in SEQ ID NO:33 is deleted, substituted, or inverted within the ORF 3a.

21. The IBV or the immunogenic composition of any one of clauses 1 to 20, wherein a RNA sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the RNA sequence as set forth in SEQ ID NO:33 is deleted, substituted or inverted within the ORF 3a.

22. The IBV or the immunogenic composition of any one of clauses 1 to 21, wherein the IBV is attenuated.

23. The IBV or the immunogenic composition of any one of clauses 1 to 22, wherein the IBV is genetically engineered.

24. The IBV or the immunogenic composition of any one of clauses 1 to 23, wherein the IBV is a recombinant IBV.

25. The IBV or the immunogenic composition of any one of clauses 1 to 24, wherein the IBV has a genotype selected from a list of strains containing of: Arkansas (such as Arkansas 99), California (such as California 1734/04, California 99), Connecticut, Delaware (such as Delaware 98), Dutch (such as D207, D212, D274, D3128, D3896, D8880, D1466), Florida, Georgia (such as Georgia GA-08, GA-12, GA-13), Gray, Holte, Iowa (such as Iowa 97 and Iowa 69), Italy (such as Italy 02), JMK, Maine (such as Maine 209), Massachusetts (such as M41, Beaudette, 246 G, D 580, H52, H120), Pennsylvania (such as Pennsylvania 1220/98, Pennsylvania Wolg/98), Qu, (such as Qu-mv), QX (such as GB341/96), Q1, SE 17, Variant 2 (such as IS/1494/06), and 4/91 (793B).

26. The IBV or the immunogenic composition of any one of clauses 1 to 25, wherein the IBV is of QX, Massachusetts, 4/91, Q1, or Italy 02 genotype.

27. The IBV or the immunogenic composition of clause 26, wherein the QX genotype is selected from a list containing of: FR-L1450T-05, FR-L1450L-05, NL-L1449T-04, NL-L1449K-04, IBV/Ck/SP/170/09, IBV/Ck/SP/79/08, IBV/Ck/SP/248/09, HBN, IBVQX, LX4, BJQ, CK/CH/LGD/03, GB341/96.

28. The IBV or the immunogenic composition of clause 26, wherein the Massachusetts genotype is selected from a list containing of: H120, H52, Spain/98/308, IBMA5-1, SD/97/01, Beaudette, Spain/96/334, M41-M21883.

29. The IBV or the immunogenic composition of clause 26, wherein the 4/91 genotype is selected from a list containing of: Spain/98/328, Spain/92/35, IR-3654-VM, FR-CR88061-88, FR-85131-85, UK-1233-95, UK/3/91, Spain/00/336, UK/7/91, 4/91-pathogenic, 4/91 attenuated, IB4-91.

30. The IBV or the immunogenic composition of clause 26, wherein the Q1 genotype is selected from a list containing of: CK/CH/LDL/98I, CK/CH/LSD/08-10, J2, Q1, AR08ER22, AR08BA21, Chile-295-10.

31. The IBV or the immunogenic composition of clause 26, wherein the Italy 02 genotype is selected from a list containing of: Spain/99/316, Italy-02, UK-L633-04, It-497-02, Spain/05/866, Spain/04/221, Spain/00/337, Spain/155/09, Spain/03/08.

32. The IBV or the immunogenic composition of any one of clauses 1 to 26, wherein the IBV is of the Massachusetts genotype strain H52.

33. The immunogenic composition of any one of clauses 2 to 32, wherein the immunogenic composition is a vaccine.

34. The immunogenic composition of any one of clauses 2 to 33, wherein the immunogenic composition comprises a pharmaceutically acceptable carrier.

35. The immunogenic composition of clause 34, wherein the pharmaceutically acceptable carrier is phosphate buffered saline.

36. The immunogenic composition of any one of clauses 2 to 35, wherein the immunogenic composition is effective in the treatment and/or prophylaxis of clinical signs caused by IBV in a subject of need.

37. The immunogenic composition of any one of clauses 2 to 36, wherein the immunogenic composition protects against a homologous challenge.

38. The immunogenic composition of any one of clauses 2 to 37, wherein the immunogenic composition protects against a challenge with M41.

39. The immunogenic composition of any one of clauses 2 to 38, wherein said immunogenic composition is formulated for a single-dose administration.

40. The immunogenic composition of any one of clauses 2 to 39, wherein said immunogenic composition is administered subcutaneously, intramuscularly, oral, in ovo, via spray, via drinking water, or by eye drop.

41. The immunogenic composition of any one of clauses 2 to 40, wherein the immunogenic composition comprises 1 to 10 $\log_{10}$ $EID_{50}$ of the IBV.

42. The immunogenic composition of any one of clauses 2 to 41, wherein the immunogenic composition comprises 2 to 5 $\log_{10}$ $EID_{50}$ of the IBV.

43. The immunogenic composition of any one of clauses 2 to 42, wherein the immunogenic composition comprises 2 to 4 $\log_{10}$ $EID_{50}$ of the IBV.

44. A kit comprising the IBV or the immunogenic composition of any one of clauses 1 to 43.

45. The kit according to clause 44, wherein the kit further comprises an instruction letter for the treatment and/or prophylaxis of diseases of avians.

46. The kit according to clause 45, wherein the kit further comprises an instruction letter for the treatment and/or prophylaxis of diseases of poultry.

47. The kit according to clauses 46, wherein the kit further comprises an instruction letter for the treatment and/or prophylaxis of IB.

48. A method for immunizing a subject comprising administering to such subject an immunogenic composition according to any one of clauses 2 to 43.

49. A method of treating or preventing clinical signs caused by IBV in a subject of need, the method comprising administering to the subject a therapeutically effective amount of an immunogenic composition according to any one of clauses 2 to 43.

50. A method of reducing the ciliostasis in a subject of need, in comparison to a subject of a non-immunized control group of the same species, the method comprising administering to the subject a therapeutically effective amount of an immunogenic composition according to any one of clauses 2 to 43.

51. The immunogenic composition according to any one of clauses 2 to 43 for use in a method for immunizing a subject, the method comprising administering to the subject a therapeutically effective amount of said immunogenic composition.

52. The immunogenic composition according to any one of clauses 2 to 43 for use in a method of treating or preventing clinical signs caused by IBV in a subject of need, the method comprising administering to the subject a therapeutically effective amount of said immunogenic composition.

53. The immunogenic composition according to any one of clauses 2 to 43 for use in a method of reducing the ciliostasis in a subject of need, in comparison to a subject of a non-immunized control group of the same species, the method comprising administering to the subject a therapeutically effective amount of said immunogenic composition.

54. The method or use of any one of clauses 48 to 53, wherein said subject is avian.

55. The method or use of any one of clauses 48 to 54, wherein said subject is poultry.

56. The method or use of any one of clauses 48 to 55, wherein said subject is selected from the list consisting of chicken, turkey, quail, or pheasant.

57. The method or use of any one of clauses 48 to 56, wherein the immunogenic composition is administered once.

58. The method or use of any one of clauses 48 to 56, wherein the immunogenic composition is administered at two or more doses.

59. The method or use of any one of clauses 48 to 58, wherein said immunogenic composition is administered subcutaneously, intramuscularly, oral, in ovo, via spray, via drinking water or by eye drop.

60. The method or use of any one of clauses 48 to 59, wherein said immunogenic composition is administered via eye drop.

61. The method or use of any one of clauses 48 to 60, wherein the immunogenic composition comprises 1 to 10 $\log_{10}$ $EID_{50}$ of the IBV.

62. The method or use of any one of clauses 48 to 61, wherein the immunogenic composition comprises 2 to 5 $\log_{10}$ $EID_{50}$ of the IBV.

63. The method or use of any one of clauses 48 to 62, wherein the immunogenic composition comprises 2 to 4 $\log_{10}$ $EID_{50}$ of the IBV.

64. The method or use of any one of clauses 48 to 63, wherein the immunogenic composition is administered to subjects within the first week of age, within the first three days of age, within the first two days of age, or within the first day of age.

65. The method or use of any one of clauses 48 to 64, wherein the immunogenic composition is administered to subjects within the first day of age.

66. The method or use of any one of clauses 48 to 65, wherein said method results in an improvement in an efficacy parameter selected from the group consisting of: prevention or reduction of ciliostasis, prevention or reduction of rales, prevention or reduction of egg drop, prevention or reduction of kidney lesions, prevention or reduction of watery diarrhea, prevention or reduction in weight loss, a lower virus load, a reduced viral shedding or combinations thereof, in comparison to a subject of a non-treated control group of the same species.

67. The method or use of any one of clauses 48 to 66, wherein the treatment or prevention results in a prevention or reduction of ciliostasis as compared to subjects of a non-treated control group of the same species.

68. The method or use of any one of clauses 48 to 67, wherein the treatment or prevention results in a prevention or reduction of kidney lesions as compared to subjects of a non-treated control group of the same species.

69. The method or use of any one of clauses 48 to 68, wherein the treatment or prevention results in a prevention or reduction of egg drop as compared to subjects of a non-treated control group of the same species.

70. The IBV or immunogenic composition of any one of clauses 1 to 43 for therapeutic use.

71. The IBV or immunogenic composition of any one of clauses 1 to 43 for use as an immunogen or vaccine.

72. The IBV or immunogenic composition any one of clauses 1 to 43 for use as a medicament.

73. Use of the IBV or immunogenic composition of any one of clauses 1 to 43 for the manufacture of a medicament.

74. Use of the IBV or immunogenic composition of any one of clauses 1 to 43 for the treatment and/or prophylaxis of IBV infections in a subject.

The Following Clauses Relating to an ORF 3b Inactivation are Also Described Herein:

1. An IBV (infectious bronchitis virus), wherein the ORF 3b is inactivated.

2. An immunogenic composition comprising an IBV (infectious bronchitis virus), wherein the ORF 3b is inactivated.

3. The IBV or the immunogenic composition of clause 1 or 2, wherein said inactivation of ORF 3b does not affect the expression of ORF 3a and/or not the activity of the 3a protein.

4. The IBV or the immunogenic composition of any one of clauses 1 to 3, wherein said inactivation of ORF 3b does not affect the expression of ORF 3c and/or not the activity of the E protein.

5. The IBV or the immunogenic composition of any one of clauses 1 to 4, wherein said inactivation is a partial deletion of the ORF 3b, a partial truncation of the ORF 3b, a partial inversion of the ORF 3b, a partial relocation of the ORF 3b, an insertion of nucleic acids within the ORF 3b, a substitution of nucleic acids within the ORF 3b.

6. The IBV or the immunogenic composition of any one of clauses 1 to 5, wherein the ORF 3b is partially deleted, substituted, or inverted.

7. The IBV or the immunogenic composition of any one of clauses 1 to 6, wherein the ORF 3b is partially deleted.

8. The IBV or the immunogenic composition of any one of clauses 1 to 7, wherein the start codon of ORF 3b is inactivated.

9. The IBV or the immunogenic composition of any one of clauses 1 to 8, wherein the start codon of ORF 3b (AUG, nucleotides 174-176 of SEQ ID NO:1) is inactivated.

10. The IBV or the immunogenic composition of clause 8 or clause 9, wherein said inactivation of the start codon (AUG) of ORF 3b is a deletion, substitution, or inversion.

11. The IBV or the immunogenic composition of any one of clauses 1 to 10, wherein the ORF 3b is truncated from the 5'-Terminus of the start codon (AUG, nucleotides 174-176 of SEQ ID NO:1) of ORF 3b.

12. The IBV or the immunogenic composition of any one of clauses 1 to 11, wherein the ORF 3b is truncated from the A, U, or G of the start codon (AUG, nucleotides 174-176 of SEQ ID NO:1) of ORF 3b.

13. The IBV or the immunogenic composition of any one of clauses 1 to 12, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides from the 5'-Terminus of the start codon (AUG, nucleotides 174-176 of SEQ ID NO:1) of the ORF 3b are deleted, substituted, or inverted.

14. The IBV or the immunogenic composition of any one of clauses 1 to 13, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides from the A, U, or G of the start codon (AUG, nucleotides 174-176 of SEQ ID NO:1) of the ORF 3b are deleted, substituted, or inverted.

15. The IBV or the immunogenic composition of any one of clauses 1 to 14, wherein between 1 and 175 nucleotides from the 5'-Terminus of the start codon (AUG, nucleotides 174-176 of SEQ ID NO:1) of the ORF 3b are deleted, substituted, or inverted.

16. The IBV or the immunogenic composition of any one of clauses 1 to 15, wherein between 1 and 175 nucleotides from the A of the start codon (A of AUG, nucleotide 174 of SEQ ID NO:1) or between 1 and 174 nucleotides from the U of the start codon (U of AUG, nucleotide 175 of SEQ ID NO:1) or between 1 and 173 nucleotides from the G of the start codon (G of AUG, nucleotide 176 of SEQ ID NO:1) of the ORF 3b are deleted, substituted or inverted.

17. The IBV or the immunogenic composition of any one of clauses 1 to 16, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides of the ORF 3b are deleted, substituted or inverted.

18. The IBV or the immunogenic composition of any one of clauses 1 to 17, wherein between 1 and 175 nucleotides of the ORF 3b are deleted, substituted or inverted.

19. The IBV or the immunogenic composition of any one of clauses 1 to 18, wherein the ORF 3b from the 5'-Terminus of the start codon (AUG, nucleotides 174-176 of SEQ ID NO:1) of the ORF 3b to nucleotide 348 of SEQ ID NO:1 is deleted, substituted or inverted.

20. The IBV or the immunogenic composition of any one of clauses 1 to 19, wherein the RNA sequence as set forth in SEQ ID NO:34 is deleted, substituted or inverted within the ORF 3b.

21. The IBV or the immunogenic composition of any one of clauses 1 to 20, wherein a RNA sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the RNA sequence as set forth in SEQ ID NO:34 is deleted, substituted or inverted within the ORF 3b.

22. The IBV or the immunogenic composition of any one of clauses 1 to 21, wherein the IBV is attenuated.

23. The IBV or the immunogenic composition of any one of clauses 1 to 22, wherein the IBV is genetically engineered.

24. The IBV or the immunogenic composition of any one of clauses 1 to 23, wherein the IBV is a recombinant IBV.

25. The IBV or the immunogenic composition of any one of clauses 1 to 24, wherein the IBV has a genotype selected from a list of strains containing of: Arkansas (such as Arkansas 99), California (such as California 1734/04, California 99), Connecticut, Delaware (such as Delaware 98), Dutch (such as D207, D212, D274, D3128, D3896, D8880, D1466), Florida, Georgia (such as Georgia GA-08, GA-12, GA-13), Gray, Holte, Iowa (such as Iowa 97 and Iowa 69), Italy (such as Italy 02), JMK, Maine (such as Maine 209), Massachusetts (such as M41, Beaudette, 246 G, D 580, H52, H120), Pennsylvania (such as Pennsylvania 1220/98, Pennsylvania Wolg/98), Qu, (such as Qu-mv), QX (such as GB341/96), Q1, SE 17, Variant 2 (such as IS/1494/06) and 4/91 (793B).

26. The IBV or the immunogenic composition of any one of clauses 1 to 25, wherein the IBV is of QX, Massachusetts, 4/91, Q1 or Italy 02 genotype.

27. The IBV or the immunogenic composition of clause 26, wherein the QX genotype is selected from a list containing of: FR-L1450T-05, FR-L1450L-05, NL-L1449T-04, NL-L1449K-04, IBV/Ck/SP/170/09, IBV/Ck/SP/79/08, IBV/Ck/SP/248/09, HBN, IBVQX, LX4, BJQ, CK/CH/LGD/03, GB341/96.

28. The IBV or the immunogenic composition of clause 26, wherein the Massachusetts genotype is selected from a list containing of: H120, H52, Spain/98/308, IBMA5-1, SD/97/01, Beaudette, Spain/96/334, M41-M21883.

29. The IBV or the immunogenic composition of clause 26, wherein the 4/91 genotype is selected from a list containing of: Spain/98/328, Spain/92/35, IR-3654-VM, FR-CR88061-88, FR-85131-85, UK-1233-95, UK/3/91, Spain/00/336, UK/7/91, 4/91-pathogenic, 4/91 attenuated, IB4-91.

30. The IBV or the immunogenic composition of clause 26, wherein the Q1 genotype is selected from a list containing of: CK/CH/LDL/98I, CK/CH/LSD/08-10, J2, Q1, AR08ER22, AR08BA21, Chile-295-10.

31. The IBV or the immunogenic composition of clause 26, wherein the Italy 02 genotype is selected from a list containing of: Spain/99/316, Italy-02, UK-L633-04, It-497-02, Spain/05/866, Spain/04/221, Spain/00/337, Spain/155/09, Spain/03/08.

32. The IBV or the immunogenic composition of any one of clauses 1 to 26, wherein the IBV is of the Massachusetts genotype strain H52.

33. The immunogenic composition of any one of clauses 2 to 32, wherein the immunogenic composition is a vaccine.

34. The immunogenic composition of any one of clauses 2 to 33, wherein the immunogenic composition comprises a pharmaceutically acceptable carrier.

35. The immunogenic composition of clause 34, wherein the pharmaceutically acceptable carrier is phosphate buffered saline.

36. The immunogenic composition of any one of clauses 2 to 35, wherein the immunogenic composition is effective in the treatment and/or prophylaxis of clinical signs caused by IBV in a subject of need.

37. The immunogenic composition of any one of clauses 2 to 36, wherein the immunogenic composition protects against a homologous challenge.

38. The immunogenic composition of any one of clauses 2 to 37, wherein the immunogenic composition protects against a challenge with M41.

39. The immunogenic composition of any one of clauses 2 to 38, wherein said immunogenic composition is formulated for a single-dose administration.

40. The immunogenic composition of any one of clauses 2 to 39, wherein said immunogenic composition is administered subcutaneously, intramuscularly, oral, in ovo, via spray, via drinking water or by eye drop.

41. The immunogenic composition of any one of clauses 2 to 40, wherein the immunogenic composition comprises 1 to 10 $\log_{10}$ $EID_{50}$ of the IBV.

42. The immunogenic composition of any one of clauses 2 to 41, wherein the immunogenic composition comprises 2 to 5 $\log_{10}$ $EID_{50}$ of the IBV.

43. The immunogenic composition of any one of clauses 2 to 42, wherein the immunogenic composition comprises 2 to 4 $\log_{10}$ $EID_{50}$ of the IBV.

44. A kit comprising the IBV or the immunogenic composition of any one of clauses 1 to 43.

45. The kit according to clause 44, wherein the kit further comprises an instruction letter for the treatment and/or prophylaxis of diseases of avians.

46. The kit according to clause 45, wherein the kit further comprises an instruction letter for the treatment and/or prophylaxis of diseases of poultry.

47. The kit according to clauses 46, wherein the kit further comprises an instruction letter for the treatment and/or prophylaxis of IB.

48. A method for immunizing a subject comprising administering to such subject an immunogenic composition according to any one of clauses 2 to 43.

49. A method of treating or preventing clinical signs caused by IBV in a subject of need, the method comprising administering to the subject a therapeutically effective amount of an immunogenic composition according to any one of clauses 2 to 43.

50. A method of reducing the ciliostasis in a subject of need, in comparison to a subject of a non-immunized control group of the same species, the method comprising administering to the subject a therapeutically effective amount of an immunogenic composition according to any one of clauses 2 to 43.

51. The immunogenic composition according to any one of clauses 2 to 43 for use in a method for immunizing a subject, the method comprising administering to the subject a therapeutically effective amount of said immunogenic composition.

52. The immunogenic composition according to any one of clauses 2 to 43 for use in a method of treating or preventing clinical signs caused by IBV in a subject of need, the method comprising administering to the subject a therapeutically effective amount of said immunogenic composition.

53. The immunogenic composition according to any one of clauses 2 to 43 for use in a method of reducing the ciliostasis in a subject of need, in comparison to a subject of a non-immunized control group of the same species, the method comprising administering to the subject a therapeutically effective amount of said immunogenic composition.

54. The method or use of any one of clauses 48 to 53, wherein said subject is avian.

55. The method or use of any one of clauses 48 to 54, wherein said subject is poultry.

56. The method or use of any one of clauses 48 to 55, wherein said subject is selected from the list consisting of chicken, turkey, quail, or pheasant.

57. The method or use of any one of clauses 48 to 56, wherein the immunogenic composition is administered once.

58. The method or use of any one of clauses 48 to 56, wherein the immunogenic composition is administered at two or more doses.

59. The method or use of any one of clauses 48 to 58, wherein said immunogenic composition is administered subcutaneously, intramuscularly, oral, in ovo, via spray, via drinking water, or by eye drop.

60. The method or use of any one of clauses 48 to 59, wherein said immunogenic composition is administered via eye drop.

61. The method or use of any one of clauses 48 to 60, wherein the immunogenic composition comprises 1 to 10 $\log_{10}$ $EID_{50}$ of the IBV.

62. The method or use of any one of clauses 48 to 61, wherein the immunogenic composition comprises 2 to 5 $\log_{10}$ $EID_{50}$ of the IBV.

63. The method or use of any one of clauses 48 to 62, wherein the immunogenic composition comprises 2 to 4 $\log_{10}$ $EID_{50}$ of the IBV.

64. The method or use of any one of clauses 48 to 63, wherein the immunogenic composition is administered to subjects within the first week of age, within the first three days of age, within the first two days of age, or within the first day of age.

65. The method or use of any one of clauses 48 to 64, wherein the immunogenic composition is administered to subjects within the first day of age.

66. The method or use of any one of clauses 48 to 65, wherein said method results in an improvement in an efficacy parameter selected from the group consisting of: prevention or reduction of ciliostasis, prevention or reduction of rales, prevention or reduction of egg drop, prevention or reduction of kidney lesions, prevention or reduction of watery diarrhea, prevention or reduction in weight loss, a lower virus load, a reduced viral shedding or combinations thereof, in comparison to a subject of a non-treated control group of the same species.

67. The method or use of any one of clauses 48 to 66, wherein the treatment or prevention results in a prevention or reduction of ciliostasis as compared to subjects of a non-treated control group of the same species.

68. The method or use of any one of clauses 48 to 67, wherein the treatment or prevention results in a prevention or reduction of kidney lesions as compared to subjects of a non-treated control group of the same species.

69. The method or use of any one of clauses 48 to 68, wherein the treatment or prevention results in a prevention or reduction of egg drop as compared to subjects of a non-treated control group of the same species.

70. The IBV or immunogenic composition of any one of clauses 1 to 43 for therapeutic use.

71. The IBV or immunogenic composition of any one of clauses 1 to 43 for use as an immunogen or vaccine.

72. The IBV or immunogenic composition any one of clauses 1 to 43 for use as a medicament.

73. Use of the IBV or immunogenic composition of any one of clauses 1 to 43 for the manufacture of a medicament.

74. Use of the IBV or immunogenic composition of any one of clauses 1 to 43 for the treatment and/or prophylaxis of IBV infections in a subject.

The Following Clauses Relating to an ORF 5a Inactivation are Also Described Herein:

1. An IBV (infectious bronchitis virus), wherein the ORF 5a is inactivated.

2. An immunogenic composition comprising an IBV (infectious bronchitis virus), wherein the ORF 5a is inactivated.

3. The IBV or the immunogenic composition of clause 1 or 2, wherein said inactivation of ORF 5a does not affect the expression of ORF 5b and/or not the activity of the 5b protein.

4. The IBV or the immunogenic composition of any one of clauses 1 to 3, wherein said inactivation is a complete or partial deletion of the ORF 5a, a complete or partial truncation of the ORF 5a, a complete or partial inversion of the ORF 5a, a complete or partial relocation of the ORF 5a, an insertion of nucleic acids within the ORF 5a, a substitution of nucleic acids within the ORF 5a.

5. The IBV or the immunogenic composition of any one of clauses 1 to 4, wherein the ORF 5a is partially deleted, substituted, or inverted.

6. The IBV or the immunogenic composition of any one of clauses 1 to 5, wherein the ORF 5a is partially deleted.

7. The IBV or the immunogenic composition of any one of clauses 1 to 6, wherein the start codon of ORF 5a is inactivated.

8. The IBV or the immunogenic composition of any one of clauses 1 to 7, wherein the start codon of ORF 5a (AUG, nucleotides 1-3 of SEQ ID NO:2) is inactivated.

9. The IBV or the immunogenic composition of clause 7 or clause 8, wherein said inactivation of the start codon (AUG) of ORF 5a is a deletion, substitution, or inversion.

10. The IBV or the immunogenic composition of any one of clauses 7 to 9 clause 8, wherein said inactivation of the start codon (AUG) of ORF 5a is a deletion.

11. The IBV or the immunogenic composition of any one of clauses 1 to 10, wherein the ORF 5a is truncated from the 5'-Terminus of the start codon of ORF 5a (AUG, nucleotides 1-3 of SEQ ID NO:2).

12. The IBV or the immunogenic composition of any one of clauses 1 to 11, wherein the ORF 5a is truncated from the A, U, or G of the start codon of ORF 5a (AUG, nucleotides 1-3 of SEQ ID NO:2).

13. The IBV or the immunogenic composition of any one of clauses 1 to 12, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides from the 5'-Terminus of the start codon (AUG, nucleotides 1-3 of SEQ ID NO:2) of the ORF 5a are deleted, substituted or inverted.

14. The IBV or the immunogenic composition of any one of clauses 1 to 13, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides from the A, U, or G of the start codon (AUG, nucleotides 1-3 of SEQ ID NO:2) of the ORF 5a are deleted, substituted or inverted.

15. The IBV or the immunogenic composition of any one of clauses 1 to 14, wherein between 1 and 194 nucleotides from the 5'-Terminus of the start codon (AUG, nucleotides 1-3 of SEQ ID NO:2) of the ORF 5a are deleted, substituted, or inverted.

16. The IBV or the immunogenic composition of any one of clauses 1 to 15, wherein between 1 and 194 nucleotides from the A of the start codon (A of AUG, nucleotide 1 of SEQ ID NO:2) or between 1 and 193 nucleotides from the U of the start codon (U of AUG, nucleotide 2 of SEQ ID NO:2) or between 1 and 192 nucleotides from the G of the start codon (G of AUG, nucleotide 3 of SEQ ID NO:2) of the ORF 5a are deleted, substituted or inverted.

17. The IBV or the immunogenic composition of any one of clauses 1 to 16, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides of the ORF 5a are deleted, substituted or inverted.

18. The IBV or the immunogenic composition of any one of clauses 1 to 17, wherein between 1 and 194 nucleotides of the ORF 5a are deleted, substituted, or inverted.

19. The IBV or the immunogenic composition of any one of clauses 1 to 18, wherein the ORF 5a from the 5'-Terminus of the start codon (AUG, nucleotides 1-3 of SEQ ID NO:2) of the ORF 5a to nucleotide 194 of SEQ ID NO:2 is deleted, substituted or inverted.

20. The IBV or the immunogenic composition of any one of clauses 1 to 19, wherein the RNA sequence as set forth in SEQ ID NO:35 is deleted, substituted or inverted within the ORF 5a.

21. The IBV or the immunogenic composition of any one of clauses 1 to 20, wherein a RNA sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the RNA sequence as set forth in SEQ ID NO:35 is deleted, substituted or inverted within the ORF 5a.

22. The IBV or the immunogenic composition of any one of clauses 1 to 21, wherein the IBV is attenuated.

23. The IBV or the immunogenic composition of any one of clauses 1 to 22, wherein the IBV is genetically engineered.

24. The IBV or the immunogenic composition of any one of clauses 1 to 23, wherein the IBV is a recombinant IBV.

25. The IBV or the immunogenic composition of any one of clauses 1 to 24, wherein the IBV has a genotype selected from a list of strains containing of: Arkansas (such as Arkansas 99), California (such as California 1734/04, California 99), Connecticut, Delaware (such as Delaware 98), Dutch (such as D207, D212, D274, D3128, D3896, D8880, D1466), Florida, Georgia (such as Georgia GA-08, GA-12, GA-13), Gray, Holte, Iowa (such as Iowa 97 and Iowa 69), Italy (such as Italy 02), JMK, Maine (such as Maine 209), Massachusetts (such as M41, Beaudette, 246 G, D 580, H52, H120), Pennsylvania (such as Pennsylvania 1220/98, Pennsylvania Wolg/98), Qu, (such as Qu-mv), QX (such as GB341/96), Q1, SE 17, Variant 2 (such as IS/1494/06), and 4/91 (793B).

26. The IBV or the immunogenic composition of any one of clauses 1 to 25, wherein the IBV is of QX, Massachusetts, 4/91, Q1, or Italy 02 genotype.

27. The IBV or the immunogenic composition of clause 26, wherein the QX genotype is selected from a list containing of: FR-L1450T-05, FR-L1450L-05, NL-L1449T-04, NL-L1449K-04, IBV/Ck/SP/170/09, IBV/Ck/SP/79/08, IBV/Ck/SP/248/09, HBN, IBVQX, LX4, BJQ, CK/CH/LGD/03, GB341/96.

28. The IBV or the immunogenic composition of clause 26, wherein the Massachusetts genotype is selected from a list containing of: H120, H52, Spain/98/308, IBMA5-1, SD/97/01, Beaudette, Spain/96/334, M41-M21883.

29. The IBV or the immunogenic composition of clause 26, wherein the 4/91 genotype is selected from a list containing of: Spain/98/328, Spain/92/35, IR-3654-VM, FR-CR88061-88, FR-85131-85, UK-1233-95, UK/3/91, Spain/00/336, UK/7/91, 4/91-pathogenic, 4/91 attenuated, IB4-91.

30. The IBV or the immunogenic composition of clause 26, wherein the Q1 genotype is selected from a list containing of: CK/CH/LDL/98I, CK/CH/LSD/08-10, J2, Q1, AR08ER22, AR08BA21, Chile-295-10.

31. The IBV or the immunogenic composition of clause 26, wherein the Italy 02 genotype is selected from a list containing of: Spain/99/316, Italy-02, UK-L633-04, It-497-02, Spain/05/866, Spain/04/221, Spain/00/337, Spain/155/09, Spain/03/08.

32. The IBV or the immunogenic composition of any one of clauses 1 to 26, wherein the IBV is of the Massachusetts genotype strain H52.

33. The immunogenic composition of any one of clauses 2 to 32, wherein the immunogenic composition is a vaccine.

34. The immunogenic composition of any one of clauses 2 to 33, wherein the immunogenic composition comprises a pharmaceutically acceptable carrier.

35. The immunogenic composition of clause 34, wherein the pharmaceutically acceptable carrier is phosphate buffered saline.

36. The immunogenic composition of any one of clauses 2 to 35, wherein the immunogenic composition is effective in the treatment and/or prophylaxis of clinical signs caused by IBV in a subject of need.

37. The immunogenic composition of any one of clauses 2 to 36, wherein the immunogenic composition protects against a homologous challenge.

38. The immunogenic composition of any one of clauses 2 to 37, wherein the immunogenic composition protects against a challenge with M41.

39. The immunogenic composition of any one of clauses 2 to 38, wherein said immunogenic composition is formulated for a single-dose administration.

40. The immunogenic composition of any one of clauses 2 to 39, wherein said immunogenic composition is administered subcutaneously, intramuscularly, oral, in ovo, via spray, via drinking water, or by eye drop.

41. The immunogenic composition of any one of clauses 2 to 40, wherein the immunogenic composition comprises 1 to 10 $\log_{10}$ $EID_{50}$ of the IBV.

42. The immunogenic composition of any one of clauses 2 to 41, wherein the immunogenic composition comprises 2 to 5 $\log_{10}$ $EID_{50}$ of the IBV.

43. The immunogenic composition of any one of clauses 2 to 42, wherein the immunogenic composition comprises 2 to 4 $\log_{10}$ $EID_{50}$ of the IBV.

44. A kit comprising the IBV or the immunogenic composition of any one of clauses 1 to 43.

45. The kit according to clause 44, wherein the kit further comprises an instruction letter for the treatment and/or prophylaxis of diseases of avians.

46. The kit according to clause 45, wherein the kit further comprises an instruction letter for the treatment and/or prophylaxis of diseases of poultry.

47. The kit according to clauses 46, wherein the kit further comprises an instruction letter for the treatment and/or prophylaxis of IB.

48. A method for immunizing a subject comprising administering to such subject an immunogenic composition according to any one of clauses 2 to 43.

49. A method of treating or preventing clinical signs caused by IBV in a subject of need, the method comprising administering to the subject a therapeutically effective amount of an immunogenic composition according to any one of clauses 2 to 43.

50. A method of reducing the ciliostasis in a subject of need, in comparison to a subject of a non-immunized control group of the same species, the method comprising administering to the subject a therapeutically effective amount of an immunogenic composition according to any one of clauses 2 to 43.

51. The immunogenic composition according to any one of clauses 2 to 43 for use in a method for immunizing a subject, the method comprising administering to the subject a therapeutically effective amount of said immunogenic composition.

52. The immunogenic composition according to any one of clauses 2 to 43 for use in a method of treating or preventing clinical signs caused by IBV in a subject of need, the method comprising administering to the subject a therapeutically effective amount of said immunogenic composition.

53. The immunogenic composition according to any one of clauses 2 to 43 for use in a method of reducing the ciliostasis in a subject of need, in comparison to a subject of a non-immunized control group of the same species, the method comprising administering to the subject a therapeutically effective amount of said immunogenic composition.

54. The method or use of any one of clauses 48 to 53, wherein said subject is avian.

55. The method or use of any one of clauses 48 to 54, wherein said subject is poultry.

56. The method or use of any one of clauses 48 to 55, wherein said subject is selected from the list consisting of chicken, turkey, quail, or pheasant.

57. The method or use of any one of clauses 48 to 56, wherein the immunogenic composition is administered once.

58. The method or use of any one of clauses 48 to 56, wherein the immunogenic composition is administered at two or more doses.

59. The method or use of any one of clauses 48 to 58, wherein said immunogenic composition is administered subcutaneously, intramuscularly, oral, in ovo, via spray, via drinking water, or by eye drop.

60. The method or use of any one of clauses 48 to 59, wherein said immunogenic composition is administered via eye drop.

61. The method or use of any one of clauses 48 to 60, wherein the immunogenic composition comprises 1 to 10 $\log_{10}$ $EID_{50}$ of the IBV.

62. The method or use of any one of clauses 48 to 61, wherein the immunogenic composition comprises 2 to 5 $\log_{10}$ $EID_{50}$ of the IBV.

63. The method or use of any one of clauses 48 to 62, wherein the immunogenic composition comprises 2 to 4 $\log_{10}$ $EID_{50}$ of the IBV.

64. The method or use of any one of clauses 48 to 63, wherein the immunogenic composition is administered to subjects within the first week of age, within the first three days of age, within the first two days of age, or within the first day of age.

65. The method or use of any one of clauses 48 to 64, wherein the immunogenic composition is administered to subjects within the first day of age.

66. The method or use of any one of clauses 48 to 65, wherein said method results in an improvement in an efficacy parameter selected from the group consisting of: prevention or reduction of ciliostasis, prevention or reduction of rales, prevention or reduction of egg drop, prevention or reduction of kidney lesions, prevention or reduction of watery diarrhea, prevention or reduction in weight loss, a lower virus load, a reduced viral shedding or combinations thereof, in comparison to a subject of a non-treated control group of the same species.

67. The method or use of any one of clauses 48 to 66, wherein the treatment or prevention results in a prevention or reduction of ciliostasis as compared to subjects of a non-treated control group of the same species.

68. The method or use of any one of clauses 48 to 67, wherein the treatment or prevention results in a prevention or reduction of kidney lesions as compared to subjects of a non-treated control group of the same species.

69. The method or use of any one of clauses 48 to 68, wherein the treatment or prevention results in a prevention or reduction of egg drop as compared to subjects of a non-treated control group of the same species.

70. The IBV or immunogenic composition of any one of clauses 1 to 43 for therapeutic use.

71. The IBV or immunogenic composition of any one of clauses 1 to 43 for use as an immunogen or vaccine.

72. The IBV or immunogenic composition any one of clauses 1 to 43 for use as a medicament.

73. Use of the IBV or immunogenic composition of any one of clauses 1 to 43 for the manufacture of a medicament.

74. Use of the IBV or immunogenic composition of any one of clauses 1 to 43 for the treatment and/or prophylaxis of IBV infections in a subject.

The Following Clauses Relating to an ORF 5b Inactivation are Also Described Herein:

1. An IBV (infectious bronchitis virus), wherein the ORF 5b is inactivated.

2. An immunogenic composition comprising an IBV (infectious bronchitis virus), wherein the ORF 5b is inactivated.

3. The IBV or the immunogenic composition of clause 1 or 2, wherein said inactivation of ORF 5b does not affect the expression of ORF N and/or not the activity of the N protein.

4. The IBV or the immunogenic composition of any one of clauses 1 to 3, wherein said inactivation of ORF 5b does not affect the expression of ORF 5a and/or not the activity of 5a protein.

5. The IBV or the immunogenic composition of any one of clauses 1 to 4, wherein said inactivation is a partial deletion of the ORF 5b, a partial truncation of the ORF 5b, a partial inversion of the ORF 5b, a partial relocation of the ORF 5b, an insertion of nucleic acids within the ORF 5b, a substitution of nucleic acids within the ORF 5b.

6. The IBV or the immunogenic composition of any one of clauses 1 to 5, wherein the ORF 5b is partially deleted, substituted, or inverted.

7. The IBV or the immunogenic composition of any one of clauses 1 to 6, wherein the ORF 5b is partially deleted.

8. The IBV or the immunogenic composition of any one of clauses 1 to 7, wherein the start codon of ORF 5b is inactivated.

9. The IBV or the immunogenic composition of any one of clauses 1 to 8, wherein the start codon of ORF 5b (AUG, nucleotides 195-197 of SEQ ID NO:2) is inactivated.

10. The IBV or the immunogenic composition of clause 8 or clause 9, wherein said inactivation of the start codon (AUG) of ORF 5b is a deletion, substitution or inversion.

11. The IBV or the immunogenic composition of any one of clauses 1 to 10, wherein the ORF 5b is truncated from the 5'-Terminus of the start codon of ORF 5b (AUG, nucleotides 195-197 of SEQ ID NO:2).

12. The IBV or the immunogenic composition of any one of clauses 1 to 11, wherein the ORF 5b is truncated from the A, U, or G of the start codon of ORF 5b (AUG, nucleotides 195-197 of SEQ ID NO:2).

13. The IBV or the immunogenic composition of any one of clauses 1 to 12, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 90 nucleotides, at least 100 nucleotides, at least 125 nucleotides, at least 150 nucleotides, at least 170 nucleotides, at least 190 nucleotides from the 5'-Terminus of the start codon (AUG, nucleotides 195-197 of SEQ ID NO:2) of the ORF 5b are deleted, substituted or inverted.

14. The IBV or the immunogenic composition of any one of clauses 1 to 13, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 90 nucleotides, at least 100 nucleotides, at least 125 nucleotides, at least 150 nucleotides, at least 170 nucleotides, at least 190 nucleotides from the A, U or G of the start codon (AUG, nucleotides 195-197 of SEQ ID NO:2) of the ORF 5b are deleted, substituted, or inverted.

15. The IBV or the immunogenic composition of any one of clauses 1 to 14, wherein between 1 and 90 nucleotides from the 5'-Terminus of the start codon (AUG, nucleotides 195-197 of SEQ ID NO:2) of the ORF 5b are deleted, substituted, or inverted.

16. The IBV or the immunogenic composition of any one of clauses 1 to 15, wherein between 1 and 191 nucleotides from the 5'-Terminus of the start codon (AUG, nucleotides 195-197 of SEQ ID NO:2) of the ORF 5b are deleted, substituted, or inverted.

17. The IBV or the immunogenic composition of any one of clauses 1 to 16, wherein between 1 and 90 nucleotides from the A of the start codon (A of AUG, nucleotide 195 of SEQ ID NO:2) or between 1 and 89 nucleotides from the U of the start codon (U of AUG, nucleotide 196 of SEQ ID NO:2) or between 1 and 88 nucleotides from the G of the start codon (G of AUG, nucleotide 197 of SEQ ID NO:2) of the ORF 5b are deleted, substituted, or inverted.

18. The IBV or the immunogenic composition of any one of clauses 1 to 17, wherein between 1 and 191 nucleotides from the A of the start codon (A of AUG, nucleotide 195 of SEQ ID NO:2) or between 1 and 190 nucleotides from the U of the start codon (U of AUG, nucleotide 196 of SEQ ID NO:2) or between 1 and 189 nucleotides from the G of the start codon (G of AUG, nucleotide 197 of SEQ ID NO:2) of the ORF 5b are deleted, substituted, or inverted.

19. The IBV or the immunogenic composition of any one of clauses 1 to 18, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 90 nucleotides, at least 100 nucleotides, at least 125 nucleotides, at least 150 nucleotides, at least 170 nucleotides, at least 190 nucleotides of the ORF 5b are deleted, substituted, or inverted.

20. The IBV or the immunogenic composition of any one of clauses 1 to 19, wherein between 1 and 90 nucleotides of the ORF 5b are deleted, substituted or inverted.

21. The IBV or the immunogenic composition of any one of clauses 1 to 20, wherein between 1 and 191 nucleotides of the ORF 5b are deleted, substituted or inverted.

22. The IBV or the immunogenic composition of any one of clauses 1 to 21, wherein the ORF 5b from the 5'-Terminus of the start codon (AUG, nucleotides 195-197 of SEQ ID NO:2) of the ORF 5b to nucleotide 284 of SEQ ID NO:2 is deleted, substituted, or inverted.

23. The IBV or the immunogenic composition of any one of clauses 1 to 22, wherein the RNA sequence as set forth in SEQ ID NO:36 is deleted, substituted or inverted within the ORF 5b.

24. The IBV or the immunogenic composition of any one of clauses 1 to 23, wherein a RNA sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the RNA sequence as set forth in SEQ ID NO:36 is deleted, substituted or inverted within the ORF 5b.

25. The IBV or the immunogenic composition of any one of clauses 1 to 24, wherein a TRS (transcription regulating sequence) is inserted 5' of the ORF N.

26. The IBV or the immunogenic composition of clause 25, wherein said TRS has the sequence CUUAACAA.

27. The IBV or the immunogenic composition of clauses 25 or 26, wherein said TRS (transcription regulating sequence) is inserted for not affecting the expression of ORF N and/or not the activity of the N protein.

28. The IBV or the immunogenic composition of any one of clauses 1 to 27, wherein a sequence comprising stop codons is inserted 5' of the TRS of the ORF N.

29. The IBV or the immunogenic composition of clause 28, wherein said sequence comprising stop codons has a sequence as set forth in SEQ ID NO:37.

30. The IBV or the immunogenic composition of any one of clauses 1 to 29, wherein the IBV is attenuated.

31. The IBV or the immunogenic composition of any one of clauses 1 to 30, wherein the IBV is genetically engineered.

32. The IBV or the immunogenic composition of any one of clauses 1 to 31, wherein the IBV is a recombinant IBV.

33. The IBV or the immunogenic composition of any one of clauses 1 to 32, wherein the IBV has a genotype selected from a list of strains containing of: Arkansas (such as Arkansas 99), California (such as California 1734/04, California 99), Connecticut, Delaware (such as Delaware 98), Dutch (such as D207, D212, D274, D3128, D3896, D8880, D1466), Florida, Georgia (such as Georgia GA-08, GA-12, GA-13), Gray, Holte, Iowa (such as Iowa 97 and Iowa 69), Italy (such as Italy 02), JMK, Maine (such as Maine 209), Massachusetts (such as M41, Beaudette, 246 G, D 580, H52, H120), Pennsylvania (such as Pennsylvania 1220/98, Pennsylvania Wolg/98), Qu, (such as Qu-mv), QX (such as GB341/96), Q1, SE 17, Variant 2 (such as IS/1494/06), and 4/91 (793B).

34. The IBV or the immunogenic composition of any one of clauses 1 to 33, wherein the IBV is of QX, Massachusetts, 4/91, Q1, or Italy 02 genotype.

35. The IBV or the immunogenic composition of clause 34, wherein the QX genotype is selected from a list containing of: FR-L1450T-05, FR-L1450L-05, NL-L1449T-04, NL-L1449K-04, IBV/Ck/SP/170/09, IBV/Ck/SP/79/08, IBV/Ck/SP/248/09, HBN, IBVQX, LX4, BJQ, CK/CH/LGD/03, GB341/96.

36. The IBV or the immunogenic composition of clause 34, wherein the Massachusetts genotype is selected from a list containing of: H120, H52, Spain/98/308, IBMA5-1, SD/97/01, Beaudette, Spain/96/334, M41-M21883.

37. The IBV or the immunogenic composition of clause 34, wherein the 4/91 genotype is selected from a list containing of: Spain/98/328, Spain/92/35, IR-3654-VM, FR-CR88061-88, FR-85131-85, UK-1233-95, UK/3/91, Spain/00/336, UK/7/91, 4/91-pathogenic, 4/91 attenuated, IB4-91.

38. The IBV or the immunogenic composition of clause 34, wherein the Q1 genotype is selected from a list containing of: CK/CH/LDL/98I, CK/CH/LSD/08-10, J2, Q1, AR08ER22, AR08BA21, Chile-295-10.

39. The IBV or the immunogenic composition of clause 34 wherein the Italy 02 genotype is selected from a list containing of: Spain/99/316, Italy-02, UK-L633-04, It-497-02, Spain/05/866, Spain/04/221, Spain/00/337, Spain/155/09, Spain/03/08.

40. The IBV or the immunogenic composition of any one of clauses 1 to 39, wherein the IBV is of the Massachusetts genotype strain H52.

41. The immunogenic composition of any one of clauses 2 to 40, wherein the immunogenic composition is a vaccine.

42. The immunogenic composition of any one of clauses 2 to 41, wherein the immunogenic composition comprises a pharmaceutically acceptable carrier.

43. The immunogenic composition of clause 42, wherein the pharmaceutically acceptable carrier is phosphate buffered saline.

44. The immunogenic composition of any one of clauses 2 to 43, wherein the immunogenic composition is effective in the treatment and/or prophylaxis of clinical signs caused by IBV in a subject of need.

45. The immunogenic composition of any one of clauses 2 to 44, wherein the immunogenic composition protects against a homologous challenge.

46. The immunogenic composition of any one of clauses 2 to 45, wherein the immunogenic composition protects against a challenge with M41.

47. The immunogenic composition of any one of clauses 2 to 46, wherein said immunogenic composition is formulated for a single-dose administration.

48. The immunogenic composition of any one of clauses 2 to 47, wherein said immunogenic composition is administered subcutaneously, intramuscularly, oral, in ovo, via spray, via drinking water, or by eye drop.

49. The immunogenic composition of any one of clauses 2 to 48, wherein the immunogenic composition comprises 1 to 10 $\log_{10}$ $EID_{50}$ of the IBV.

50. The immunogenic composition of any one of clauses 2 to 49, wherein the immunogenic composition comprises 2 to 5 $\log_{10}$ $EID_{50}$ of the IBV.

51. The immunogenic composition of any one of clauses 2 to 50, wherein the immunogenic composition comprises 2 to 4 $\log_{10}$ $EID_{50}$ of the IBV.

52. A kit comprising the IBV or the immunogenic composition of any one of clauses 1 to 51.

53. The kit according to clause 52, wherein the kit further comprises an instruction letter for the treatment and/or prophylaxis of diseases of avians.

54. The kit according to clause 53, wherein the kit further comprises an instruction letter for the treatment and/or prophylaxis of diseases of poultry.

55. The kit according to clauses 54, wherein the kit further comprises an instruction letter for the treatment and/or prophylaxis of IB.

56. A method for immunizing a subject comprising administering to such subject an immunogenic composition according to any one of clauses 2 to 51.

57. A method of treating or preventing clinical signs caused by IBV in a subject of need, the method comprising administering to the subject a therapeutically effective amount of an immunogenic composition according to any one of clauses 2 to 51.

58. A method of reducing the ciliostasis in a subject of need, in comparison to a subject of a non-immunized control group of the same species, the method comprising administering to the subject a therapeutically effective amount of an immunogenic composition according to any one of clauses 2 to 51.

59. The immunogenic composition according to any one of clauses 2 to 51 for use in a method for immunizing a subject, the method comprising administering to the subject a therapeutically effective amount of said immunogenic composition.

60. The immunogenic composition according to any one of clauses 2 to 51 for use in a method of treating or preventing clinical signs caused by IBV in a subject of need, the method comprising administering to the subject a therapeutically effective amount of said immunogenic composition.

61. The immunogenic composition according to any one of clauses 2 to 51 for use in a method of reducing the ciliostasis in a subject of need, in comparison to a subject of a non-immunized control group of the same species, the method comprising administering to the subject a therapeutically effective amount of said immunogenic composition.

62. The method or use of any one of clauses 56 to 61, wherein said subject is avian.

63. The method or use of any one of clauses 56 to 62, wherein said subject is poultry.

64. The method or use of any one of clauses 56 to 63, wherein said subject is selected from the list consisting of chicken, turkey, quail, or pheasant.

65. The method or use of any one of clauses 56 to 64, wherein the immunogenic composition is administered once.

66. The method or use of any one of clauses 56 to 65, wherein the immunogenic composition is administered at two or more doses.

67. The method or use of any one of clauses 56 to 66, wherein said immunogenic composition is administered subcutaneously, intramuscularly, oral, in ovo, via spray, via drinking water, or by eye drop.

68. The method or use of any one of clauses 56 to 67, wherein said immunogenic composition is administered via eye drop.

69. The method or use of any one of clauses 56 to 68, wherein the immunogenic composition comprises 1 to 10 $\log_{10}$ $EID_{50}$ of the IBV.

70. The method or use of any one of clauses 56 to 69, wherein the immunogenic composition comprises 2 to 5 $\log_{10}$ $EID_{50}$ of the IBV.

71. The method or use of any one of clauses 56 to 70, wherein the immunogenic composition comprises 2 to 4 $\log_{10}$ $EID_{50}$ of the IBV.

72. The method or use of any one of clauses 56 to 71, wherein the immunogenic composition is administered to subjects within the first week of age, within the first three days of age, within the first two days of age, or within the first day of age.

73. The method or use of any one of clauses 56 to 72, wherein the immunogenic composition is administered to subjects within the first day of age.

74. The method or use of any one of clauses 56 to 73, wherein said method results in an improvement in an efficacy parameter selected from the group consisting of: prevention or reduction of ciliostasis, prevention or reduction of rales, prevention or reduction of egg drop, prevention or reduction of kidney lesions, prevention or reduction of watery diarrhea, prevention or reduction in weight loss, a lower virus load, a reduced viral shedding or combinations thereof, in comparison to a subject of a non-treated control group of the same species.

75. The method or use of any one of clauses 56 to 74, wherein the treatment or prevention results in a prevention or reduction of ciliostasis as compared to subjects of a non-treated control group of the same species.

76. The method or use of any one of clauses 56 to 75, wherein the treatment or prevention results in a prevention or reduction of kidney lesions as compared to subjects of a non-treated control group of the same species.

77. The method or use of any one of clauses 56 to 76, wherein the treatment or prevention results in a prevention or reduction of egg drop as compared to subjects of a non-treated control group of the same species.

78. The IBV or immunogenic composition of any one of clauses 1 to 51 for therapeutic use.

79. The IBV or immunogenic composition of any one of clauses 1 to 51 for use as an immunogen or vaccine.

80. The IBV or immunogenic composition any one of clauses 1 to 51 for use as a medicament.

81. Use of the IBV or immunogenic composition of any one of clauses 1 to 51 for the manufacture of a medicament.

82. Use of the IBV or immunogenic composition of any one of clauses 1 to 51 for the treatment and/or prophylaxis of IBV infections in a subject.

The Following Clauses are Also Described Herein:

1. An IBV (infectious bronchitis virus), wherein:
   the ORF 3a; and/or
   the ORF 3b; and/or
   the ORF 5a; and/or
   the ORF 5b is inactivated.

2. An immunogenic composition comprising an IBV (infectious bronchitis virus), wherein:
   the ORF 3a; and/or
   the ORF 3b; and/or
   the ORF 5a; and/or
   the ORF 5b is inactivated.

3. The IBV or the immunogenic composition of clause 1 or 2, wherein said inactivation of ORF 3a does not affect the expression of ORF S and/or it does not affect the activity of the S protein.

4. The IBV or the immunogenic composition of any one of clauses 1 to 3, wherein said inactivation of ORF 3b does not affect the expression of ORF 3c and/or it does not affect the activity of the E protein.

5. The IBV or the immunogenic composition of any one of clauses 1 to 4, wherein said inactivation of ORF 5b does not affect the expression of ORF N and/or it does not affect the activity of the N protein.

6. The IBV or the immunogenic composition of any one of clauses 1 to 5, wherein said inactivation is a complete or partial deletion of the ORF 3a and/or a partial deletion of ORF 3b and/or a complete or partial deletion of the ORF 5a and/or a partial deletion of ORF 5b, a complete or partial truncation of the ORF 3a and/or a partial truncation of ORF 3b and/or a complete or partial truncation of the ORF 5a and/or a partial truncation of ORF 5b, a complete or partial inversion of the ORF 3a and/or a partial inversion of ORF 3b and/or a complete or partial inversion the ORF 5a and/or a partial inversion of ORF 5b, a complete or partial relocation of the ORF 3a and/or a partial relocation of ORF 3b and/or a complete or partial relocation of the ORF 5a and/or a partial relocation of ORF 5b, an insertion of nucleic acids within the ORF 3a and/or ORF 3b and/or the ORF 5a and/or ORF 5b, a substitution of nucleic acids within the ORF 3a and/or ORF 3b and/or the ORF 5a and/or ORF 5b.

7. The IBV or the immunogenic composition of any one of clauses 1 to 6, wherein said inactivation is a partial deletion of the ORF 3a and/or ORF 3b and/or ORF 5a and/or ORF 5b, a partial truncation of the ORF 3a and/or ORF 3b and/or ORF 5a and/or ORF 5b, a partial inversion of the ORF 3a and/or ORF 3b and/or ORF 5a and/or ORF 5b, a partial relocation of the ORF 3a and/or ORF 3b and/or ORF 5a and/or ORF 5b, an insertion of nucleic acids within the ORF 3a and/or ORF 3b and/or ORF 5a and/or ORF 5b, a substitution of nucleic acids within the ORF 3a and/or ORF 3b and/or ORF 5a and/or ORF 5b.

8. The IBV or the immunogenic composition of any one of clauses 1 to 7, wherein the start codon of ORF 3a and/or ORF 3b and/or ORF 5a and/or ORF 5b is inactivated.

9. The IBV or the immunogenic composition of clause 8, wherein said inactivation of the start codon is a deletion, substitution or inversion.

10. The IBV or the immunogenic composition of clause 8, wherein the ORF 3a is complete or partially deleted, substituted or inverted.

11. The IBV or the immunogenic composition of any one of clauses 1 to 10, wherein the ORF 3a is complete or partially deleted.

12. The IBV or the immunogenic composition of any one of clauses 1 to 11, wherein the start codon of ORF 3a (AUG, nucleotides 1-3 of SEQ ID NO:1) is inactivated.

13. The IBV or the immunogenic composition of clause 12, wherein said inactivation of the start codon is a deletion, substitution or inversion.

14. The IBV or the immunogenic composition of clause 12, wherein said inactivation of the start codon is a deletion.

15. The IBV or the immunogenic composition of any one of clauses 1 to 14, wherein said inactivation of ORF 3a does not affect the expression of ORF S and/or it does not affect the activity of the S protein.

16. The IBV or the immunogenic composition of any one of clauses 1 to 15, wherein the ORF 3a is truncated from the 5'-Terminus of the start codon (AUG, nucleotides 1-3 of SEQ ID NO:1) of ORF 3a.

17. The IBV or the immunogenic composition of any one of clauses 1 to 16, wherein the ORF 3a is truncated from the A, U, or G of the start codon (AUG, nucleotides 1-3 of SEQ ID NO:1) of ORF 3a.

18. The IBV or the immunogenic composition of any one of clauses 1 to 17, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides from the 5'-Terminus of the start codon (AUG, nucleotides 1-3 of SEQ ID NO:1) of the ORF 3a are deleted, substituted, or inverted.

19. The IBV or the immunogenic composition of any one of clauses 1 to 18, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides from the A, U, or G of the start codon (AUG, nucleotides 1-3 of SEQ ID NO:1) of the ORF 3a are deleted, substituted, or inverted.

20. The IBV or the immunogenic composition of any one of clauses 1 to 19, wherein between 1 and 173 nucleotides from the 5'-Terminus of the start codon (AUG, nucleotides 1-3 of SEQ ID NO:1) of the ORF 3a are deleted, substituted, or inverted.

21. The IBV or the immunogenic composition of any one of clauses 1 to 20, wherein between 1 and 173 nucleotides from the A of the start codon (A of AUG, nucleotide 1 of SEQ ID NO:1) or between 1 and 172 nucleotides from the U of the start codon (U of AUG, nucleotide 2 of SEQ ID NO:1) or between 1 and 171 nucleotides from the G of the start codon (G of AUG, nucleotide 3 of SEQ ID NO:1) of the ORF 3a are deleted, substituted, or inverted.

22. The IBV or the immunogenic composition of any one of clauses 1 to 21, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides of the ORF 3a are deleted, substituted, or inverted.

23. The IBV or the immunogenic composition of any one of clauses 1 to 22, wherein between 1 and 173 nucleotides of the ORF 3a are deleted, substituted, or inverted.

24. The IBV or the immunogenic composition of any one of clauses 1 to 23, wherein the ORF 3a from the 5'-Terminus of the start codon (AUG, nucleotides 1-3 of SEQ ID NO:1) of the ORF 3a to nucleotide 173 of SEQ ID NO:1 is deleted, substituted, or inverted.

25. The IBV or the immunogenic composition of any one of clauses 1 to 24, wherein the RNA sequence as set forth in SEQ ID NO:33 is deleted, substituted, or inverted within the ORF 3a.

26. The IBV or the immunogenic composition of any one of clauses 1 to 25, wherein a RNA sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the RNA sequence as set forth in SEQ ID NO:33 is deleted, substituted or inverted within the ORF 3a.

27. The IBV or the immunogenic composition of any one of clauses 1 to 26, wherein the ORF 3b is complete or partially deleted, substituted or inverted.

28. The IBV or the immunogenic composition of any one of clauses 1 to 27, wherein the ORF 3b is complete or partially deleted.

29. The IBV or the immunogenic composition of any one of clauses 1 to 28, wherein the start codon of ORF 3b (AUG, nucleotides 174-176 of SEQ ID NO:1) is inactivated.

30. The IBV or the immunogenic composition of clause 29, wherein said inactivation of the start codon is a deletion, substitution or inversion.

31. The IBV or the immunogenic composition of clause 29, wherein said inactivation of the start codon is a deletion, substitution or inversion.

32. The IBV or the immunogenic composition of any one of clauses 1 to 31, wherein said inactivation of ORF 3b does not affect the expression of ORF 3c and/or it does not affect the activity of the E protein.

33. The IBV or the immunogenic composition of any one of clauses 1 to 32, wherein the ORF 3b is truncated from the 5'-Terminus of the start codon (AUG, nucleotides 174-176 of SEQ ID NO:1) of ORF 3b.

34. The IBV or the immunogenic composition of any one of clauses 1 to 33, wherein the ORF 3b is truncated from the A, U, or G of the start codon (AUG, nucleotides 174-176 of SEQ ID NO:1) of ORF 3b.

35. The IBV or the immunogenic composition of any one of clauses 1 to 34, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides from the 5'-Terminus of the start codon (AUG, nucleotides 174-176 of SEQ ID NO:1) of the ORF 3b are deleted, substituted, or inverted.

36. The IBV or the immunogenic composition of any one of clauses 1 to 35, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides from the A, U, or G of the start codon (AUG, nucleotides 174-176 of SEQ ID NO:1) of the ORF 3b are deleted, substituted, or inverted.

37. The IBV or the immunogenic composition of any one of clauses 1 to 36, wherein between 1 and 175 nucleotides from the 5'-Terminus of the start codon (AUG, nucleotides 174-176 of SEQ ID NO:1) of the ORF 3b are deleted, substituted, or inverted.

38. The IBV or the immunogenic composition of any one of clauses 1 to 37, wherein between 1 and 175 nucleotides from the A of the start codon (A of AUG, nucleotide 174 of SEQ ID NO:1) or between 1 and 174 nucleotides from the U of the start codon (U of AUG, nucleotide 175 of SEQ ID NO:1) or between 1 and 173 nucleotides from the G of the start codon (G of AUG, nucleotide 176 of SEQ ID NO:1) of the ORF 3b are deleted, substituted or inverted.

39. The IBV or the immunogenic composition of any one of clauses 1 to 38, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides of the ORF 3b are deleted, substituted or inverted.

40. The IBV or the immunogenic composition of any one of clauses 1 to 39, wherein between 1 and 175 nucleotides of the ORF 3b are deleted, substituted or inverted.

41. The IBV or the immunogenic composition of any one of clauses 1 to 40, wherein the ORF 3b from the 5'-Terminus of the start codon (AUG, nucleotides 174-176 of SEQ ID NO:1) of the ORF 3b to nucleotide 348 of SEQ ID NO:1 is deleted, substituted or inverted.

42. The IBV or the immunogenic composition of any one of clauses 1 to 41, wherein the RNA sequence as set forth in SEQ ID NO:34 is deleted, substituted or inverted within the ORF 3b.

43. The IBV or the immunogenic composition of any one of clauses 1 to 42, wherein a RNA sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the RNA sequence as set forth in SEQ ID NO:34 is deleted, substituted or inverted within the ORF 3b.

44. The IBV or the immunogenic composition of any one of clauses 1 to 43, wherein the ORF 5a is complete or partially deleted, substituted or inverted.

45. The IBV or the immunogenic composition of any one of clauses 1 to 44, wherein the ORF 5a is complete or partially deleted.

46. The IBV or the immunogenic composition of any one of clauses 1 to 45, wherein the start codon of ORF 5a (AUG, nucleotides 1-3 of SEQ ID NO:2) is inactivated.

47. The IBV or the immunogenic composition of clauses 46, wherein said inactivation of the start codon is a deletion, substitution or inversion.

48. The IBV or the immunogenic composition of clauses 46, wherein said inactivation of the start codon is a deletion.

49. The IBV or the immunogenic composition of any one of clauses 1 to 48, wherein the ORF 5a is truncated from the 5'-Terminus of the start codon of ORF 5a (AUG, nucleotides 1-3 of SEQ ID NO:2).

50. The IBV or the immunogenic composition of any one of clauses 1 to 49, wherein the ORF 5a is truncated from the A, U, or G of the start codon of ORF 5a (AUG, nucleotides 1-3 of SEQ ID NO:2).

51. The IBV or the immunogenic composition of any one of clauses 1 to 50, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides from the 5'-Terminus of the start codon (AUG, nucleotides 1-3 of SEQ ID NO:2) of the ORF 5a are deleted, substituted or inverted.

52. The IBV or the immunogenic composition of any one of clauses 1 to 51, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides from the A, U, or G of the start codon (AUG, nucleotides 1-3 of SEQ ID NO:2) of the ORF 5a are deleted, substituted or inverted.

53. The IBV or the immunogenic composition of any one of clauses 1 to 52, wherein between 1 and 194 nucleotides from the 5'-Terminus of the start codon (AUG, nucleotides 1-3 of SEQ ID NO:2) of the ORF 5a are deleted, substituted, or inverted.

54. The IBV or the immunogenic composition of any one of clauses 1 to 53, wherein between 1 and 194 nucleotides from the A of the start codon (A of AUG, nucleotide 1 of SEQ ID NO:2) or between 1 and 193 nucleotides from the U of the start codon (U of AUG, nucleotide 2 of SEQ ID NO:2) or between 1 and 192 nucleotides from the G of the start codon (G of AUG, nucleotide 3 of SEQ ID NO:2) of the ORF 5a are deleted, substituted or inverted.

55. The IBV or the immunogenic composition of any one of clauses 1 to 54, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides of the ORF 5a are deleted, substituted or inverted.

56. The IBV or the immunogenic composition of any one of clauses 1 to 55, wherein between 1 and 194 nucleotides of the ORF 5a are deleted, substituted, or inverted.

57. The IBV or the immunogenic composition of any one of clauses 1 to 56, wherein the ORF 5a from the 5'-Terminus of the start codon (AUG, nucleotides 1-3 of SEQ ID NO:2) of the ORF 5a to nucleotide 194 of SEQ ID NO:2 is deleted, substituted or inverted.

58. The IBV or the immunogenic composition of any one of clauses 1 to 57, wherein the RNA sequence as set forth in SEQ ID NO:35 is deleted, substituted or inverted within the ORF 5a.

59. The IBV or the immunogenic composition of any one of clauses 1 to 58, wherein a RNA sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the RNA sequence as set forth in SEQ ID NO:35 is deleted, substituted or inverted within the ORF 5a.

60. The IBV or the immunogenic composition of any one of clauses 1 to 59, wherein the ORF 5b is complete or partially deleted, substituted or inverted.

61. The IBV or the immunogenic composition of any one of clauses 1 to 60, wherein the ORF 5b is complete or partially deleted.

62. The IBV or the immunogenic composition of any one of clauses 1 to 61, wherein the start codon (AUG, nucleotides 195-197 of SEQ ID NO:2) of ORF 5b is inactivated.

63. The IBV or the immunogenic composition of clause 62, wherein said inactivation of the start codon is a deletion, substitution or inversion.

64. The IBV or the immunogenic composition of clause 62, wherein said inactivation of the start codon is a deletion.

65. The IBV or the immunogenic composition of any one of clauses 1 to 64, wherein said inactivation of ORF 5b does not affect the expression of ORF N and/or it does not affect the activity of the N protein.

66. The IBV or the immunogenic composition of any one of clauses 1 to 65, wherein the ORF 5b is truncated from the 5'-Terminus of the start codon of ORF 5b (AUG, nucleotides 195-197 of SEQ ID NO:2).

67. The IBV or the immunogenic composition of any one of clauses 1 to 66, wherein the ORF 5b is truncated from the A, U, or G of the start codon of ORF 5b (AUG, nucleotides 195-197 of SEQ ID NO:2).

68. The IBV or the immunogenic composition of any one of clauses 1 to 67, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 90 nucleotides, at least 100 nucleotides, at least 125 nucleotides, at least 150 nucleotides, at least 170 nucleotides, at least 190 nucleotides from the 5'-Terminus of the start codon (AUG, nucleotides 195-197 of SEQ ID NO:2) of the ORF 5b are deleted, substituted or inverted.

69. The IBV or the immunogenic composition of any one of clauses 1 to 68, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 90 nucleotides, at least 100 nucleotides, at least 125 nucleotides, at least 150 nucleotides, at least 170 nucleotides, at least 190 nucleotides from the A, U or G of the start codon (AUG, nucleotides 195-197 of SEQ ID NO:2) of the ORF 5b are deleted, substituted, or inverted.

70. The IBV or the immunogenic composition of any one of clauses 1 to 69, wherein between 1 and 90 nucleotides from the 5'-Terminus of the start codon (AUG, nucleotides 195-197 of SEQ ID NO:2) of the ORF 5b are deleted, substituted, or inverted.

71. The IBV or the immunogenic composition of any one of clauses 1 to 70, wherein between 1 and 191 nucleotides from the 5'-Terminus of the start codon (AUG, nucleotides 195-197 of SEQ ID NO:2) of the ORF 5b are deleted, substituted, or inverted.

72. The IBV or the immunogenic composition of any one of clauses 1 to 71, wherein between 1 and 90 nucleotides from the A of the start codon (A of AUG, nucleotide 195 of SEQ ID NO:2) or between 1 and 89 nucleotides from the U of the start codon (U of AUG, nucleotide 196 of SEQ ID NO:2) or between 1 and 88 nucleotides from the G of the start codon (G of AUG, nucleotide 197 of SEQ ID NO:2) of the ORF 5b are deleted, substituted, or inverted.

73. The IBV or the immunogenic composition of any one of clauses 1 to 72, wherein between 1 and 191 nucleotides from the A of the start codon (A of AUG, nucleotide 195 of SEQ ID NO:2) or between 1 and 190 nucleotides from the U of the start codon (U of AUG, nucleotide 196 of SEQ ID NO:2) or between 1 and 189 nucleotides from the G of the start codon (G of AUG, nucleotide 197 of SEQ ID NO:2) of the ORF 5b are deleted, substituted, or inverted.

74. The IBV or the immunogenic composition of any one of clauses 1 to 73, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 90 nucleotides, at least 100 nucleotides, at least 125 nucleotides, at least 150 nucleotides, at least 170 nucleotides, at least 190 nucleotides of the ORF 5b are deleted, substituted, or inverted.

75. The IBV or the immunogenic composition of any one of clauses 1 to 74, wherein between 1 and 90 nucleotides of the ORF 5b are deleted, substituted or inverted.

76. The IBV or the immunogenic composition of any one of clauses 1 to 75, wherein between 1 and 191 nucleotides of the ORF 5b are deleted, substituted or inverted.

77. The IBV or the immunogenic composition of any one of clauses 1 to 76, wherein the ORF 5b from the 5'-Terminus of the start codon (AUG, nucleotides 195-197 of SEQ ID NO:2) of the ORF 5b to nucleotide 284 of SEQ ID NO:2 is deleted, substituted, or inverted.

78. The IBV or the immunogenic composition of any one of clauses 1 to 77, wherein the RNA sequence as set forth in SEQ ID NO:36 is deleted, substituted or inverted within the ORF 5b.

79. The IBV or the immunogenic composition of any one of clauses 1 to 78, wherein a RNA sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the RNA sequence as set forth in SEQ ID NO:36 is deleted, substituted or inverted within the ORF 5b.

80. The IBV or the immunogenic composition of any one of clauses 1 to 79, wherein a TRS (transcription regulating sequence) is inserted 5' of the ORF N.

81. The IBV or the immunogenic composition of clause 80, wherein said TRS has the sequence CUUAACAA.

82. The IBV or the immunogenic composition of clauses 80 or 81, wherein said TRS (transcription regulating sequence) is inserted for not affecting the expression of ORF N and/or not the activity of the N protein.

83. The IBV or the immunogenic composition of any one of clauses 1 to 82, wherein a sequence comprising stop codons is inserted 5' of the TRS of the ORF N.

84. The IBV or the immunogenic composition of clause 83, wherein said sequence comprising stop codons has a sequence as set forth in SEQ ID NO:37.

85. The IBV or the immunogenic composition of any one of clauses 1 to 84, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 176 nucleotides, at least 180 nucleotides, at least 200 nucleotides, at least 225, nucleotides, at least 250 nucleotides, at least 300 nucleotides, at least 340 nucleotides from the 5'-Terminus of the start codon (AUG, nucleotides 1-3 of SEQ ID NO:1) of the ORF 3a are deleted, substituted or inverted.

86. The IBV or the immunogenic composition of any one of clauses 1 to 85, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 176 nucleotides, at least 180 nucleotides, at least 200 nucleotides, at least 225, nucleotides, at least 250 nucleotides, at least 300 nucleotides, at least 340 nucleotides from the A, U, or G of the start codon (AUG, nucleotides 1-3 of SEQ ID NO:1) of the ORF 3a are deleted, substituted or inverted.

87. The IBV or the immunogenic composition of any one of clauses 1 to 86, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides, at least 195 nucleotides, at least 200 nucleotides, at least 225 nucleotides, at least 250, nucleotides, at least 300 nucleotides, at least 350 nucleotides, at least 380 nucleotides from the 5'-Terminus of the start codon (AUG, nucleotides 1-3 of SEQ ID NO:2) of the ORF 5a are deleted, substituted, or inverted.

88. The IBV or the immunogenic composition of any one of clauses 1 to 87, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides, at least 195 nucleotides, at least 200 nucleotides, at least 225 nucleotides, at least 250, nucleotides, at least 300 nucleotides, at least 350 nucleotides, at least 380 nucleotides from the A, U, or G of the start codon (AUG, nucleotides 1-3 of SEQ ID NO:2) of the ORF 5a are deleted, substituted, or inverted.

89. The IBV or the immunogenic composition of any one of clauses 1 to 88, wherein between 1 and 348 nucleotides from the 5'-Terminus of the start codon (AUG, nucleotides 1-3 of SEQ ID NO:1) of the ORF 3a are deleted, substituted or inverted.

90. The IBV or the immunogenic composition of any one of clauses 1 to 89, wherein between 1 and 348 nucleotides from the A of the start codon (A of AUG, nucleotide 1 of SEQ ID NO:1) or between 1 and 347 nucleotides from the U of the start codon (U of AUG, nucleotide 2 of SEQ ID NO:1) or between 1 and 346 nucleotides from the G of the start codon (G of AUG, nucleotide 3 of SEQ ID NO:1) of the ORF 3a are deleted, substituted, or inverted.

91. The IBV or the immunogenic composition of any one of clauses 1 to 90, wherein between 1 and 385 nucleotides from the 5'-Terminus of the start codon (AUG, nucleotides 1-3 of SEQ ID NO:2) of the ORF 5a are deleted, substituted or inverted.

92. The IBV or the immunogenic composition of any one of clauses 1 to 91, wherein between 1 and 385 nucleotides from the A of the start codon (A of AUG, nucleotide 1 of SEQ ID NO:2) or between 1 and 384 nucleotides from the U of the start codon (U of AUG, nucleotide 2 of SEQ ID NO:2) or between 1 and 383 nucleotides from the G of the start codon (G of AUG, nucleotide 3 of SEQ ID NO:2) of the ORF 5a are deleted, substituted, or inverted.

93. The IBV or the immunogenic composition of any one of clauses 1 to 92, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 176 nucleotides, at least 180 nucleotides, at least 200 nucleotides, at least 225, nucleotides, at least 250 nucleotides, at least 300 nucleotides, at least 340 nucleotides from the 5'-Terminus of the start codon (AUG, nucleotides 1-3 of SEQ ID NO:1) of ORF 3a are deleted, substituted, or inverted within the ORF 3a and/or ORF 3b.

94. The IBV or the immunogenic composition of any one of clauses 1 to 93, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 176 nucleotides, at least 180 nucleotides, at least 200 nucleotides, at least 225, nucleotides, at least 250 nucleotides, at least 300 nucleotides, at least 340 nucleotides from the A, U, or G of the start codon (AUG, nucleotides 1-3 of SEQ ID NO:1) of ORF 3a are deleted, substituted or inverted within the ORF 3a and/or ORF 3b.

95. The IBV or the immunogenic composition of any one of clauses 1 to 94, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides, at least 195 nucleotides, at least 200 nucleotides, at least 225 nucleotides, at least 250, nucleotides, at least 300 nucleotides, at least 350 nucleotides, at least 380 nucleotides from the 5'-Terminus of the start codon (AUG, nucleotides 1-3 of SEQ ID NO:2) of ORF 5a are deleted, substituted, or inverted within the ORF 5a and/or ORF 5b.

96. The IBV or the immunogenic composition of any one of clauses 1 to 95, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides, at least 195 nucleotides, at least 200 nucleotides, at least 225 nucleotides, at least 250, nucleotides, at least 300 nucleotides, at least 350 nucleotides, at least 380 nucleotides from the A, U, or G of the start codon (AUG, nucleotides 1-3 of SEQ ID NO:2) of ORF 5a are deleted, substituted, or inverted within the ORF 5a and/or ORF 5b.

97. The IBV or the immunogenic composition of any one of clauses 1 to 96, wherein between 1 and 348 nucleotides from the 5'-Terminus of the start codon (AUG, nucleotides 1-3 of SEQ ID NO:1) of ORF 3a are deleted, substituted, or inverted within the ORF 3a and/or ORF 3b.

98. The IBV or the immunogenic composition of any one of clauses 1 to 97, wherein between 1 and 348 nucleotides from the A of the start codon (A of AUG, nucleotide 1 of SEQ ID NO:1) or between 1 and 347 nucleotides from the U of the start codon (U of AUG, nucleotide 2 of SEQ ID NO:1) or between 1 and 346 nucleotides from the G of the start codon (G of AUG, nucleotide 3 of SEQ ID NO:1) of ORF 3a are deleted, substituted, or inverted within the ORF 3a and/or ORF 3b.

99. The IBV or the immunogenic composition of any one of clauses 1 to 98, wherein between 1 and 385 nucleotides from the 5'-Terminus of the start codon (AUG, nucleotides 1-3 of SEQ ID NO:2) of the ORF 5a are deleted, substituted, or inverted within the ORF 5a and/or ORF 5b.

100. The IBV or the immunogenic composition of any one of clauses 1 to 99, wherein between 1 and 385 nucleotides from the A of the start codon (A of AUG, nucleotide 1 of SEQ ID NO:2) or between 1 and 384 nucleotides from the U of the start codon (U of AUG, nucleotide 2 of SEQ ID NO:2) or between 1 and 383 nucleotides from the G of the start codon (G of AUG, nucleotide 3 of SEQ ID NO:2) of the ORF 5a are deleted, substituted, or inverted within the ORF 5a and/or ORF 5b.

101. The IBV or the immunogenic composition of any one of clauses 1 to 100, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 176 nucleotides, at least 180 nucleotides, at least 200 nucleotides, at least 225, nucleotides, at least 250 nucleotides, at least 300 nucleotides, at least 340 nucleotides of the ORF 3a and/or ORF 3b are deleted, substituted, or inverted.

102. The IBV or the immunogenic composition of any one of clauses 1 to 101, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides, at least 195 nucleotides, at least 200 nucleotides, at least 225 nucleotides, at least 250, nucleotides, at least 300 nucleotides, at least 350 nucleotides, at least 380 nucleotides of the ORF 5a and/or ORF 5b are deleted, substituted, or inverted.

103. The IBV or the immunogenic composition of any one of clauses 1 to 102, wherein between 1 and 348 nucleotides of the ORF 3a and/or ORF 3b are deleted, substituted, or inverted.

104. The IBV or the immunogenic composition of any one of clauses 1 to 103, wherein between 1 and 385 nucleotides of the ORF 5a and/or ORF 5b are deleted, substituted or inverted.

105. The IBV or the immunogenic composition of any one of clauses 1 to 104, wherein between 1 and 348 nucleotides of the ORF 3a and/or ORF 3b are deleted, substituted or inverted within the 5'-Terminus of the start codon of the ORF 3a and the start codon of the ORF 3c.

106. The IBV or the immunogenic composition of any one of clauses 1 to 105, wherein between 1 and 348 nucleotides of the ORF 3a and/or ORF 3b are deleted, substituted or inverted within the 5'-Terminus of the start codon (AUG, nucleotides 1-3 of SEQ ID NO:1) of the ORF 3a to nucleotide 348 of SEQ ID NO:1.

107. The IBV or the immunogenic composition of any one of clauses 1 to 106, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 176 nucleotides, at least 180 nucleotides, at least 200 nucleotides, at least 225, nucleotides, at least 250 nucleotides, at least 300 nucleotides, at least 340 nucleotides of the ORF 3a and/or ORF 3b are deleted, substituted or inverted within the 5'-Terminus of the start codon of the ORF 3a and the start codon of the ORF 3c.

108. The IBV or the immunogenic composition of any one of clauses 1 to 107, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 176 nucleotides, at least 180 nucleotides, at least 200 nucleotides, at least 225, nucleotides, at least 250 nucleotides, at least 300 nucleotides, at least 340 nucleotides of the ORF 3a and/or ORF 3b are deleted, substituted or inverted within the 5'-Terminus of the start codon (AUG, nucleotides 1-3 of SEQ ID NO:1) of the ORF 3a to nucleotide 348 of SEQ ID NO:1.

109. The IBV or the immunogenic composition of any one of clauses 1 to 108, wherein between 1 and 385 nucleotides of the ORF 5a and/or ORF 5b are deleted, substituted, or inverted within the 5'-Terminus of the start codon of the ORF 5a and the start codon of the ORF N.

110. The IBV or the immunogenic composition of any one of clauses 1 to 109, wherein between 1 and 385 nucleotides of the ORF 5a and/or ORF 5b are deleted, substituted, or inverted within the 5'-Terminus of the start codon (AUG, nucleotides 1-3 of SEQ ID NO:2) of the ORF 5a to nucleotide 385 of SEQ ID NO:2.

111. The IBV or the immunogenic composition of any one of clauses 1 to 110, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides, at least 195 nucleotides, at least 200 nucleotides, at least 225 nucleotides, at least 250, nucleotides, at least 300 nucleotides, at least 350 nucleotides, at least 380 nucleotides of the ORF 5a and/or ORF 5b are deleted, substituted or inverted within the 5'-Terminus of the start codon of the ORF 5a and the start codon of the ORF N.

112. The IBV or the immunogenic composition of any one of clauses 1 to 111, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides, at least 195 nucleotides, at least 200 nucleotides, at least 225 nucleotides, at least 250, nucleotides, at least 300 nucleotides, at least 350 nucleotides, at least 380 nucleotides of the ORF 5a and/or ORF 5b are deleted, substituted or inverted within the 5'-Terminus of the start codon (AUG, nucleotides 1-3 of SEQ ID NO:2) of the ORF 5a to nucleotide 385 of SEQ ID NO:2.

113. The IBV or the immunogenic composition of any one of clauses 1 to 112, wherein the inactivation of ORF 3a and ORF 3b does not affect the expression of ORF 3c and/or it does not affect the activity of the E protein.

114. The IBV or the immunogenic composition of any one of clauses 1 to 113, wherein the inactivation of ORF 3a and ORF 3b does not affect the expression of ORF S and/or it does not affect the activity of the S protein.

115. The IBV or the immunogenic composition of any one of clauses 1 to 114, wherein the inactivation of ORF 5a and ORF 5b does not affect the expression of ORF N and/or it does not affect the activity of the N protein.

116. The IBV or the immunogenic composition of any one of clauses 1 to 115, wherein the ORF 3a is complete or partially deleted, substituted or inverted and wherein the ORF 3b is partially deleted, substituted or inverted.

117. The IBV or the immunogenic composition of any one of clauses 1 to 116, wherein the ORF 5a is complete or partially deleted, substituted or inverted and wherein the ORF 5b is partially deleted, substituted or inverted.

118. The IBV or the immunogenic composition of any one of clauses 1 to 117, wherein the ORF 3a and the ORF 5a are complete or partially deleted, substituted or inverted and wherein the ORF 3b and the ORF 5b are partially deleted, substituted or inverted.

119. The IBV or the immunogenic composition of any one of clauses 1 to 118, wherein the ORF 3a is complete or partially deleted and the ORF 3b is partially deleted.

120. The IBV or the immunogenic composition of any one of clauses 1 to 119, wherein the ORF 5a is complete or partially deleted and the ORF 5b is partially deleted.

121. The IBV or the immunogenic composition of any one of clauses 1 to 120, wherein the ORF 3a and the ORF 5a are complete or partially deleted and the ORF 3b and the ORF 5b are partially deleted.

122. The IBV or the immunogenic composition of any one of clauses 1 to 121, wherein the start codon of ORF 3a and the start codon of ORF 3b are inactivated.

123. The IBV or the immunogenic composition of any one of clauses 1 to 122, wherein the start codon of ORF 3a (AUG, nucleotides 1-3 of SEQ ID NO:1) and the start codon of ORF 3b (AUG, nucleotides 174-176 of SEQ ID NO:1) are inactivated.

124. The IBV or the immunogenic composition of clause 122 or clause 123, wherein said inactivation of the start codon (AUG) of ORF 3a and ORF 3b is a deletion, substitution or inversion.

125. The IBV or the immunogenic composition of any one of clauses 1 to 124, wherein the start codon of ORF 5a and the start codon of ORF 5b are inactivated.

126. The IBV or the immunogenic composition of any one of clauses 1 to 125, wherein the start codon of ORF 5a (AUG, nucleotides 1-3 of SEQ ID NO:2) and the start codon (AUG, nucleotides 195-197 of SEQ ID NO:2) of ORF 5b are inactivated.

127. The IBV or the immunogenic composition of clause 125 or clause 126, wherein said inactivation of the start codon (AUG) of ORF 5a and ORF 5b is a deletion, substitution or inversion.

128. The IBV or the immunogenic composition of any one of clauses 1 to 127, wherein the ORF 3a and ORF 3b are truncated from the 5'-Terminus of the start codon (AUG, nucleotides 1-3 of SEQ ID NO:1) of ORF 3a and ORF 3b (AUG, nucleotides 174-176 of SEQ ID NO:1).

129. The IBV or the immunogenic composition of any one of clauses 1 to 128, wherein the ORF 3a and ORF 3b are truncated from the A, U, or G of the start codon (AUG, nucleotides 1-3 of SEQ ID NO:1) of ORF 3a and ORF 3b (AUG, nucleotides 174-176 of SEQ ID NO:1).

130. The IBV or the immunogenic composition of any one of clauses 1 to 129, wherein the ORF 5a and ORF 5b are truncated from the 5'-Terminus of the start codon of ORF 5a (AUG, nucleotides 1-3 of SEQ ID NO:2) and ORF 5b (AUG, nucleotides 195-197 of SEQ ID NO:2).

131. The IBV or the immunogenic composition of any one of clauses 1 to 130, wherein the ORF 5a and ORF 5b are truncated from the A, U, or G of the start codon of ORF 5a (AUG, nucleotides 1-3 of SEQ ID NO:2) and ORF 5b (AUG, nucleotides 195-197 of SEQ ID NO:2).

132. The IBV or the immunogenic composition of any one of clauses 1 to 131, wherein the ORF 3a and ORF 3b are truncated from the 5'-Terminus of the start codon (AUG) of ORF 3a (AUG, nucleotides 1-3 of SEQ ID NO:1) and the start codon of ORF 3b (AUG, nucleotides 174-176 of SEQ ID NO:1) and wherein the ORF 5a and ORF 5b are truncated from the 5'-Terminus of the start codon of ORF 5a (AUG, nucleotides 1-3 of SEQ ID NO:2) and the start codon ORF 5b (AUG, nucleotides 195-197 of SEQ ID NO:2).

133. The IBV or the immunogenic composition of any one of clauses 1 to 132, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides from the 5'-Terminus of the start codon (AUG, nucleotides 1-3 of SEQ ID NO:1) of the ORF 3a are deleted, substituted or inverted, and, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides from the 5'-Terminus of the start codon (AUG, nucleotides 174-176 of SEQ ID NO:1) of the ORF 3b are deleted, substituted or inverted.

134. The IBV or the immunogenic composition of any one of clauses 1 to 133, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides from the A, U, or G of the start codon (AUG, nucleotides 1-3 of SEQ ID NO:1) of the ORF 3a are deleted, substituted or inverted, and, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides from the A, U, or G of the start codon (AUG, nucleotides 174-176 of SEQ ID NO:1) of the ORF 3b are deleted, substituted, or inverted.

135. The IBV or the immunogenic composition of any one of clauses 1 to 134, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides from the 5'-Terminus of the start codon (AUG, nucleotides 1-3 of SEQ ID NO:2) of the ORF 5a are deleted, substituted, or inverted and, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides from the 5'-Terminus of the start codon (AUG, nucleotides 195-197 of SEQ ID NO:2) of the ORF 5b are deleted, substituted, or inverted.

136. The IBV or the immunogenic composition of any one of clauses 1 to 135, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides from the A, U, or G of the start codon (AUG, nucleotides 1-3 of SEQ ID NO:2) of the ORF 5a are deleted, substituted, or inverted and, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides from the A, U, or G of the start codon (AUG, nucleotides 195-197 of SEQ ID NO:2) of the ORF 5b are deleted, substituted or inverted.

137. The IBV or the immunogenic composition of any one of clauses 1 to 136, wherein between 1 and 173 nucleotides from the 5'-Terminus of the start codon (AUG, nucleotides 1-3 of SEQ ID NO:1) of the ORF 3a are deleted, substituted or inverted, and, wherein between 1 and 175 nucleotides from the 5'-Terminus of the start codon (AUG, nucleotides 174-176 of SEQ ID NO:1) of the ORF 3b are deleted, substituted or inverted.

138. The IBV or the immunogenic composition of any one of clauses 1 to 137, wherein between 1 and 173 nucleotides from the A of the start codon (A of AUG, nucleotide 1 of SEQ ID NO:1) or between 1 and 172 nucleotides from the U of the start codon (U of AUG, nucleotide 2 of SEQ ID NO:1) or between 1 and 171 nucleotides from the G of the start codon (G of AUG, nucleotide 3 of SEQ ID NO:1) of the ORF 3a are deleted, substituted, or inverted and wherein between 1 and 175 nucleotides from the A of the start codon (A of AUG, nucleotide 174 of SEQ ID NO:1) or between 1 and 174 nucleotides from the U of the start codon (U of AUG, nucleotide 175 of SEQ ID NO:1) or between 1 and 173 nucleotides from the G of the start codon (G of AUG, nucleotide 176 of SEQ ID NO:1) of the ORF 3b are deleted, substituted, or inverted.

139. The IBV or the immunogenic composition of any one of clauses 1 to 138, wherein between 1 and 194 nucleotides from the 5'-Terminus of the start codon (AUG, nucleotides 1-3 of SEQ ID NO:2) of the ORF 5a are deleted, substituted or inverted and wherein between 1 and 191 nucleotides from the 5'-Terminus of the start codon (AUG, nucleotides 195-197 of SEQ ID NO:2) of the ORF 5b are deleted, substituted or inverted.

140. The IBV or the immunogenic composition of any one of clauses 1 to 139, wherein between 1 and 194 nucleotides from the A of the start codon (A of AUG, nucleotide 1 of SEQ ID NO:2) or between 1 and 193 nucleotides from the U of the start codon (U of AUG, nucleotide 2 of SEQ ID NO:2) or between 1 and 192 nucleotides from the G of the start codon (G of AUG, nucleotide 3 of SEQ ID NO:2) of the ORF 5a are deleted, substituted, or inverted, and, wherein between 1 and 191 nucleotides from the A of the start codon (A of AUG, nucleotide 195 of SEQ ID NO:2) or between 1 and 190 nucleotides from the U of the start codon (U of AUG, nucleotide 196 of SEQ ID NO:2) or between 1 and 189 nucleotides from the G of the start codon (G of AUG, nucleotide 197 of SEQ ID NO:2) of the ORF 5b are deleted, substituted, or inverted.

141. The IBV or the immunogenic composition of any one of clauses 1 to 140, wherein at least 174 nucleotides, at least 175 nucleotides, at least 176 nucleotides, at least 180, nucleotides, at least 190 nucleotides, at least 200 nucleotides, at least 225 nucleotides, at least 250 nucleotides, at least 300 nucleotides, at least 325 nucleotides, at least 340 nucleotides from the 5'-Terminus of the start codon (AUG, nucleotides 1-3 of SEQ ID NO:1) of ORF 3a are deleted, substituted, or inverted within the ORF 3a and ORF 3b.

142. The IBV or the immunogenic composition of any one of clauses 1 to 141, wherein at least 174 nucleotides, at least 175 nucleotides, at least 176 nucleotides, at least 180, nucleotides, at least 190 nucleotides, at least 200 nucleotides, at least 225 nucleotides, at least 250 nucleotides, at least 300 nucleotides, at least 325 nucleotides, at least 340 nucleotides from the A, U, or G of the start codon (AUG, nucleotides 1-3 of SEQ ID NO:1) of ORF 3a are deleted, substituted or inverted within the ORF 3a and ORF 3b.

143. The IBV or the immunogenic composition of any one of clauses 1 to 142, wherein at least 195 nucleotides, at least 196 nucleotides, at least 197 nucleotides, at least 200, nucleotides, at least 210 nucleotides, at least 220 nucleotides, at least 225 nucleotides, at least 250 nucleotides, at least 300 nucleotides, at least 325 nucleotides, at least 350 nucleotides, at least 380 nucleotides from the 5'-Terminus of the start codon (AUG, nucleotides 1-3 of SEQ ID NO:2) of ORF 5a are deleted, substituted, or inverted within the ORF 5a and ORF 5b.

144. The IBV or the immunogenic composition of any one of clauses 1 to 143, wherein at least 195 nucleotides, at least 196 nucleotides, at least 197 nucleotides, at least 200, nucleotides, at least 210 nucleotides, at least 220 nucleotides, at least 225 nucleotides, at least 250 nucleotides, at least 300 nucleotides, at least 325 nucleotides, at least 350 nucleotides, at least 380 nucleotides from the A, U, or G of the start codon (AUG, nucleotides 1-3 of SEQ ID NO:2) of ORF 5a are deleted, substituted, or inverted within the ORF 5a and ORF 5b.

145. The IBV or the immunogenic composition of any one of clauses 1 to 144, wherein between 174 and 200 nucleotides or between 174 and 300 nucleotides or between 174 and 348 nucleotides from the 5'-Terminus of the start codon (AUG, nucleotides 1-3 of SEQ ID NO:1) of ORF 3a are deleted, substituted, or inverted within the ORF 3a and ORF 3b.

146. The IBV or the immunogenic composition of any one of clauses 1 to 145, wherein between 174 and 348 nucleotides from the A of the start codon (A of AUG, nucleotide 1 of SEQ ID NO:1) or between 173 and 347 nucleotides from the U of the start codon (U of AUG, nucleotide 2 of SEQ ID NO:1) or between 172 and 346 nucleotides from the G of the start codon (G of AUG, nucleotide 3 of SEQ ID NO:1) of ORF 3a are deleted, substituted, or inverted within the ORF 3a and ORF 3b.

147. The IBV or the immunogenic composition of any one of clauses 1 to 146, wherein between 195 and 250 nucleotides or between 195 and 300 nucleotides or between 195 and 350 or between 195 and 385 nucleotides from the 5'-Terminus of the start codon (AUG, nucleotides 1-3 of SEQ ID NO:2) of the ORF 5a are deleted, substituted, or inverted within the ORF 5a and ORF 5b.

148. The IBV or the immunogenic composition of any one of clauses 1 to 147, wherein between 195 and 385 nucleotides from the A of the start codon (A of AUG, nucleotide 1 of SEQ ID NO:2) or between 194 and 384 nucleotides from the U of the start codon (U of AUG, nucleotide 2 of SEQ ID NO:2) or between 193 and 383 nucleotides from the G of the start codon (G of AUG, nucleotide 3 of SEQ ID NO:2) of the ORF 5a are deleted, substituted, or inverted within the ORF 5a and ORF 5b.

149. The IBV or the immunogenic composition of any one of clauses 1 to 148, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides of the ORF 3a are deleted, substituted, or inverted, and, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides of the ORF 3b are deleted, substituted, or inverted.

150. The IBV or the immunogenic composition of any one of clauses 1 to 149, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides of the ORF 5a are deleted, substituted, or inverted, and, wherein at least 1 nucleotide, at least 2 nucleotides, at least 3 nucleotides, at least 4 nucleotides, at least 5 nucleotides, at least 10 nucleotides, at least 15 nucleotides, at least 20 nucleotides, at least 25 nucleotides, at least 50, nucleotides, at least 75 nucleotides, at least 100 nucleotides, at least 125 nucleotides, at least 150 nucleotides, at least 170 nucleotides, at least 190 nucleotides of the ORF 5b are deleted, substituted, or inverted.

151. The IBV or the immunogenic composition of any one of clauses 1 to 150, wherein between 1 and 173 nucleotides of the ORF 3a are deleted, substituted, or inverted, and, wherein between 1 and 175 nucleotides of the ORF 3b are deleted, substituted, or inverted.

152. The IBV or the immunogenic composition of any one of clauses 1 to 151, wherein between 1 and 194 nucleotides of the ORF 5a are deleted, substituted or inverted, and, wherein between 1 and 191 nucleotides of the ORF 5b are deleted, substituted, or inverted.

153. The IBV or the immunogenic composition of any one of clauses 1 to 152, wherein between 176 and 348 nucleotides of the ORF 3a and ORF 3b are deleted, substituted or inverted within the 5'-Terminus of the start codon of the ORF 3a and the start codon of the ORF 3c.

154. The IBV or the immunogenic composition of any one of clauses 1 to 153, wherein between 176 and 348 nucleotides of the ORF 3a and ORF 3b are deleted, substituted or inverted within the 5'-Terminus of the start codon (AUG, nucleotides 1-3 of SEQ ID NO:1) of the ORF 3a to nucleotide 348 of SEQ ID NO:1.

155. The IBV or the immunogenic composition of any one of clauses 1 to 154, wherein at least 176 nucleotides, at least 180 nucleotides, at least 200 nucleotides, at least 225, nucleotides, at least 250 nucleotides, at least 300 nucleotides, at least 340 nucleotides of the ORF 3a and ORF 3b are deleted, substituted or inverted within the 5'-Terminus of the start codon of the ORF 3a and the start codon of the ORF 3c.

156. The IBV or the immunogenic composition of any one of clauses 1 to 155, wherein at least 176 nucleotides, at least 180 nucleotides, at least 200 nucleotides, at least 225, nucleotides, at least 250 nucleotides, at least 300 nucleotides, at least 340 nucleotides of the ORF 3a and ORF 3b are deleted, substituted or inverted within the 5'-Terminus of the start codon (AUG, nucleotides 1-3 of SEQ ID NO:1) of the ORF 3a to nucleotide 348 of SEQ ID NO:1.

157. The IBV or the immunogenic composition of any one of clauses 1 to 156, wherein between 195 and 385 nucleotides of the ORF 5a and ORF 5b are deleted, substituted, or inverted within the 5'-Terminus of the start codon of the ORF 5a and the start codon of the ORF N.

158. The IBV or the immunogenic composition of any one of clauses 1 to 157, wherein between 195 and 385 nucleotides of the ORF 5a and ORF 5b are deleted, substituted, or inverted within the 5'-Terminus of the start codon (AUG, nucleotides 1-3 of SEQ ID NO:2) of the ORF 5a to nucleotide 385 of SEQ ID NO:2.

159. The IBV or the immunogenic composition of any one of clauses 1 to 158, wherein at least 195 nucleotides, at least 200 nucleotides, at least 225 nucleotides, at least 250, nucleotides, at least 300 nucleotides, at least 350 nucleotides, at least 380 nucleotides of the ORF 5a and ORF 5b are deleted, substituted or inverted within the 5'-Terminus of the start codon of the ORF 5a and the start codon of the ORF N.

160. The IBV or the immunogenic composition of any one of clauses 1 to 159, wherein at least 195 nucleotides, at least 200 nucleotides, at least 225 nucleotides, at least 250, nucleotides, at least 300 nucleotides, at least 350 nucleotides, at least 380 nucleotides of the ORF 5a and ORF 5b are deleted, substituted or inverted within the 5'-Terminus of the start codon (AUG, nucleotides 1-3 of SEQ ID NO:2) of the ORF 5a to nucleotide 385 of SEQ ID NO:2.

161. The IBV or the immunogenic composition of any one of clauses 1 to 160, wherein the ORF 3a and ORF 3b from the 5'-Terminus of the start codon (AUG, nucleotides 1-3 of SEQ ID NO:1) of the ORF 3a to nucleotide 348 of SEQ ID NO:1 is deleted, substituted, or inverted.

162. The IBV or the immunogenic composition of any one of clauses 1 to 161, wherein the RNA sequence as set forth in SEQ ID NO:1 is deleted, substituted, or inverted within the ORF 3a and ORF 3b.

163. The IBV or the immunogenic composition of any one of clauses 1 to 162, wherein a RNA sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the RNA sequence as set forth in SEQ ID NO:1 is deleted, substituted, or inverted within the ORF 3a and ORF 3b.

164. The IBV or the immunogenic composition of any one of clauses 1 to 163, wherein the ORF 5a and ORF 5b from the 5'-Terminus of the start codon (AUG, nucleotides 1-3 of SEQ ID NO:2) of the ORF 5a to nucleotide 385 of SEQ ID NO:2 is deleted, substituted, or inverted.

165. The IBV or the immunogenic composition of any one of clauses 1 to 164, wherein the RNA sequence as set forth in SEQ ID NO:2 is deleted, substituted, or inverted within the ORF 5a and ORF 5b.

166. The IBV or the immunogenic composition of any one of clauses 1 to 165, wherein a RNA sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the RNA sequence as set forth in SEQ ID NO:2 is deleted, substituted, or inverted within the ORF 5a and ORF 5b.

167. The IBV or the immunogenic composition of any one of clauses 1 to 166, wherein the E protein has an amino acid sequence of genotype QX, Beaudette, H120 or H52 or a sequence having at least 70%, at least 75%, at least 80%, at least 85%, at least 90%, at least 91%, at least 92%, at least 93%, at least 94%, at least 95%, at least 96%, at least 97%, at least 98%, at least 99% or at least 99.5% sequence identity to at least one of the above mentioned genotypes.

168. The IBV or the immunogenic composition of any one of clauses 1 to 167, wherein the E protein has an amino acid sequence as shown for KM586818 (QX), AJ311317 (Beaudette), FJ807652 (H120) or SEQ ID NO: 38 (H52) or a sequence having at least 70%, at least 75%, at least 80%, at least 85%, at least 90%, at least 91%, at least 92%, at least 93%, at least 94%, at least 95%, at least 96%, at least 97%, at least 98%, at least 99% or at least 99.5% sequence identity to at least one of the above mentioned sequences.

169. The IBV or the immunogenic composition of any one of clauses 1 to 168, wherein the IBV is attenuated.

170. The IBV or the immunogenic composition of any one of clauses 1 to 169, wherein the IBV is genetically engineered.

171. The IBV or the immunogenic composition of any one of clauses 1 to 170, wherein the IBV is a recombinant IBV.

172. The IBV or the immunogenic composition of any one of clauses 1 to 171, wherein the IBV has a genotype selected from a list of strains containing of: Arkansas (such as Arkansas 99), California (such as California 1734/04, California 99), Connecticut, Delaware (such as Delaware 98), Dutch (such as D207, D212, D274, D3128, D3896, D8880, D1466), Florida, Georgia (such as Georgia GA-08, GA-12, GA-13), Gray, Holte, Iowa (such as Iowa 97 and Iowa 69), Italy (such as Italy 02), JMK, Maine (such as Maine 209), Massachusetts (such as M41, Beaudette, 246 G, D 580, H52, H120), Pennsylvania (such as Pennsylvania 1220/98, Pennsylvania Wolg/98), Qu, (such as Qu-mv), QX (such as GB341/96), Q1, SE 17, Variant 2 (such as IS/1494/06) and 4/91 (793B).

173. The IBV or the immunogenic composition of any one of clauses 1 to 172, wherein the IBV is of QX, Massachusetts, 4/91, Q1 or Italy 02 genotype.

174. The IBV or the immunogenic composition of clause 173, wherein the QX genotype is selected from a list containing of: FR-L1450T-05, FR-L1450L-05, NL-L1449T-04, NL-L1449K-04, IBV/Ck/SP/170/09, IBV/Ck/SP/79/08, IBV/Ck/SP/248/09, HBN, IBVQX, LX4, BJQ, CK/CH/LGD/03, GB341/96.

175. The IBV or the immunogenic composition of clause 173, wherein the Massachusetts genotype is selected from a list containing of: H120, H52, Spain/98/308, IBMA5-1, SD/97/01, Beaudette, Spain/96/334, M41-M21883.

176. The IBV or the immunogenic composition of clause 173, wherein the 4/91 genotype is selected from a list containing of: Spain/98/328, Spain/92/35, IR-3654-VM, FR-CR88061-88, FR-85131-85, UK-1233-95, UK/3/91, Spain/00/336, UK/7/91, 4/91-pathogenic, 4/91 attenuated, IB4-91.

177. The IBV or the immunogenic composition of clause 173, wherein the Q1 genotype is selected from a list containing of: CK/CH/LDL/98I, CK/CH/LSD/08-10, J2, Q1, AR08ER22, AR08BA21, Chile-295-10.

178. The IBV or the immunogenic composition of clause 173, wherein the Italy 02 genotype is selected from a list containing of: Spain/99/316, Italy-02, UK-L633-04, It-497-02, Spain/05/866, Spain/04/221, Spain/00/337, Spain/155/09, Spain/03/08.

179. The IBV or the immunogenic composition of any one of clauses 1 to 178, wherein the IBV is of the Massachusetts genotype strain H52.

180. The IBV or the immunogenic composition of any one of clauses 1 to 179, wherein the H52 genotype is H52U.

181. The IBV or the immunogenic composition of any one of clauses 1 to 180, wherein the H52 has a nucleotide sequence as shown for EU817497 or a sequence having at least 95%, at least 96%, at least 97%, at least 98%, at least 99% or at least 99.5% sequence identity thereto.

182. The IBV or the immunogenic composition of any one of clauses 1 to 181, wherein the H52 strain has a Spike (S1) protein having an amino acid sequence as shown for AF352315 or a sequence having at least 95%, at least 96%, at least 97%, at least 98%, at least 99% or at least 99.5% sequence identity thereto.

183. The IBV or the immunogenic composition of any one of clauses 1 to 182, wherein the H52 strain has a Nucleocapsid (N) protein having an amino acid sequence as shown for AY044185 or AF352310 or a sequence having at least 95%, at least 96%, at least 97%, at least 98%, at least 99% or at least 99.5% sequence identity to at least one of the above mentioned sequences.

184. The IBV or the immunogenic composition of any one of clauses 1 to 183, wherein the H52 strain has an Envelope (E) protein having an amino acid sequence as shown for AF317210 or a sequence having at least 95%, at least 96%, at least 97%, at least 98%, at least 99% or at least 99.5% sequence identity thereto.

185. The IBV or the immunogenic composition of any one of clauses 1 to 184, wherein the H52 strain has a Membrane glycoprotein (M) protein having an amino acid sequence as shown for AF286185 or a sequence having at least 95%, at least 96%, at least 97%, at least 98%, at least 99% or at least 99.5% sequence identity thereto.

186. The IBV or the immunogenic composition of any one of clauses 1 to 185, wherein the IBV is not N1/88, Q3/88, V18/91 or V6/92.

187. The immunogenic composition of any one of clauses 2 to 186, wherein the immunogenic composition is a vaccine.

188. The immunogenic composition of any one of clauses 2 to 187, wherein the immunogenic composition comprises a pharmaceutically acceptable carrier.

189. The immunogenic composition of clause 188, wherein the pharmaceutically acceptable carrier is phosphate buffered saline.

190. The immunogenic composition of any one of clauses 2 to 189, wherein the immunogenic composition is effective in the treatment and/or prophylaxis of clinical signs caused by IBV in a subject of need.

191. The immunogenic composition of any one of clauses 2 to 190, wherein the immunogenic composition protects against a homologous challenge.

192. The immunogenic composition of any one of clauses 2 to 191, wherein the immunogenic composition protects against a challenge with M41.

193. The immunogenic composition of any one of clauses 2 to 192, wherein said immunogenic composition is formulated for a single-dose administration.

194. The immunogenic composition of any one of clauses 2 to 193, wherein said immunogenic composition is administered subcutaneously, intramuscularly, oral, in ovo, via spray, via drinking water or by eye drop.

195. The immunogenic composition of any one of clauses 2 to 194, wherein the immunogenic composition comprises 1 to 10 $\log_{10}$ $EID_{50}$ of the IBV.

196. The immunogenic composition of any one of clauses 2 to 195, wherein the immunogenic composition comprises 2 to 5 $\log_{10}$ $EID_{50}$ of the IBV.

197. The immunogenic composition of any one of clauses 2 to 196, wherein the immunogenic composition comprises 2 to 4 $\log_{10}$ $EID_{50}$ of the IBV.

198. The IBV or the immunogenic composition of any one of clauses 1 to 197, wherein the ORF 3a is inactivated.

199. The IBV or the immunogenic composition of any one of clauses 1 to 197, wherein the ORF 3b is inactivated.

200. The IBV or the immunogenic composition of any one of clauses 1 to 197, wherein the ORF 5a is inactivated.

201. The IBV or the immunogenic composition of any one of clauses 1 to 197, wherein the ORF 5b is inactivated.

202. The IBV or the immunogenic composition of any one of clauses 1 to 197, wherein the ORF 3a and ORF 3b is inactivated.

203. The IBV or the immunogenic composition of any one of clauses 1 to 197, wherein the ORF 3a and ORF 5a is inactivated.

204. The IBV or the immunogenic composition of any one of clauses 1 to 197, wherein the ORF 3a and ORF 5b is inactivated.

205. The IBV or the immunogenic composition of any one of clauses 1 to 197, wherein the ORF 3b and ORF 5a is inactivated.

206. The IBV or the immunogenic composition of any one of clauses 1 to 197, wherein the ORF 3b and ORF 5b is inactivated 207. The IBV or the immunogenic composition of any one of clauses 1 to 197, wherein the ORF 5a and ORF 5b is inactivated.

208. The IBV or the immunogenic composition of any one of clauses 1 to 197, wherein the ORF 3a and ORF 3b and ORF 5a is inactivated.

209. The IBV or the immunogenic composition of any one of clauses 1 to 197, wherein the ORF 3a and ORF 3b and ORF 5b is inactivated.

210. The IBV or the immunogenic composition of any one of clauses 1 to 197, wherein the ORF 5a and ORF 5b and ORF 3a is inactivated.

211. The IBV or the immunogenic composition of any one of clauses 1 to 197, wherein the ORF 5a and ORF 5b and ORF 3b is inactivated.

212. The IBV or the immunogenic composition of any one of clauses 1 to 197, wherein the ORF 3a and ORF 3b and ORF 5a and ORF 5b is inactivated.

213. An immunogenic composition comprising an IBV (infectious bronchitis virus) of any one of clauses 1 to 212, wherein the ORF 3a is inactivated.

214. An immunogenic composition comprising an IBV (infectious bronchitis virus) of any one of clauses 1 to 212, wherein the ORF 3b is inactivated.

215. An immunogenic composition comprising an IBV (infectious bronchitis virus) of any one of clauses 1 to 212, wherein the ORF 5a is inactivated.

216. An immunogenic composition comprising an IBV (infectious bronchitis virus) of any one of clauses 1 to 212, wherein the ORF 5b is inactivated.

217. An immunogenic composition comprising an IBV (infectious bronchitis virus) of any one of clauses 1 to 212, wherein the ORF 3a and ORF 3b are inactivated.

218. An immunogenic composition comprising an IBV (infectious bronchitis virus) of any one of clauses 1 to 212, wherein the ORF 5a and ORF 5b are inactivated.

219. An immunogenic composition comprising an IBV (infectious bronchitis virus) of any one of clauses 1 to 212, wherein the ORF 3a and ORF 3b and the ORF 5a and ORF 5b are inactivated.

220. A kit comprising the IBV or the immunogenic composition of any one of clauses 1 to 219.

221. The kit according to clause 220, wherein the kit further comprises an instruction letter for the treatment and/or prophylaxis of diseases of avians.

222. The kit according to clause 221, wherein the kit further comprises an instruction letter for the treatment and/or prophylaxis of diseases of poultry.

223. The kit according to clause 222, wherein the kit further comprises an instruction letter for the treatment and/or prophylaxis of IB.

224. A method for immunizing a subject comprising administering to such subject an immunogenic composition according to any one of clauses 2 to 219.

225. A method of treating or preventing clinical signs caused by IBV in a subject of need, the method comprising administering to the subject a therapeutically effective amount of an immunogenic composition according to any one of clauses 2 to 219.

226. A method of reducing the ciliostasis in a subject of need, in comparison to a subject of a non-immunized control group of the same species, the method comprising administering to the subject a therapeutically effective amount of an immunogenic composition according to any one of clauses 2 to 219.

227. The immunogenic composition according to any one of clauses 2 to 219 for use in a method for immunizing a subject, the method comprising administering to the subject a therapeutically effective amount of said immunogenic composition.

228. The immunogenic composition according to any one of clauses 2 to 219 for use in a method of treating or preventing clinical signs caused by IBV in a subject of need, the method comprising administering to the subject a therapeutically effective amount of said immunogenic composition.

229. The immunogenic composition according to any one of clauses 2 to 219 for use in a method of reducing the ciliostasis in a subject of need, in comparison to a subject of a non-immunized control group of the same species, the method comprising administering to the subject a therapeutically effective amount of said immunogenic composition.

230. The method or use of any one of clauses 224 to 229, wherein said subject is avian.

231. The method or use of any one of clauses 224 to 230, wherein said subject is poultry.

232. The method or use of any one of clauses 224 to 231, wherein said subject is selected from the list consisting of chicken, turkey, quail, or pheasant.

233. The method or use of any one of clauses 224 to 232, wherein the immunogenic composition is administered once.

234. The method or use of any one of clauses 224 to 232, wherein the immunogenic composition is administered at two or more doses.

235. The method or use of any one of clauses 224 to 234, wherein said immunogenic composition is administered subcutaneously, intramuscularly, oral, in ovo, via spray, via drinking water or by eye drop.

236. The method or use of any one of clauses 224 to 235, wherein said immunogenic composition is administered via eye drop.

237. The method or use of any one of clauses 224 to 236, wherein the immunogenic composition comprises 1 to 10 $\log_{10}$ $EID_{50}$ of the IBV.

238. The method or use of any one of clauses 224 to 237, wherein the immunogenic composition comprises 2 to 5 $\log_{10}$ $EID_{50}$ of the IBV.

239. The method or use of any one of clauses 224 to 238, wherein the immunogenic composition comprises 2 to 4 $\log_{10}$ $EID_{50}$ of the IBV.

240. The method or use of any one of clauses 224 to 239, wherein the immunogenic composition is administered to subjects within the first week of age, within the first three days of age, within the first two days of age, or within the first day of age.

241. The method or use of any one of clauses 224 to 240, wherein the immunogenic composition is administered to subjects within the first day of age.

242. The method or use of any one of clauses 224 to 241, wherein said method results in an improvement in an efficacy parameter selected from the group consisting of: prevention or reduction of ciliostasis, prevention or reduction of rales, prevention or reduction of egg drop, prevention or reduction of kidney lesions, prevention or reduction of watery diarrhea, prevention or reduction in weight loss, a lower virus load, a reduced viral shedding or combinations thereof, in comparison to a subject of a non-treated control group of the same species.

243. The method or use of any one of clauses 224 to 242, wherein the treatment or prevention results in a prevention or reduction of ciliostasis as compared to subjects of a non-treated control group of the same species.

244. The method or use of any one of clauses 224 to 243, wherein the treatment or prevention results in a prevention or reduction of kidney lesions as compared to subjects of a non-treated control group of the same species.

245. The method or use of any one of clauses 224 to 244, wherein the treatment or prevention results in a prevention or reduction of egg drop as compared to subjects of a non-treated control group of the same species.

246. The IBV or immunogenic composition of any one of clauses 1 to 219 for therapeutic use.

247. The IBV or immunogenic composition of any one of clauses 1 to 219 for use as an immunogen or vaccine.

248. The IBV or immunogenic composition any one of clauses 1 to 219 for use as a medicament.

249. Use of the IBV or immunogenic composition of any one of clauses 1 to 219 for the manufacture of a medicament.

250. Use of the IBV or immunogenic composition of any one of clauses 1 to 219 for the treatment and/or prophylaxis of IBV infections in a subject.

EXAMPLES

The following examples are set forth below to illustrate specific embodiments of the present invention. These examples are merely illustrative and are understood not to limit the scope or the underlying principles of the present invention.

Example 1

Construction of Plasmids

Construction of IBV Donor Plasmid

Strain IBV-H52 (Boehringer Ingelheim, Ingelheim, Germany) was used. The design of the donor plasmids was principally followed by Kuo et al. 2000 (J. Virol. 74:1393-1406). Donor plasmid p-IBV was constructed from the subsequent ligation of five subplasmids: p-IBV-5, p-IBV-1b, p-IBV-S, p-IBV-SIR and p-IBV-3T (Table 1).

TABLE 1

Overview of subplasmids

| Plasmid | Genes | Coordinates | Length (nt) | 3'-end RES[a] |
|---|---|---|---|---|
| p-IBV-5 | IBV 5'-UTR | 1-497 | 497 | BstBI |
| p-IBV-1b | IBV 3'-end 1b, S (ss) | 19610-20379 | 770 | XhoI |
| p-IBV-S | IBV S (ec) | 20379-23590 | 3211 | StyI |
| p-IBV-SIR | IBV S (tm, en), 3a, 3b, E, M | 23591-25318 | 1728 | EcoRI |
| P-IBV-3T | IBV 5a, 5b, N, 3'-UTR | 25319-27640 | 2322 | MssI, PacI |
| p-MHV-S | MHV S (ec) | n.a. | 3757 | StyI |

(ss) = signal sequence;
(ec) = ectodomain;
(tm) = transmembrane domain;
(en) = endodomain;
n.a. = not applicable;
[a]BstBI is present in gene 1b, but not completely present in the 5'-UTR; XhoI was silently introduced.

Plasmid IBV-5 comprises the near full-length 5'-untranslated region (UTR). Plasmid IBV-1b comprises the last 754 nt of the pol 1b gene, including the 50 nt overlap with the spike gene, and the first 66 nt of the spike gene, including the nucleotide sequence encoding the spike protein signal sequence. Plasmid IBV-S contains the near full length ectodomain of the spike gene, 3211 nt in length. Plasmid IBV-SIR comprises the last 212 nt of the spike gene (the transmembrane and the endodomain), the accessory gene 3, the envelope gene, the membrane gene and half of the intergenic region (IR). Plasmid IBV-3T comprises the 3'-terminal region of the IBV genome, including the second half of the IR, the accessory gene 5, the nucleocapsid gene, the 3'-UTR and a 100 nt poly-A sequence.

All plasmid junctions are naturally existing restriction enzyme cleavage sites (RES), except for the XhoI site connecting p-IBV-1b and p-IBV-S, which was silently introduced. RES were made unique by silently removing these RES from other parts of the viral genome included in the donor plasmid (Table 2).

TABLE 2 silent mutations introduced in rIBV

| Gene | Location | | Wt sequence | Rec sequence | RE | Function |
|---|---|---|---|---|---|---|
| 1b | 20247 | . . . 20252 | TTGAAA | oTtAAg | AflII | n.a. |
| 1b | 20283 | . . . 20290 | TTAATTAA | TTgATaAA | PacI | Removed |
| S | 20379 | . . . 20384 | CAGTAG | ctcgAG | XhoI | Exchange S |
| S | 21356 | . . . 21361 | TCAATTG | agtATTG | MfeI | Removed |
| S | 21636 | . . . 21641 | CCAAGG | CCAgGG | StyI | Removed |
| S | 21995 | . . . 22000 | TCAATTG | agtATTG | MfeI | Removed |
| S | 22018 | . . . 22023 | CAATTG | CAgTTa | MfeI | Removed |
| S | 22114 | . . . 22119 | ACGCGT | ACtCGg | MluI | Removed |
| S | 22480 | . . . 22485 | CTTAAG | CTgAAa | AflII | Removed |
| S | 22564 | . . . 22569 | ACTAGT | ACaAGc | SpeI | Removed |
| S | 23604 | . . . 23609 | GTTAGC | GcTAGC | NheI | Deletion 3ab |
| 3a | 23817 | . . . 23822 | ACGTCC | ACtagt | SpeI | n.a. |
| 3a | 23888 | . . . 23893 | AGCGCT | tGCcCT | AfeI | Removed |
| 3b | 24002 | . . . 24007 | ACTGGT | ACcGGT | AgeI | n.a. |
| E | 24200 | . . . 24205 | AGCGCT | gGCaCT | AfeI | Removed |
| E | 24299 | . . . 24304 | TACATG | cACgTG | PmlI | Deletion 3ab |
| M | 24574 | . . . 24579 | ACAAGA | ACgcGt | MluI | n.a. |
| IR | 25467 | . . . 25472 | AGCGCT | n.a. | AfeI | Deletion 5ab |
| 5a | 25500 | . . . 25505 | ACTAGT | n.a. | SpeI | n.a. |
| 5a | 25595 | . . . 25600 | ACGCGT | gCGaGT | MluI | Removed |
| 5b | 25825 | . . . 25830 | CCAAGG | tCAgGG | StyI | Removed |

TABLE 2 -continued silent mutations introduced in rIBV

| Gene | Location | Wt sequence | Rec sequence | RE | Function |
|---|---|---|---|---|---|
| N | 25969 . . . 25974 | GCATCT | GCtagc | NheI | Deletion 5ab |
| N | 26792 . . . 26797 | CACGTG | CtaGgG | PmlI | Removed |
| N | 26857 . . . 26862 | ACGCGT | ACtCGg | MluI | Removed |
| N | 27053 . . . 27058 | CCAAGG | CgAAaG | StyI | Removed |

In addition, semi-unique RES were introduced by silent mutations within 200 nt up- and downstream of the accessory genes 3 and 5, allowing their manipulation. Finally, unique RES MssI and PacI were included after the poly-A sequence, allowing linearization of the plasmid by a single restriction enzyme cleavage. All plasmids were generated by GenScript (Piscataway, N.J., USA) and provided in the plasmid pUC57-simple, a standard cloning plasmid with the polylinker removed.

All genome fragments were ligated step-by-step into p-IBV-5 using the restriction enzymes specified in table 1, and subsequently transformed using HB101 competent cells. The final plasmid consisted of p-IBV-5-1b-S-SIR-3T, now called p-IBV. Composition of the plasmids was checked each step by PCR, restriction enzyme digestion and sequencing of the inserts (Macrogen, Seoul, South Korea).

Construction of mIBV Donor Plasmid

The ectodomain of the MHV spike encoding gene from Vennema et al., 1996 (EMBO J. 15:2020-2028) was amplified from pTUG/pTUMS by PCR using primers with a XhoI overhang (Table 3) and ligated into pJet1.2 resulting in p-MHV-S. Site directed mutagenesis (SDM) with the Q5 SDM kit (New England Biolabs, Ipswich, USA) was used to silently remove an EcoRI and a XhoI RES interfering with subsequent cloning steps (Table 3).

TABLE 3

Primer sequences for cloning and SDM

| Primer | Sequence (5'→3')[a] | Function |
|---|---|---|
| XhoI-t-MHV-S.F01 | CTCGAGTTATATTGGTGATTTTAGATGTATCCAG (SEQ ID NO: 3) | Cloning MHV S |
| MHV-S-StyI-XhoI.R01 | CTCGAGCCAAGGCCATTTCACATACATTTC (SEQ ID NO: 4) | Cloning MHV S |
| pMHV-S-SDM414.F02 | AGCTTGTGAACTCAAACGGTG (SEQ ID NO: 5) | SDM EcoRI |
| pMHV-S-SDM414.R02 | GGATACATCTAAAATCACCAATATAAC (SEQ ID NO : 6) | SDM EcoRI |
| pMHV-S-SDM2823.F03 | TTACTATAAGTTCGAGACTGCC (SEQ ID NO: 7) | SDM XhoI |
| pMHV-S-SDM2823.R03 | CACCCTGCATTAATGCAC (SEQ ID NO: 8) | SDM XhoI |
| IBV-H52_N_ATG_FW | ACCATGGCGAGCGGTAAGA (SEQ ID NO: 9) | N-transcript |

TABLE 3 -continued

Primer sequences for cloning and SDM

| Primer | Sequence (5'→3')[a] | Function |
|---|---|---|
| IBV-M41-#2-IR-RV | TTTTTTTTTTTTTTTTTTGCTCTAACTCTATACTAG (SEQ ID NO: 10) | N-transcript |

[a]XhoI restriction enzyme sites in primers XhoI-t-MHV-S.F01 and MHV-S-StyI-XhoI.R01 are in italics; an additional thymine residue to keep the MHV spike gene ectodomain sequence in frame with the IBV spike gene signal sequence is in bold.

The ectodomain of MHV spike was ligated into p-IBV-5-1b, followed in subsequent cloning steps by the IBV fragments SIR and 3T, resulting in p-IBV-5-1b-mhvS-SIR-3T, now called p-mIBV.

Construction of delta plasmids with double and quadruple deletions of the genes encoding for 3ab and 5ab.

The accessory genes 3 and 5 were deleted. In silico design of the delta 3ab fragment (Δ3ab) was as such that the 1 nt overlap between the stop-codon of the spike gene and the ATG-codon of the 3a gene was replaced by an overlap between the stop-codon of the spike gene and the ATG-codon of the envelope gene. The now non-coding 20 nt overlap between the 3'-end of the 3b-gene and the envelope gene hence remained present. The TRS (transcription regulating sequence) located at the 3'-end of the spike gene to form the subgenomic RNA starting with gene 3a is expected to remain functional, but now starting with the envelope gene. Design of the delta 5ab fragment (Δ5ab) was as such that the ATG-codon of the 5a gene is now the ATG-codon of the nucleocapsid gene. The now non-coding 58 nt overlap between the 3'-end of the 5b-gene and the nucleocapsid gene hence remained present. The TRS located at the 3'-end of the 5b gene to form the subgenomic RNA comprising the nucleocapsid gene was removed together with gene 5b; but the TRS at the 3'-end of the IR is expected to remain functional, now used to form a subgenomic RNA starting with the nucleocapsid gene.

DNA fragments spanning from the semi-unique RES surrounding the accessory genes 3 and 5, with the deletions designed as described above (Δ3ab and Δ5ab), were generated and ligated into pUC57-simple by Genscript. Delta3ab was ligated into p-IBV-5-1b-S-SIR after NheI-PmlI double digestion to remove the 3ab gene, followed by the 3T region to form p-IBV-5-1b-S-SIRΔ3ab-3T, now called p-IBV-Δ3ab. Delta5ab was ligated into p-IBV-3T after AfeI-NheI double digestion to remove the 5ab gene. Fragment 3TΔ5ab was subsequently ligated after p-IBV-5-1b-S-SIR or p-IBV-5-1b-S-SIRΔ3ab to form p-IBV-5-1b-S-SIR-3TΔ5ab and p-IBV-5-1b-S-SIRΔ3ab-3TΔ5ab, respectively, now called p-IBV-Δ5ab and p-IBV-Δ3ab5ab.

Construction of N Transcript Plasmid

A RNA transcription plasmid comprising the nucleocapsid gene and 3'-UTR sequence of IBV H52 strain was generated by RT-PCR amplifying the respective region using primers IBV-H52.N.ATG.FW and IBV-M41.#2.IR.RV (Table 3). The amplicon was ligated into pJet1.2, resulting in p-IBV-N, which was verified by sequencing.

Example 2

Generation of Attenuated IBV

In Vitro Transcription

Capped, run-off donor transcripts were synthesized from p-IBV, p-mIBV and p-IBV-N using the mMessage mMachine T7 kit (Ambion by Thermo Fisher Scientific). In brief, p-mIBV was PacI-linearized, and p-IBV and p-IBV-N were MssI-linearized. Linearized plasmid DNA was ethanol precipitated. Transcription reactions were prepared according to the manufacturer's instructions, using 1.5 and 0.5 µg linearized DNA per 10 ul reaction for p-(m)IBV and p-IBV-N, respectively. After 1 hour of incubation at 37° C., production of RNA was tested by analyzing 1 µl of the reaction volume using gel electrophoreses. After a total of 2 h of incubation, the reaction was stopped by transferring the reaction tubes on ice.

Targeted RNA Recombination and Rescue of mIBV

The IBV spike gene was replaced by a chimeric MHV-IBV spike gene in the IBV genome by targeted RNA recombination between p-mIBV generated donor RNA and recipient virus (IBV) RNA, as essentially described before Kuo et al. 2000 (J. Virol. 74:1393-1406). As infection of most IBV is not possible in continuous cell lines, IBV viral RNA was transfected into BHK-21 cells instead, a cell line known to support replication of the cell culture-adapted IBV strain Beaudette. Twenty microliters of IBV-H52 viral RNA, together with 10 µl transcript reaction mixtures of p-mIBV and p-IBV-N, were transfected into BHK-21 cells by electroporation using two pulses at 850V and 25 µF in a Gene Pulser electroporation apparatus (Bio-Rad). Transfected BHK-21 cells were seeded onto monolayers of LR7 cells and incubated at 37° C.

At 2 days post transfection, when syncytia in the LR7 monolayer were observed, the supernatant was harvested and viruses were purified by two rounds of plaque purification on LR7 cells. Characterization of the last one-third of the genome of candidate recombinants was done by RT-PCR and Sanger sequencing, using the primer sets specified in Table 4. Stocks from murinized IBV (m)IBV strain #1B3-IIA were grown and titrated on LR7 cells.

Targeted RNA Recombination and Rescue of Recombinant IBV

Recombinant IBV (rIBV-wt) was generated by introducing the IBV spike ectodomain back into the mIBV genome by targeted RNA recombination between p-IBV-generated donor RNA and recipient virus mIBV. LR7 cells were infected with mIBV at an MOI (multiplicity of infection) of 0.4 for 4 hours. Capped, runoff donor transcripts from p-IBV were transfected into the mIBV infected LR7 cells by using two pulses at 850 V and 50 pF. Electroporated LR7 cells were diluted to 2 ml in warm DMEM and tenfold dilutions from $10^0$ to $10^{-3}$ were prepared. Two hundred microliters of LR7 cell suspensions were intra-allantoically injected in 10 day old embryonated SPF chicken eggs, 5 eggs per dilution. The eggs were candled twice daily and scored for embryonic death. Upon death, or after 7 days, the eggs were transferred to 4° C., and 16-24 h later the AF was collected aseptically for RT-qPCR, and the chorioallantoic membrane (CAM) of each egg was fixed in 10% formalin for IHC. The AF from eggs inoculated with the highest dilution of electroporated LR7 cells, in which virus was detected by RT-qPCR and IHC, was subjected to two additional rounds of end-point dilution in 8 day-old ECE. Genetic characterization of candidate recombinants was done by RT-PCR and Sanger sequencing, using the primer sets specified in Table 4.

TABLE 4 primer sequences

| Primer set | Target | Primer | Sequence (5'→3')[a] | Amplicon (bp)[b] |
|---|---|---|---|---|
| A | IBV 1a-<br>IBV 1a | IBV.F02<br>IBV.R02 | GGTGTAACACCAGAGATAA<br>ATG (SEQ ID NO: 11)<br>ATTTACGACGTCAAGAGCG<br>TC (SEQ ID NO: 12) | 1416 |
| B | MHV 1b-<br>MHV S | 1173<br>1127 | GACTTAGTCCTCTCCTTGA<br>TTG (SEQ ID NO: 13)<br>CCAGTAAGCAATAATGTGG<br>(SEQ ID NO: 14) | 2479 |
| C | IBV 1b-<br>IBV S | IBV.F73<br>IBV.R73 | TCAGCATGGACGTGTGGTT<br>A (SEQ ID NO: 15)<br>CCCCATGTAAATGCCAACC<br>A (SEQ ID NO: 16) | 992 |
| D | IBV S-<br>IBV S | IBV.F14<br>IBV.R13 | TAAATGGTGATCTTGTTT<br>(SEQ ID NO: 17)<br>CGCTCTTAGTAACATAAAC<br>(SEQ ID NO: 18) | 708 |
| E | IBV S-<br>IBV M | IBV.F15<br>IBV.R15 | TGCTGCTTCCTTTAATAAG<br>(SEQ ID NO: 19)<br>CTGCGACAAGACCTCCTG<br>(SEQ ID NO: 20) | 1994<br>(1646) |
| F | IBV 1b-<br>MHV S | mIBV.F47<br>mIBV.R47 | TCAGCATGGACGTGTGGTT<br>A (SEQ ID NO: 21)<br>CCCAGGCCTTGTGAAACTT<br>C (SEQ ID NO: 22) | 1035 |
| G | MHV S-<br>MHV S | MHV.F05<br>MHV.R05 | ACCCTCCGCTACTACGTTT<br>T (SEQ ID NO: 23)<br>AGGCAGGTATCATGTGACC<br>A (SEQ ID NO: 24) | 966 |
| H | MHV S-<br>IBV M | MHV.F08<br>IBV.R37 | GGATGGGTTTGATGCAACC<br>A (SEQ ID NO: 25)<br>GAGAAAGCACCATTGGCAC<br>A (SEQ ID NO: 26) | 2129 |
| I | IBV IR-<br>IBV N | IBV.F28<br>IBV.R16 | TGTTGTAGGTTGTGGTCCC<br>A (SEQ ID NO: 27)<br>CTGAGGTCAATGCCTTATC<br>(SEQ ID NO: 28) | 1633<br>(1248) |

[a]Sequences of primers IBV.F73 and mIBV.F47 are identical.
[b]For primer sets [E] and [I] amplicon lengths for the rIBV delta variants in which genes 3 and/or 5 are deleted are given in brackets Immunofluorescence Double Stainings for IBV, mIBV and MHV Biological characterization of the chimeric nature of mIBV was performed by immunofluorescence double staining for IBV and MHV. BHK-21 and LR7 cells were propagated on coverslips and inoculated with IBV Beaudette, and MHV A59 and mIBV #1B3-IIA, respectively, at an MOI of 1.0. Cells were fixed with PBS 4% paraformaldehyde (Aurion, Wageningen, The Netherlands) for 20 min at RT after 8, 51/4 and 10 hpi for IBV, MHV and mIBV, respectively, during the first round of infection. Cells were permeabilized with PBS containing 0.1% Triton X-100, incubated with normal goat serum (NGS), and incubated for 45-60 min with a combination of two primary antibodies in NGS: rabbit anti-MHV polyserum k134 [Rottier et al, 1981, J. Virol. 38:20-26] diluted 1:400 and chicken anti-IBV-H120 serum diluted 1:400, or mouse MAb Ch/IBV 26.1 [Thermo Fisher Scientific] diluted 1:200. The chicken anti-IBV-H120 serum was obtained after repeated immunizations of SPF chicken with the IBV strain H120. Cells were washed three times with PBS 0.05% Tween-20 and incubated in the dark for 45 min with a combination of two fluorochrome-labelled secondary antibodies diluted 1:200 in NGS: Alexa Fluor 488 Goat anti-Chicken IgY and Alexa Fluor 568 Goat anti-Rabbit IgG, or Alexa Fluor 488 Goat anti-Mouse IgG and Alexa Fluor 568 Goat anti-Rabbit IgG [Invitrogen as part of Thermo Fisher Scientific]. Cells were washed three times and nuclei were stained with 300 nM DAPI in PBS for 5-10 min in the dark. Cells were washed once with milliQ and mounted with Fluorsave (Calbiochem by Merck Millipore, Billerica, Mass., USA). Slides were viewed using an Olympus BX60 microscope with filters I3, A and N2.1 with a Leica DFC425C color CCD and Leica LAS-AF software (Leica Microsystems, Wetzlar, Germany).

In Ovo Growth Curves of Recombinant IBV Variants

Eight day-old ECE were inoculated with $10^3$ $ELD_{50}$ of IBV-H52, recombinant IBV wild-type (rIBV-wt the amino acid sequences of this virus is identical to the amino acid sequence of IBV H52, but the nucleotide sequence differs due to so called silent mutations in the genomic sequence), rIBV-Δ3ab, rIBV-Δ5ab or rIBV-Δ3ab5ab. Eggs were candled twice daily and after 0, 12, 24, 36, 48, 60 and 72 h of incubation, five predetermined eggs per virus strain were transferred to 4° C. for 16-24 h, and AF was aseptically harvested and stored at −80° C. If one or more embryos per virus strain died ≥12 h prior to the predetermined time-point of collection, that time-point was excluded from further analysis. Allantoic fluid samples were 10-fold diluted in PBS without Ca and Mg, and nucleic acids were extracted with the QIAamp DNA Blood Mini kit (Qiagen) and the addition of carrier RNA using the Hamilton Starlet pipet robot (Reno, Nev., USA). Extracted nucleic acids were analyzed by RT-qPCR for the amount of IBV RNA with a protocol adapted from Callison et al. 2006 (J. Virol. Methods. 138:60-65). Briefly, the same primers and probe were applied and the thermoprofile was adapted for use of the ABI TaqMan Fast Virus 1-Step Master Mix (Applied Biosystems by Thermo Fisher Scientific) and the Roche 480 LightCycler. All nucleic acid samples were run and analyzed in triplicates using a 10-fold dilution series of IBV-H52 as reference.

Example 3

Preparation of the Vaccine and Challenge Virus

For the animal experiments five IBV were tested, the wildtype IBV-H52, rIBV-wt, rIBV-Δ3ab, rIBV-Δ5ab, and rIBV-Δ3ab5ab. All viruses have been propagated in 8-day-old embryonated SPF eggs (GD, Deventer, Netherlands). The allonatoic fluid was harvested, aliquoted and stored at −80° C. until further use. The virus titer was determined using in sterile phosphate buffered saline (PBS) 10-fold diluted virus. Five eggs for each dilution was inoculated with 100 μl into the allantoic cavity of eight-day-old embryonated SPF eggs, the eggs were sealed and incubated at 37° C. Embryonal dead within the first 24 h after inoculation were considered as unspecific. The eggs were candled daily until day seven after inoculation. Dead embryos and embryos which showed signs specific for IBV (curling and dwarfing of the embryos, clubbing of down, red or hemorrhagic embryos, and possibly white urate deposits in kidneys) were considered as positive. The egg infectious dose 50% ($EID_{50}$) was calculated following the method of Reed and Muench [Reed, L. J., and H. Muench (1938). A simple method of estimating fifty percent endpoints. Am J Epidemiol 27:493-497]. For vaccination the viruses were diluted in sterile PBS to obtain a titer of $10^3$ $EID_{50}$/0.1 ml. The challenge virus M41 of the Massachusetts serotype (obtained from GD Deventer, Deventer, The Netherlands) was propagated in 11-day-old embryonated SPF eggs (VALO BioMedia GmbH, Osterholz-Scharmbeck, Germany) The allantoic fluid was harvested 24 h post inoculation, aliquoted and stored at −80° C. until further use. The virus titer was determined as described above with the exception that 11-day-of embryonated SPF eggs were used. For challenge infection IBV strain M41 was diluted in sterile PBS to obtain a target titer of $10^3$ $EID_{50}$/0.1 ml.

Example 4

Vaccine Efficacy Data 1 for Δ3Ab, Δ5Ab, Δ3Ab5Ab

Material and Methods:

Chickens used for this study were hatched from SPF eggs (GD, Deventer, Netherlands). The chickens were split into seven groups. Groups 1-6 contained 15 chickens while ten chickens were allocated into group 7. At one day of age chickens were transferred to isolators with HEPA filtered supply and exhaust air with regulated humidity (40-70%) and temperature (20-21° C.). Animals were kept under housing conditions in compliance to local and national requirements for animal welfare recommendations. The light regime was adjusted to 12 hours dark and 12 hours light per day. Feed and water were provided ad libitum. After transfer to the isolators the chickens of groups 1-5 were vaccinated at one day of age with 0.1 ml of the diluted vaccines ($10^3$ $EID_{50}$/0.1 ml) via the eye drop route (0.05 ml/eye). The dilution factor was determined based on the titre obtained after virus titration. Chickens of group 1 were vaccinated with IBV-H52 while chickens of groups 2-5 were vaccinated with rIBV-wt (group 2), rIBV-Δ3ab (group 3), rIBV-Δ5ab (group 4), rIBV-Δ3ab5ab (group 5). The chickens of group 6 were not vaccinated and served as challenge control. The chickens of group 7 served as strict negative control (SNC), and were neither vaccinated nor challenged. At seven days post vaccination 5 chickens each from groups 1-6 were removed, euthanized and the trachea from each chicken was taken. The chickens of groups 1-6 were challenged at day 21 post vaccination with $10^{3-}$ $EID_{50}$/0.1 mL of the challenge virus M41 via the eyedrop route as describe above. At seven days post challenge all chickens were euthanized and the tracheas were removed. The retrieved tracheas from day seven post vaccination and day seven post challenge infection were cut into ten transversal sections. The trachea was sliced into three transversal sections of the upper part, four transversal sections of the middle part and three transversal sections of the lower part. The sections were rinsed with prewarmed PBS and examined not later than 2 h after sampling by low-magnification microscopy for ciliary activity. For a given tracheal section, ciliary activity is considered as normal when at least 50% of the internal ring shows vigorous ciliary movement. A chicken is considered either not affected from the virus used for vaccination at day seven post vaccination or not affected from challenge virus thus protected from challenge at seven days after challenge infection if not fewer than 9 out of 10 rings show normal ciliary activity.

Results:

The chickens of each group were observed for clinical signs after vaccination and after challenge infection. After vaccination neither chickens showed signs of disease which could be associated with vaccination. One bird from group 3 was found dead at two days after vaccination. The performed necropsy revealed yolk sac infection. After challenge infection no clinical signs were observed in vaccinated groups 1-5, and the SNC group 7. It needs to be mentioned that from group 1 (IBV-H52) one bird was removed and euthanized at one day after challenge infection. However this bird was already depressed from the $18^{th}$ day after vaccination which is three days prior challenge infection. Necropsy revealed minor digestive observations and an overloaded crop indicating an digestive disorder. In contrast four birds from the challenged non-vaccinated group showed respiratory signs typical for infectious bronchitis between two and three days post challenge infection.

The pathogenicity of each virus was assessed by analysis of the ciliar scores. The ciliar activity is defined as not affected for a given tracheal section when ≥50% of the internal rings shows vigorous ciliary movement, which is a score of 2. The score was on a scale of 0-4, being 0 one hundred percent of the ciliar are moving. The score of 1 means approximately 75% of the tracheal ciliar show movement. Fifty, 25, and <25% of ciliary movement result in a score of 2, 3, and 4, respectively. The highest tracheal lesion score is 40 which is the sum of ten tracheal sections with a score of 4. The sum of each score per chicken was averaged and the differences were analysed. The mean tracheal lesion scores of the different groups are listed in Table 5. Results of this study showed that each of the three recombinant IBV test items (rIBV-Δ3ab, rIBV-Δ5ab, and rIBV-Δ3abΔ5ab) can be administered safely. This is, since the mean ciliostasis score at 7 days post administration of one dose of the deletion mutants (rIBV-Δ3ab, rIBV-Δ5ab, and rIBV-Δ3abΔ5ab) was significantly lower (p<0.05) than the mean tracheal lesion score at 7 days post administration of the recombinant parental virus (rIBV-wt) when administered to day-old SPF layer chickens. A similar effect was observed when comparing the deletion mutants (rIBV-Δ3ab, rIBV-Δ5ab, and rIBV-Δ3abΔ5ab) with IBV-H52. Furthermore, none of the chickens showed notable clinical signs of IB or died from causes attributable to the test items after administration of one of the three test items containing deletions in the viral genome. Taken together, all three recombinant IBV test items (rIBV-Δ3ab, rIBV-Δ5ab, and rIBV-Δ3abΔ5ab) were more safe as the controls (rIBV-wt or IBV-H52) which did not contain a deletion in the aforementioned deletion mutant IBV.

TABLE 5

Mean tracheal lesion scores of the different groups at 7 days post vaccination

| Group | Vaccine | Average score |
|---|---|---|
| 1 | IBV-H52 | 26 |
| 2 | rIBV-wt | 40 |
| 3 | rIBV-Δ3ab | 8 |

TABLE 5-continued

Mean tracheal lesion scores of the different groups at 7 days post vaccination

| Group | Vaccine | Average score |
|---|---|---|
| 4 | rIBV- Δ5ab | 19 |
| 5 | rIBV- Δ3abΔ5ab | 8 |
| 6 | NV* | 2 |

*not vaccinated

Furthermore it was analysed if the recombinant IBV containing deletions in the genome (rIBV-Δ3ab, rIBV-Δ5ab, and rIBV-Δ3abΔ5ab) were able to induce protection from a challenge infection using the virulent IBV strain M41. The targeted challenge dose was $10^3$ $EID_{50}$/chicken applied in 100 µl of diluted virus with 50 µl into each eye by the eyedrop method. The back titration of the challenge virus revealed that the challenge dose was $10^{3.78}EID_{50}$/100 µl, being almost 10-fold higher as planned.

TABLE 6

Protection and mean tracheal lesion scores of the different groups at 7 days post challenge infection

| Group | Vaccine | Protected animals/total animals (Average score) |
|---|---|---|
| 1 | IBV-H52 | 21 |
| 2 | rIBV-wt | 12 |
| 3 | rIBV-Δ3ab | 17 |
| 4 | rIBV- Δ5ab | 6 |
| 5 | rIBV- Δ3abΔ5ab | 19 |
| 6 | NV* | 40 |
| 7 | NV/NC** | 0 |

*not vaccinated
**not vaccinated/not challenged

The test met all validity criteria according to the European Pharmacopoea EP 0442 as all challenged control chickens showed extreme loss of vigour of ciliary activity as indicated with an average score of 40. In addition, during the observation period between vaccination and challenge not more than 10 percent of vaccinated or control chickens showed abnormal clinical signs or died from causes not attributable to the tested vaccines. Results of this study showed the efficacy of each of the three tested recombinant IBV containing deletion in the viral genome (rIBV-Δ3ab, rIBV-Δ5ab, and rIBV-Δ3abΔ5ab) as none of the vaccinated birds showed either clinical signs or died after challenge with the IBV strain M41.

For test item rIBV-Δ3ab, 6 out of 9 birds (67%) complied with the test post challenge regarding efficacy as stated in EP 0442 (9 out of 10 tracheal rings show normal ciliar activity). For test item rIBV-Δ5ab 10 out of 10 birds (100%), and for test item rIBV-Δ3abΔ5ab 3 out of 10 birds (30%) were protected from challenge infection. Interestingly after vaccination with the wild type virus IBV-H52 4 out of 9 birds (44%) were protected while 7 out of 10 birds (70%) were protected from challenge infection after vaccination with rIBV-wt. The unexpected low protection rate might be caused by the rather high titer of the used challenge virus, since even the IBV-H52 was not able to induce a protection ≥90%. Taken together, all three recombinant IBV test items (rIBV-Δ3ab, rIBV-Δ5ab, and rIBV-Δ3abΔ5ab) can be administered more safe as the controls (rIBV-wt or IBV-H52), however, all mutants are at least as efficacious as the controls.

Example 5

Vaccine Efficacy Data 2 for Δ3Ab, Δ5Ab, Δ3Ab5Ab

Materials and Method:

In order to validate the experimental results the above experiments (Examples 1 to 4) were repeated from the beginning to have a second independent data set. Constructs were generated a second time according to the methods as already described above. Vaccination and challenge experiment was performed using viruses containing the same gene deletions (Δ3ab, Δ5ab, Δ3ab5ab) and the nonmodifed viruses (IBV-H52, rIBV-WT) as controls. The experiment was designed as described under Example 4. For clarity, chickens of group 1 were vaccinated with IBV-H52 while chickens of groups 2-5 were vaccinated with rIBV-wt (group 2), rIBV-Δ3ab (group 3), rIBV-Δ5ab (group 4), and rIBV-Δ3ab5ab (group 5). The chickens of group 6 were not vaccinated and challenged and served as challenge control. The chickens of group 7 served as strict negative control (SNC), and were neither vaccinated nor challenged. The chickens were vaccinated at one-day-old with $10^3$ EID$_{50}$/chickens and challenged at 21 days post vaccination with $10^3$ EID$_{50}$/chickens with the virulent IBV strains M41. Both virus inoculations were performed via eyedrop. In order to analyze the safety of the viruses the ciliary activity of the trachea were investigated as described under Example 4 at 7 days post vaccination in 5 chickens each of groups 1-5 and 5 chickens of the group 7 (SNC). To investigate the ability of the viruses to protect from tracheal damage after challenge infection the tracheas of the remaining chickens were analyzed for their ciliary activity at day 7 after challenge infection. The ciliary activity of the trachea was investigated as described under Example 4. During the course of the experiments all chickens were observed daily for clinical signs.

Results:

Clinical observations related to vaccine administration were reported neither post vaccination nor post challenge infection in any of the groups. The tracheal lesion score was investigated as described in Example 4 with one exception. At day 7 post vaccination 5 birds of the SNC were used as negative control for the scoring of the lesion in the tracheal cilia due to animal welfare reasons. In short the highest score of a trachea is 40 which indicates the highest possible damage to the tracheal cilia. In table 7 the average lesions scores of 5 birds per group 1 at 7 days post vaccination are shown. All three recombinant IBV test items (rIBV-Δ3ab, rIBV-Δ5ab, and rIBV-Δ3abΔ5ab) can be administered more safe as the controls (rIBV-wt or IBV-H52) as indicated by the average lesion scores (Table 7). Therefore, the above mentioned results were validated. The three recombinant IBV test items (rIBV-Δ3ab, rIBV-Δ5ab, and rIBV-Δ3abΔ5ab) were more safe more safe when compared to IBV-H52 and rIBV-wt.

TABLE 7

Mean tracheal lesion scores of the different groups at 7 days post vaccination

| Group | Vaccine | Average score |
|---|---|---|
| 1 | IBV-H52 | 26 |
| 2 | rIBV-wt | 19 |
| 3 | rIBV-Δ3ab | 5 |
| 4 | rIBV- Δ5ab | 15 |
| 5 | rIBV- Δ3abΔ5ab | 11 |
| 7 | SNC* | 5 |

*strict negative control

Furthermore it was tested if the recombinant IBV containing genome deletions (rIBV-Δ3ab, rIBV-Δ5ab, and rIBV-Δ3abΔ5ab) were able to induce protection from a challenge infection using the virulent IBV strain M41. The targeted challenge dose was $10^3$ EID$_{50}$/chicken applied in 100 µl of diluted virus with 50 µl into each eye by the eyedrop method. The back titration of the challenge virus revealed that the challenge dose was $10^{3.36}$EID$_{50}$/100 µl which was in the expected range.

The challenge infection was valid as all challenged non vaccinated control chickens (group 6) showed extreme loss of vigour of ciliary activity as indicated with an average score of 39 (Table 8) at 7 days after challenge infection. Furthermore, during the observation period between vaccination and challenge no clinical signs attributable to the vaccine application was observed in the chickens.

Taken together, all three recombinant IBV test items (rIBV-Δ3ab, rIBV-Δ5ab, and rIBV-Δ3abΔ5ab) are more safe after application as a vaccine as the controls (rIBV-wt or IBV-H52), however, all mutants are at least as efficacious as the controls.

TABLE 8

Protection and mean tracheal lesion scores of the different groups at 7 days post challenge infection

| Group | Vaccine | Protected animals/ total animals (Average score) |
|---|---|---|
| 1 | IBV-H52 | 15 |
| 2 | rIBV-wt | 12 |
| 3 | rIBV-Δ3ab | 14 |
| 4 | rIBV- Δ5ab | 11 |
| 5 | rIBV- Δ3abΔ5ab | 12 |
| 6 | NV* | 39 |
| 7 | SNC (NV/NC)** | 5 |

*not vaccinated
**strict negative control (not vaccinated/not challenged)

Example 6

Generation and Testing of Single Deletion Mutants Δ3a, Δ3b, Δ5a, Δ5b

Material and Methods: Construction of Plasmids with Single Deletion in Either Gene 3a, 3b, 5a, or 5b.

In order to analyze whether the single proteins 3a, 3b, 5a, or 5b have an impact on the virulence of IBV the expression of the proteins were inactivated by single deletion mutants. To this end cDNA-fragments containing the deletion of either 3a, 3b, 5a, or 5b were synthetically generated and ligated into pUC57-simple by Genscript (pUC57-Δ3a; pUC57-Δ3b, pUC57-Δ5a, pUC57-Δ5b). The plasmid pUC57-Δ3a was cleaved with the restriction enzymes NheI and PmlI and the appropriate IBV-specific cDNA sequences were ligated into the NheI/PmlI cleaved plasmid p-IBV-5-1b-S-SIR (see also table 1) to obtain p-IBV-5-1b-S-SIR-Δ3a.

In a next step plasmid p-IBV-3T (see also table 1) was cleaved with EcoRI and the cDNA-fragment was ligated into the EcoRI cleaved p-IBV-5-1b-S-SIR-Δ3a to obtain p-IBV-5-1b-S-SIRΔ3a-3T, now called p-IBV-Δ3a. The same strategy was employed for the generation of p-IBV-Mb, except the fragment of plasmid pUC57-Δ3b was used. For the generation of plasmids containing the deletion of either 5a or 5b a different cloning procedure was chosen. To this end plasmid pUC57-Δ5a was cleaved with two restriction enzymes (AfeI, NheI) and the eluted cDNA-fragment was ligated into the appropriately cleaved p-IBV-3T to obtain p-IBV-Δ5a-3T. Plasmid p-IBV-Δ5a-3T was cleaved with EcoRI and the eluted cDNA-fragment was ligated into the EcoRI-cleaved p-IBV-5-1b-S-SIR to obtain the target plasmid p-IBV-5-1b-S-SIRΔ5a-3T, now called p-IBV-Δ5a. The same strategy was used for the generation of p-IBV-Δ5b except plasmid pUC57-Δ5b was used.

Generation of Recombinant IBV with Single Deletions in the Accessory Proteins 3a, 3b, 5a, and 5b.

IBV containing deletions in coding regions of either 3a, 3b, 5a, or 5b were generated as described above. In short, run-off-transcripts from linearized plasmid p-IBV-N and either plasmid p-IBV-Δ3a, p-IBV-Δ3b, p-IBV-Δ5a, or p-IBV-Δ5b were generate as described in Example 2. The generation of the recombinant IBV was performed as described in Example 2, using LR7 cells infected with mIBV and subsequently transfection with cRNA of four combinations (cRNA-IBV-N, cRNA-IBV-Δ3a; cRNA-IBV-N, cRNA-IBV-Δ3b; cRNA-IBV-N, cRNA-IBV-Δ5a; cRNA-IBV-N, cRNA-IBV-Δ5b). The recombinant viruses (rIBV-Δ3a, rIBV-Δ3b, rIBV-Δ5a, rIBV-Δ5b) were subsequently rescued as described in Example 2 and propagated as described in Example 3. The virus titer in $EID_{50}$ of the final virus stocks was determined in 8-day-old embryonated SPF eggs using 5 eggs per dilution using the Reed and Muench [Reed, L. J., and H. Muench (1938). A simple method of estimating fifty percent endpoints. Am J Epidemiol 27:493-497].

Animal Experiments:

The animal experiments were performed as described in Example 4. Fifteen SPF chickens per group were vaccinated with $10^3$ $EID_{50}$/chicken in 100 µl of either IBV-H52 (group 1), rIBV-wt (group 2), rIBV-Δ3a (group 3), rIBV-Δ3b (group 4), rIBV-Δ5a (group 5), or rIBV-Δ5b (group 6) via the eyedrop route. Ten chickens of group 7 and group 8 were not vaccinated. Chickens of group 8 served as strict negative control (SNC) which were neither vaccinated nor challenged. All birds were kept in isolators to omit virus transmission between groups. At 7 day post vaccination five birds of groups 1-6 and five birds of group 8 were removed for the assessment of ciliary activity of the trachea as described in Example 4. Challenge infection was performed with chickens of groups 1-7 at day 21 post vaccination using $10^3$ $EID_{50}$/chicken in 100 µl of the virulent IBV strain M41, while chickens of group 8 were left unchallenged. Remaining chickens of all groups were euthanized and the trachea was removed for analysis of ciliary activity of the trachea as described in Example 4 at 7 days after challenge infection.

In table 9 the averages of the tracheal scores of the ciliary activity at day 7 post vaccination are shown. The statistical analysis revealed that lesions scores of the experimental groups 3-6 (rIBV-Δ3a, rIBV-Δ3b, rIBV-Δ5a, rIBV-Δ5) were statistical different lower (p<0.05) from the scores of group 2 (rIBV-wt). A similar effect was observed when comparing the deletion mutants (rIBV-Δ3a, rIBV-Δ3b, rIBV-Δ5a, rIBV-Δ5) with IBV-H52.

TABLE 9

Mean tracheal lesion scores of the different groups at 7 days post vaccination

| Group | Vaccine | Average score |
|---|---|---|
| 1 | IBV-H52 | 25 |
| 2 | rIBV-wt | 36 |
| 3 | rIBV-Δ3a | 18 |
| 4 | rIBV- Δ3b | 18 |
| 5 | rIBV- Δ5a | 16 |
| 6 | rIBV- Δ5b | 23 |
| 8 | SNC* | 4 |

*strict negative control

The challenge infection was valid as all challenged control chickens (group 7) showed extreme loss of vigour of ciliary activity as indicated with an average score of 36 (Table 10) at 7 days after challenge infection.

Vaccinated chickens, either vaccinated with the control IBV (IBV-H52, rIBV-wt) or the deletion mutants (rIBV-Δ3a, rIBV-Δ3b, rIBV-Δ5a, and rIBV-Δ5b) were protected from challenge infection since the average lesion score of the ciliary activity was substantial lower than the lesion score of the not vaccinated but challenged chickens (group 7). Taken together, IBV containing deletions in either of the genes 3a, 3b, 5a, or 5b are attenuated in young chickens but can induce significant protection comparable to their parental (IBV-H52) and recombinant parental strain (rIBV-wt) when challenged with a virulent IBV of the Massachusetts serotype (here strain M41).

TABLE 10

Mean tracheal lesion scores of the different groups at 7 days post vaccination

| Group | Vaccine | Average score |
|---|---|---|
| 1 | IBV-H52 | 1 |
| 2 | rIBV-wt | 2 |
| 3 | rIBV-Δ3a | 9 |
| 4 | rIBV- Δ3b | 5 |
| 5 | rIBV- Δ5a | 11 |
| 6 | rIBV- Δ5b | 8 |
| 7 | NV* | 36 |
| 8 | SNC (NV/NC)** | 0 |

*not vaccinated
**strict negative control (not vaccinated/not challenged)

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

The invention claimed is:

1. A safe and efficacious vaccine against infectious bronchitis virus (IBV), comprising:
   an IBV in an amount effective to reduce the incidence or severity of tracheal lesions in an animal immunized with the IBV, relative to a non-immunized control animal of the same species, when subsequently infected with a pathogenic IBV strain; and
   a pharmaceutically acceptable carrier,
   wherein the IBV comprises an inactivated ORF 5a that attentuates a virulent parent strain.

2. The vaccine of claim 1, wherein the inactivated ORF 5a comprises a partial deletion, a partial truncation, a partial inversion, a partial relocation, an insertion, and/or a substitution of nucleic acids.

3. The vaccine of claim 1, wherein the ORF 5a start codon is inactivated.

4. The vaccine of claim 3, wherein the ORF 5a start codon comprises a deletion, substitution, and/or inversion.

5. The vaccine of claim 1, wherein between 1 and 194 nucleotides beginning from the 5' terminus of the ORF 5a start codon are deleted, substituted, and/or inverted.

6. The vaccine of claim 1, wherein the ORF 5a start codon comprises a nucleotide deletion.

7. The vaccine of claim 1, wherein the IBV is recombinant.

8. The vaccine of claim 1, wherein the IBV further comprises an inactivated ORF 5b.

9. The vaccine of claim 1, wherein the IBV further comprises an inactivated ORF 3a, an inactivated ORF 3b, and an inactivated ORF 5b.

10. A method for immunizing a subject comprising:
    administering to the subject the vaccine of claim 1.

11. The method of claim 10, wherein a protective immune response effective to reduce or eliminate subsequent IBV-infection clinical signs in the subject, relative to a non-immunized control subject of the same species, is elicited by administration of the vaccine.

12. The method of claim 10, wherein a protective immune response effective to reduce ciliostasis risk in the subject, relative to a non-immunized control subject of the same species, is elicited by administration of the vaccine.

13. The method of claim 10, wherein the vaccine is administered subcutaneously, intramuscularly, orally, in ovo, via spray, via drinking water, or by eye drop.

14. The method of claim 10, wherein the subject is an avian.

15. The method of claim 10, wherein the subject is a poultry.

* * * * *